(12) United States Patent
Simpson et al.

(10) Patent No.: US 11,832,943 B2
(45) Date of Patent: *Dec. 5, 2023

(54) SENSORS FOR CONTINUOUS ANALYTE MONITORING, AND RELATED METHODS

(71) Applicant: DexCom, Inc., San Diego, CA (US)

(72) Inventors: Peter C. Simpson, Cardiff, CA (US); Jennifer Blackwell, San Diego, CA (US); Sebastian Bohm, San Diego, CA (US); Michael J. Estes, San Diego, CA (US); Jeff Jackson, San Diego, CA (US); Jason Mitchell, San Diego, CA (US); Jack Pryor, San Diego, CA (US); Daiting Rong, San Diego, CA (US); Sean T. Saint, San Diego, CA (US); Disha B. Sheth, San Marcos, CA (US); Shanger Wang, Castro Valley, CA (US)

(73) Assignee: DexCom, Inc., San Diego, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/156,393

(22) Filed: Jan. 22, 2021

(65) Prior Publication Data

US 2021/0275063 A1 Sep. 9, 2021

Related U.S. Application Data

(63) Continuation of application No. 14/964,433, filed on Dec. 9, 2015, now Pat. No. 10,932,709, which is a
(Continued)

(51) Int. Cl.
*A61B 5/1473* (2006.01)
*A61B 5/145* (2006.01)
(Continued)

(52) U.S. Cl.
CPC ........ *A61B 5/1473* (2013.01); *A61B 5/14503* (2013.01); *A61B 5/14532* (2013.01);
(Continued)

(58) Field of Classification Search
None
See application file for complete search history.

(56) References Cited

U.S. PATENT DOCUMENTS 5,190,529 A 3/1993 McCrory et al.
5,299,571 A 4/1994 Mastrototaro
(Continued)

FOREIGN PATENT DOCUMENTS

EP 0789540 B1 9/2001
EP 0729366 B1 7/2002
(Continued)

OTHER PUBLICATIONS

Buckingham M.D.B., et al., "Preventing Hypoglycemia Using Predictive Alarm Algorithms and Insulin Pump Suspension," Diabetes Technology & Therapeutics, vol. 11, No. 2, 2009, pp. 93-97.
(Continued)

*Primary Examiner* — Meredith Weare
(74) *Attorney, Agent, or Firm* — Snell & Wilmer LLP

(57) ABSTRACT

Sensor devices including dissolvable tissue-piercing tips are provided. The sensor devices can be used in conjunction with dissolvable needles configured for inserting the sensor devices into a host. Hardening agents for strengthening membranes on sensor devices are also provided. Methods of using and fabricating sensor devices are also provided.

10 Claims, 31 Drawing Sheets

Related U.S. Application Data continuation of application No. 14/250,341, filed on Apr. 10, 2014, now abandoned, which is a continuation-in-part of application No. 13/780,808, filed on Feb. 28, 2013, now abandoned.

(60) Provisional application No. 61/713,338, filed on Oct. 12, 2012.

(51) Int. Cl.
    *A61B 5/00* (2006.01)
    *A61B 17/34* (2006.01)
    *A61B 17/00* (2006.01)

(52) U.S. Cl.
    CPC .......... *A61B 5/4839* (2013.01); *A61B 5/6848* (2013.01); *A61B 17/3468* (2013.01); *A61B 2017/00004* (2013.01)

(56) References Cited

U.S. PATENT DOCUMENTS

| | | | |
|---|---|---|---|
| 5,390,671 A | 2/1995 | Lord et al. | |
| 5,391,250 A | 2/1995 | Cheney, II et al. | |
| 5,527,288 A | 6/1996 | Gross et al. | |
| 5,569,186 A | 10/1996 | Lord et al. | |
| 5,746,217 A | 5/1998 | Erickson et al. | |
| 5,800,420 A | 9/1998 | Gross et al. | |
| 5,807,306 A | 9/1998 | Shapland et al. | |
| 5,807,375 A | 9/1998 | Gross et al. | |
| 5,820,622 A | 10/1998 | Gross et al. | |
| 5,848,991 A | 12/1998 | Gross et al. | |
| 5,885,251 A * | 3/1999 | Luther | A61M 25/0637 604/164.11 |
| 5,931,814 A | 8/1999 | Alex et al. | |
| 5,954,643 A | 9/1999 | Vanantwerp et al. | |
| 5,964,744 A | 10/1999 | Balbierz et al. | |
| 5,997,501 A | 12/1999 | Gross et al. | |
| 6,071,294 A | 6/2000 | Simons et al. | |
| 6,103,033 A | 8/2000 | Say et al. | |
| 6,132,449 A | 10/2000 | Lum et al. | |
| 6,175,752 B1 | 1/2001 | Say et al. | |
| 6,186,982 B1 | 2/2001 | Gross et al. | |
| 6,275,717 B1 | 8/2001 | Gross et al. | |
| 6,360,888 B1 | 3/2002 | McIvor et al. | |
| 6,405,066 B1 | 6/2002 | Essenpreis et al. | |
| 6,424,847 B1 | 7/2002 | Mastrototaro et al. | |
| 6,520,326 B2 | 2/2003 | McIvor et al. | |
| 6,537,242 B1 | 3/2003 | Palmer | |
| 6,558,320 B1 | 5/2003 | Causey, III et al. | |
| 6,692,456 B1 | 2/2004 | Eppstein et al. | |
| 6,712,776 B2 | 3/2004 | Latterell et al. | |
| 6,892,085 B2 | 5/2005 | McIvor et al. | |
| 6,997,886 B2 | 2/2006 | Latterell et al. | |
| 7,029,444 B2 | 4/2006 | Shin et al. | |
| 7,041,057 B1 | 5/2006 | Faupel et al. | |
| 7,146,202 B2 | 12/2006 | Ward et al. | |
| 7,310,543 B2 | 12/2007 | Smart et al. | |
| 7,381,184 B2 | 6/2008 | Funderburk et al. | |
| 7,842,210 B2 | 11/2010 | Chen | |
| 8,114,006 B2 | 2/2012 | Cox et al. | |
| 8,187,433 B2 | 5/2012 | Ward et al. | |
| 8,224,410 B2 | 7/2012 | Hadvary et al. | |
| 8,512,243 B2 | 8/2013 | Stafford | |
| 8,694,069 B1 | 4/2014 | Kosa et al. | |
| 9,357,951 B2 | 6/2016 | Simpson et al. | |
| 9,480,421 B2 | 11/2016 | Stafford | |
| 9,844,328 B2 | 12/2017 | Simpson et al. | |
| 10,448,872 B2 | 10/2019 | Wolfe et al. | |
| 10,932,709 B2 * | 3/2021 | Simpson | A61B 5/14532 |
| 2001/0016702 A1 | 8/2001 | Benjamin | |
| 2002/0022855 A1 | 2/2002 | Bobroff et al. | |
| 2002/0072720 A1 | 6/2002 | Hague et al. | |
| 2002/0137998 A1 | 9/2002 | Smart et al. | |
| 2004/0138541 A1 | 7/2004 | Ward et al. | |
| 2004/0138543 A1 | 7/2004 | Russell et al. | |
| 2004/0254433 A1 | 12/2004 | Bandis et al. | |
| 2005/0004438 A1 | 1/2005 | Ward et al. | |
| 2005/0143635 A1 | 6/2005 | Kamath et al. | |
| 2006/0004272 A1 | 1/2006 | Shah et al. | |
| 2006/0008500 A1 | 1/2006 | Chavan et al. | |
| 2006/0020192 A1 | 1/2006 | Brister et al. | |
| 2006/0021092 A1 | 1/2006 | McCourt et al. | |
| 2006/0030824 A1 | 2/2006 | Hunn et al. | |
| 2006/0030833 A1 | 2/2006 | Harris et al. | |
| 2006/0211921 A1 | 9/2006 | Brauker et al. | |
| 2006/0289307 A1 | 12/2006 | Yu et al. | |
| 2007/0027370 A1 | 2/2007 | Brauker et al. | |
| 2007/0038014 A1 | 2/2007 | Cox et al. | |
| 2007/0078322 A1 | 4/2007 | Stafford | |
| 2007/0129619 A1 | 6/2007 | Ward et al. | |
| 2007/0191737 A1 | 8/2007 | Freeman et al. | |
| 2007/0235331 A1 | 10/2007 | Simpson et al. | |
| 2008/0033269 A1 | 2/2008 | Zhang | |
| 2008/0076974 A1 | 3/2008 | Yamazaki et al. | |
| 2008/0249383 A1 | 10/2008 | Sass et al. | |
| 2008/0249385 A1 | 10/2008 | Phan | |
| 2009/0105605 A1 | 4/2009 | Abreu | |
| 2009/0131768 A1 * | 5/2009 | Simpson | A61B 5/14532 600/309 |
| 2009/0171302 A1 | 7/2009 | Eramo, Jr. et al. | |
| 2010/0121307 A1 | 5/2010 | Lockard et al. | |
| 2010/0160756 A1 | 6/2010 | Petisce et al. | |
| 2010/0219085 A1 | 9/2010 | Oviatt, Jr. | |
| 2010/0286496 A1 | 11/2010 | Simpson et al. | |
| 2011/0073475 A1 * | 3/2011 | Kastanos | A61B 5/14865 204/403.01 |
| 2011/0077490 A1 * | 3/2011 | Simpson | A61B 5/1468 600/345 |
| 2011/0230735 A1 | 9/2011 | Wolfe et al. | |
| 2012/0028283 A1 | 2/2012 | Hoss et al. | |
| 2012/0190952 A1 | 7/2012 | Stafford | |
| 2012/0253145 A1 | 10/2012 | Stafford et al. | |
| 2013/0056144 A1 * | 3/2013 | Kotzan | A61B 5/14532 427/2.11 |
| 2013/0253289 A1 | 9/2013 | Hadvary et al. | |
| 2013/0253293 A1 | 9/2013 | Ocvirk et al. | |
| 2013/0253438 A1 | 9/2013 | Badawi et al. | |
| 2014/0107450 A1 | 4/2014 | Simpson et al. | |
| 2014/0213866 A1 | 7/2014 | Simpson et al. | |
| 2015/0216462 A1 | 8/2015 | Kastanos et al. | |
| 2016/0089065 A1 | 3/2016 | Simpson et al. | |
| 2016/0113556 A1 | 4/2016 | Simpson et al. | |
| 2019/0209057 A1 | 7/2019 | Simpson et al. | |

FOREIGN PATENT DOCUMENTS

| | | |
|---|---|---|
| JP | 2006286986 A | 10/2006 |
| WO | WO-9856293 A1 | 12/1998 |
| WO | WO-0247745 A2 | 6/2002 |
| WO | WO-2011110202 A1 | 9/2011 |

OTHER PUBLICATIONS

Extended European Search Report for Application No. 20157783.0 dated Jul. 14, 2020, 11 pages.

Gunatillake P., et al., "Recent Developments in Biodegradable Synthetic Polymers," Biotechnology Annual Review (2006), vol. 12, pp. 301-347.

Miller P.R. et al., "Multiplexed Microneedle-Based Biosensor Array for Characterization of Metabolic Acidosis," Short Communication—Talanta, vol. 88, 2012, pp. 739-742.

Valdes-Ramirez G., et al., "Multiplexed and Switchable Release of Distinct Fluids from Microneedle Platforms via Conducting Polymer Nanoactuators for Potential Drug Delivery," Sensors and Actuators, vol. 8 (161), 2012, pp. 1018-1024.

Windmiller J.R., et al., "Bicomponent Microneedle Array Biosensor for Minimally-Invasive Glutamate Monitoring," Electroanalysis, vol. 23 (10), 2011, pp. 2302-2309.

(56) References Cited

OTHER PUBLICATIONS

Windmiller J.R., et al., "Microneedle Array-Based Carbon Paste Amperometric Sensors and Biosensors," Analyst, vol. 136 (9), 2011, pp. 1846-1851.

* cited by examiner

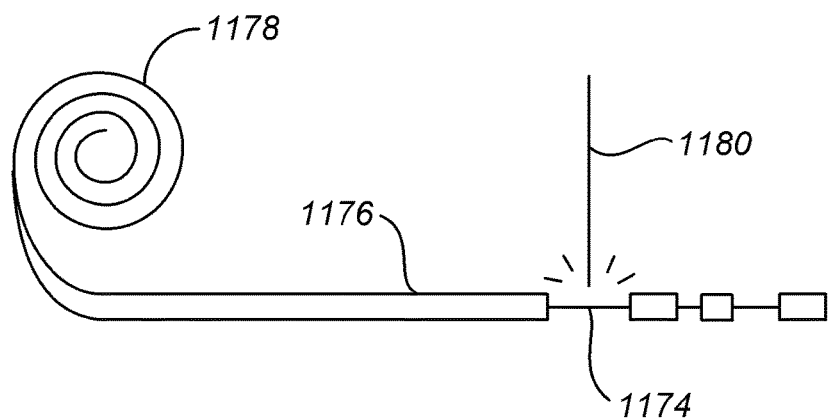
FIG. 34
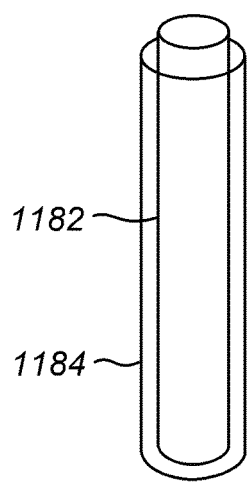 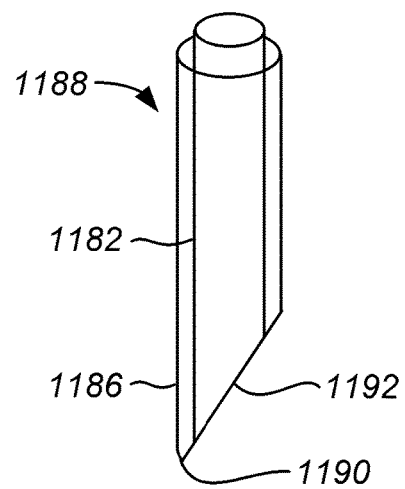 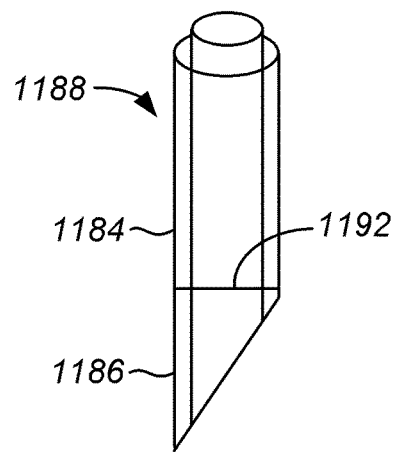
FIG. 35   FIG. 36   FIG. 37

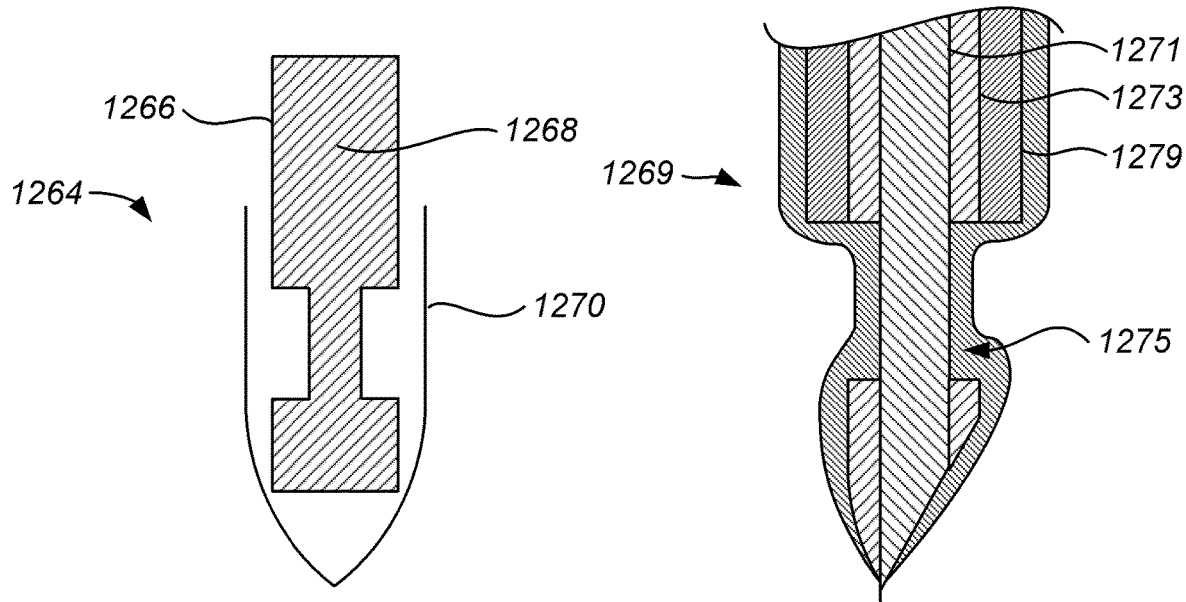
FIG. 52
FIG. 52A
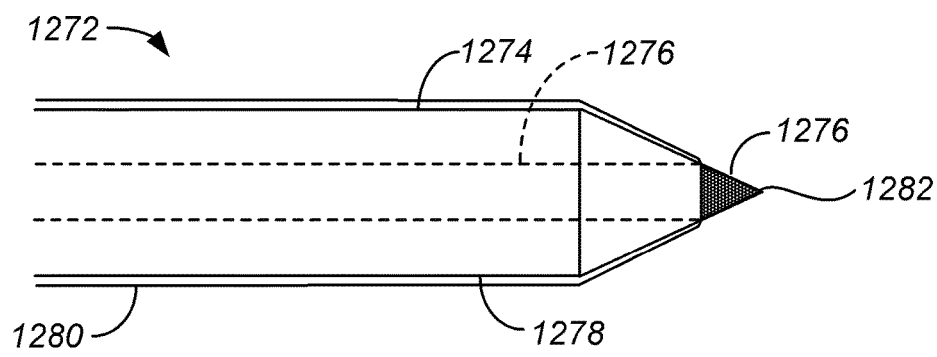
FIG. 53
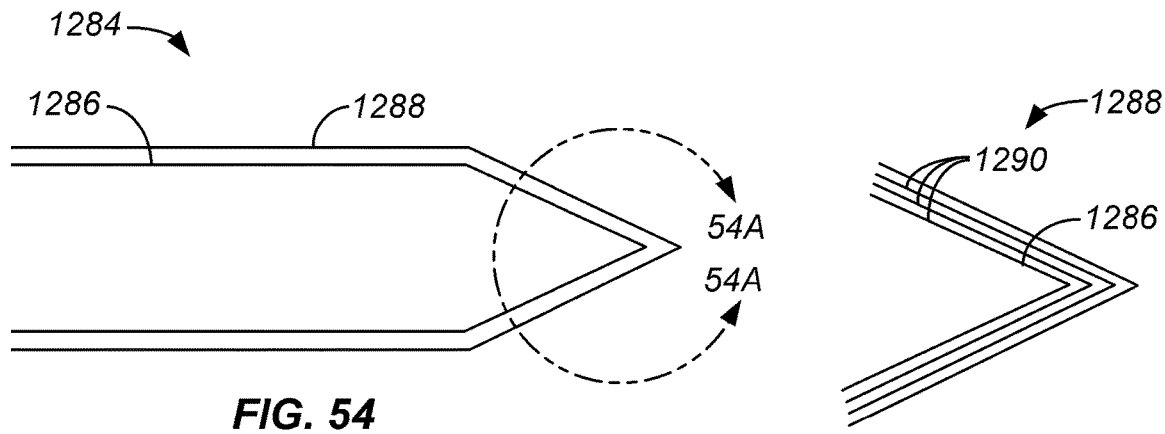
FIG. 54
FIG. 54A

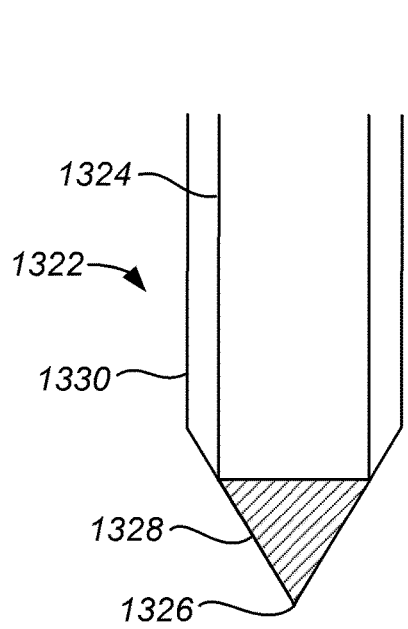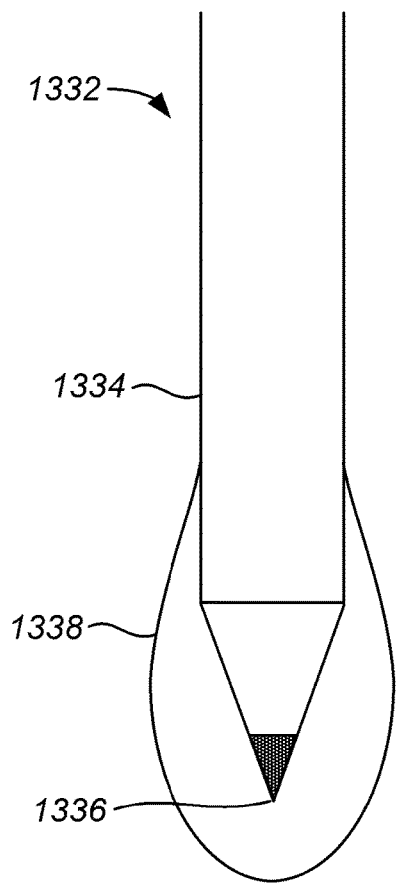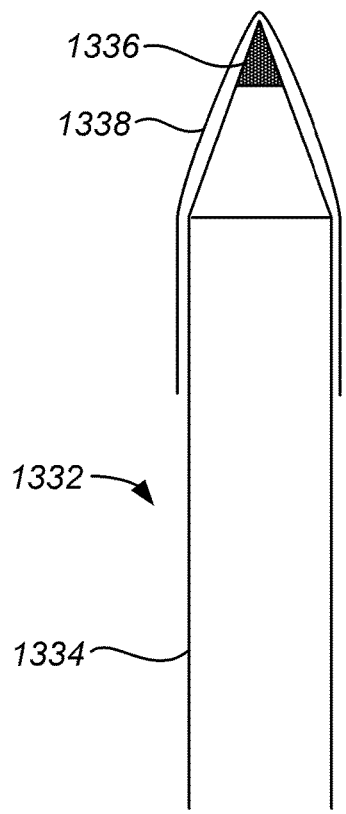
FIG. 60
FIG. 61
FIG. 62

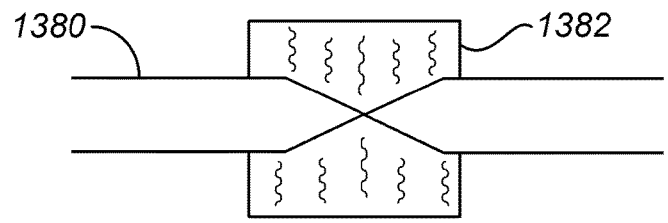
FIG. 68
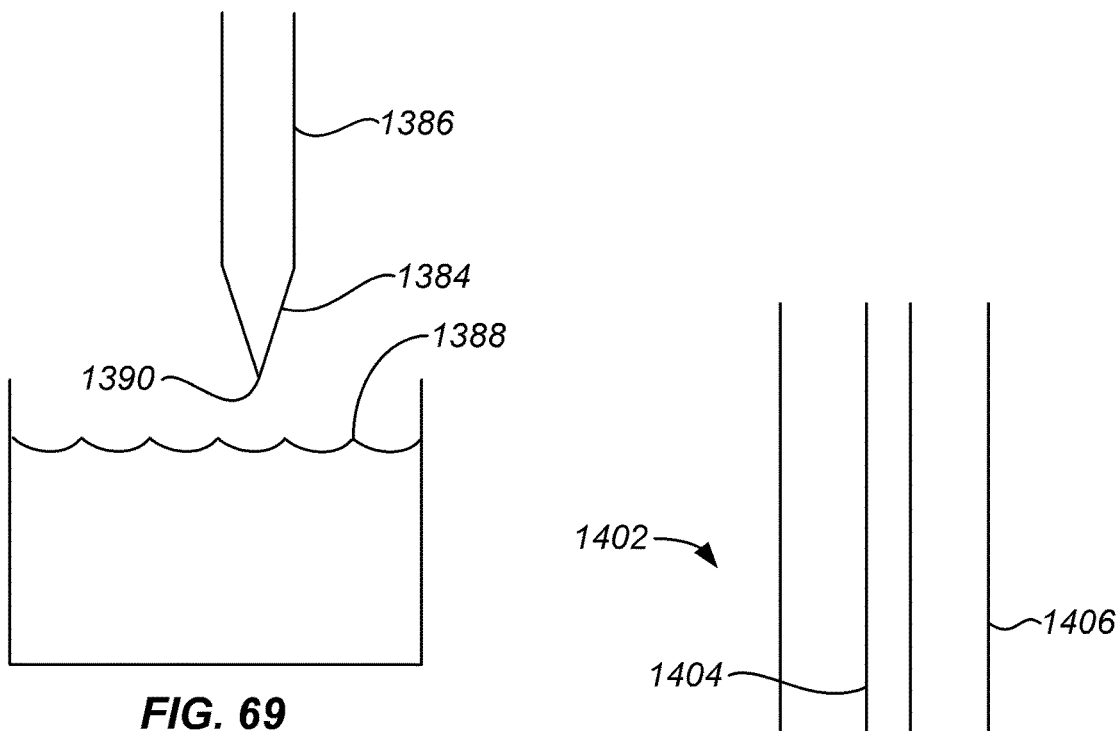
FIG. 69
FIG. 71
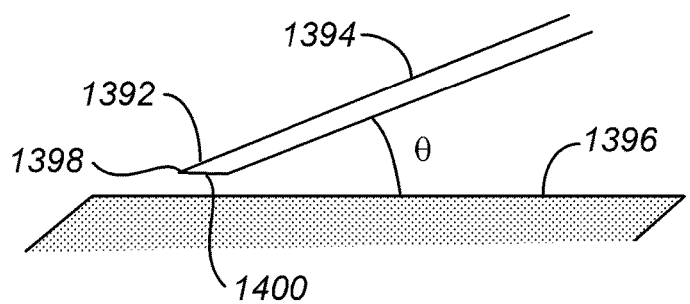
FIG. 70

SENSORS FOR CONTINUOUS ANALYTE MONITORING, AND RELATED METHODS

INCORPORATION BY REFERENCE TO RELATED APPLICATIONS

Any and all priority claims identified in the Application Data Sheet, or any correction thereto, are hereby incorporated by reference under 37 C.F.R. § 1.57. This application is a continuation of U.S. application Ser. No. 14/964,433, filed on Dec. 9, 2015, which is a continuation of U.S. application Ser. No. 14/250,341, filed on Apr. 10, 2014, which is a continuation-in-part of U.S. patent application Ser. No. 13/780,808, filed on Feb. 28, 2013, which claims the benefit of U.S. patent application Ser. No. 61/713,338, filed on Oct. 12, 2012. Each of the aforementioned applications is incorporated by reference herein in its entirety, and each is hereby expressly made a part of this specification.

TECHNICAL FIELD

The present embodiments relate to systems and methods for measuring an analyte concentration in a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements associated with the deterioration of small blood vessels, for example, kidney failure, skin ulcers, or bleeding into the vitreous of the eye. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements may be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The various present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that tack sensors include a sharpened tip that remains implanted in the tissue throughout the usable life of the sensor. Leaving the sharpened tip in vivo for an extended period of time may cause trauma to surrounding tissue, leading to scarring and inhibition of wound healing. Some of the present embodiments provide solutions to this problem.

In recognition of the foregoing problem, in a first aspect certain of the present embodiments comprise a sensor device for measuring an analyte concentration in a host, the sensor device comprising: a sensor unit comprising a sensor body, at least one electrode, and a membrane covering at least a portion of the at least one electrode, the sensor body having a blunt tip; a piercing element comprising a material that rapidly dissolves upon insertion into the host, the piercing element abutting the sensor tip and being capable of piercing tissue; and a mounting unit spaced from the sensor tip and configured to support the sensor device on an exterior surface of the host's skin.

In an embodiment of the first aspect, the piercing element is secured to the sensor tip.

In an embodiment of the first aspect, the piercing element is adhered to the sensor tip.

In an embodiment of the first aspect, the piercing element is not secured to the sensor tip, but is maintained in abutting contact therewith.

In an embodiment of the first aspect, a sleeve surrounding the sensor tip and the piercing element maintains the abutting contact.

In an embodiment of the first aspect, the piercing element comprises a coating that covers at least a portion of the sensor body including the sensor tip.

In an embodiment of the first aspect, the coating comprises a sharp coating tip.

In an embodiment of the first aspect, the material of the piercing element comprises a material that suppresses wounding.

In an embodiment of the first aspect, the material of the piercing element comprises a material that promotes rapid wound healing.

In an embodiment of the first aspect, the material of the piercing element comprises a material that induces osmotic pressure or oncotic pressure.

In an embodiment of the first aspect, the material of the piercing element comprises one or more drugs.

In an embodiment of the first aspect, the material of the piercing element comprises a vascular endothelial growth factor (VEGF).

In an embodiment of the first aspect, the material of the piercing element comprises at least one of a salt, a metallic salt, a sugar, a synthetic polymer, polylactic acid, polyglycolic acid, or a polyphosphazene.

In an embodiment of the first aspect, the material of the piercing element biodegrades/dissolves within a first day after insertion into the host.

In an embodiment of the first aspect, the material of the piercing element biodegrades/dissolves within three hours after insertion into the host.

In an embodiment of the first aspect, the piercing element does not extend past the sensor tip in the direction of the mounting unit, or extends only a nominal amount in said direction.

In an embodiment of the first aspect, the piercing element extends past the sensor tip in the direction of the mounting unit, but stops short of the electrode.

In an embodiment of the first aspect, the mounting unit comprises a guiding portion configured to guide insertion of the sensor unit through the host's skin and to support a column strength of the sensor body such that the sensor unit is capable of being inserted through the host's skin without substantial buckling.

In an embodiment of the first aspect, the at least one electrode comprises a working electrode and a reference electrode.

In an embodiment of the first aspect, the sensor body further comprises a support member configured to protect the membrane from damage during insertion of the sensor unit.

In an embodiment of the first aspect, the at least one electrode is the support member.

In an embodiment of the first aspect, the support member is configured to support at least a portion of the at least one electrode.

In an embodiment of the first aspect, the support member is configured to substantially surround the at least one electrode.

In an embodiment of the first aspect, the mounting unit comprises a sensor electronics unit operatively and detachably connected to the sensor body.

In an embodiment of the first aspect, the sensor electronics unit is configured to be located over a sensor insertion site.

Also in recognition of the foregoing problem, in a second aspect certain of the present embodiments comprise a method of making a sensor device, the method comprising: dipping a tip of a sensor into a liquid to form a coating of the liquid on the sensor tip; and withdrawing the sensor tip from the liquid while controlling parameters of the withdrawal so that the coating forms a sharp point extending from the sensor tip, the sharp point being capable of piercing tissue.

In an embodiment of the second aspect, the parameters include at least one of a length (L) of the sensor that is wetted by the liquid, a viscosity of the liquid, and a withdrawal rate.

In an embodiment of the second aspect, L is in the range of 0.1-4 mm.

In an embodiment of the second aspect, L is 2-3 mm.

In an embodiment of the second aspect, the viscosity is below 100 cP.

In an embodiment of the second aspect, the withdrawal rate is 20-30 in/sec.

In an embodiment of the second aspect, the method further comprises curing the coating.

In an embodiment of the second aspect, the curing comprises UV (or heat) cross-linking, irradiating, drying, or heating.

In an embodiment of the second aspect, the method further comprises using a tip mold or draw-through fixture that clamps and cures in one step in order to form a sharp cone shape.

In an embodiment of the second aspect, the method further comprises applying a voltage to the coating while it is being cured.

In an embodiment of the second aspect, the method further comprises heating the coating and drawing it out like glass.

Another aspect of the present embodiments includes the realization that in some current methods for sensor insertion the sensor is received within the lumen of an insertion needle. The needle, which has greater column strength than the sensor, bears the frictional forces that occur during insertion. Once the sensor is in place in the tissue, the needle is removed. The need to remove the needle adds complexity to the insertion process, including the need to electrically connect the sensor to sensor electronics after insertion. Some of the present embodiments provide solutions to this problem.

In recognition of the foregoing problem, in a third aspect certain of the present embodiments comprise a sensor device for measuring an analyte concentration in a host, the sensor device comprising: a sensor unit comprising a sensor body, at least one electrode, and a membrane covering at least a portion of the at least one electrode; and a piercing element comprising a material that rapidly dissolves upon insertion into the host, the piercing element including a sharp tip capable of piercing tissue, and a lumen that receives the sensor unit.

In an embodiment of the third aspect, the sensor body has a blunt tip.

In an embodiment of the third aspect, the sensor unit is not secured to the piercing element.

In an embodiment of the third aspect, the sensor unit is secured to the piercing element.

In an embodiment of the third aspect, the material of the piercing element comprises a material that suppresses wounding.

In an embodiment of the third aspect, the material of the piercing element comprises a material that promotes rapid wound healing.

In an embodiment of the third aspect, the material of the piercing element comprises a material that induces osmotic pressure or oncotic pressure.

In an embodiment of the third aspect, the material of the piercing element comprises one or more drugs.

In an embodiment of the third aspect, the material of the piercing element comprises a vascular endothelial growth factor (VEGF).

In an embodiment of the third aspect, the material of the piercing element comprises at least one of a salt, a metallic salt, a sugar, a synthetic polymer, polylactic acid, polyglycolic acid, or a polyphosphazene.

In an embodiment of the third aspect, the material of the piercing element biodegrades/dissolves within a first day after insertion into the host.

In an embodiment of the third aspect, the material of the piercing element biodegrades/dissolves within three hours after insertion into the host.

Another aspect of the present embodiments includes the realization that the material of analyte sensor membranes is soft, and tends to peel back as the sensor advances into tissue. This problem is especially acute for sensors that are formed by a process in which they are first coated with a membrane and then sharpened at the tip. This process exposes the sensor body, and leaves a thin coating of the membrane surrounding the sides of the sensor body at the tip. Some of the present embodiments provide solutions to this problem.

In recognition of the foregoing problem, in a fourth aspect certain of the present embodiments comprise a sensor device for measuring an analyte concentration in a host, the sensor device comprising: a sensor unit comprising a sensor body, at least one electrode, and a membrane covering at least a portion of the at least one electrode; and a mounting unit spaced from the sensor tip and configured to support the sensor device on an exterior surface of the host's skin; wherein the membrane comprises a hardening agent, the hardening agent providing increased column strength to the sensor unit so that the sensor unit is capable of being inserted through the host's skin without substantial buckling.

In an embodiment of the fourth aspect, the hardening agent is integrated with the membrane.

In an embodiment of the fourth aspect, the membrane covers a tip of the sensor body.

In an embodiment of the fourth aspect, a tip of the sensor body is exposed through the membrane.

In an embodiment of the fourth aspect, the exposed tip of the sensor body comprises a material that does not react with hydrogen peroxide.

In an embodiment of the fourth aspect, the hardening agent comprises cyanoacrylate.

Also in recognition of the foregoing problem, in a fifth aspect certain of the present embodiments comprise a sensor device for measuring an analyte concentration in a host, the sensor device comprising: a sensor unit comprising a sensor body, at least one electrode, and a membrane covering at least a portion of the at least one electrode; and a mounting unit spaced from the sensor tip and configured to support the sensor device on an exterior surface of the host's skin; wherein the membrane comprises a hardening agent, the hardening agent increasing a column strength of the sensor unit and increasing an adhesion of the membrane to the at least one electrode; and wherein the membrane comprising the hardening agent allows analyte permeability.

In an embodiment of the fifth aspect, the hardening agent is suspended in a matrix.

In an embodiment of the fifth aspect, the membrane covers a tip of the sensor.

In an embodiment of the fifth aspect, a tip of the sensor is exposed through the membrane.

In an embodiment of the fifth aspect, the exposed tip of the sensor comprises a material that does not react with hydrogen peroxide.

In an embodiment of the fifth aspect, the hardening agent comprises cyanoacrylate.

Also in recognition of the foregoing problem, in a sixth aspect certain of the present embodiments comprise a method of making a sensor device, the method comprising: coating a wire with a membrane; cutting the coated wire to a desired length to thereby form a sensor tip; and exposing the coated wire to a hardening agent such that the membrane absorbs the hardening agent.

In an embodiment of the sixth aspect, exposing the coated wire comprises dipping at least the sensor tip in the hardening agent.

In an embodiment of the sixth aspect, certain of the present embodiments further comprise curing the membrane to harden the hardening agent.

In an embodiment of the sixth aspect, certain of the present embodiments further comprise sharpening the sensor tip to form a sharp point capable of piercing tissue.

In an embodiment of the sixth aspect, the sensor tip comprises a material that does not react with hydrogen peroxide.

In an embodiment of the sixth aspect, certain of the present embodiments further comprise applying a deadening agent to the sharpened sensor tip to deaden any active surfaces exposed during the sharpening step.

In an embodiment of the sixth aspect, the deadening agent comprises cyanoacrylate or silane.

In an embodiment of the sixth aspect, the deadening agent is applied using vapor deposition.

In an embodiment of the sixth aspect, the hardening agent comprises cyanoacrylate.

Also in recognition of the foregoing problem, in a seventh aspect certain of the present embodiments comprise a method of making a sensor device, the method comprising: cutting a wire to a desired length to thereby form a sensor tip; sharpening the sensor tip to form a sharp point capable of piercing tissue; coating the wire, including the sharpened sensor tip, with a membrane; and exposing the coated wire to a hardening agent such that the membrane absorbs the hardening agent.

In an embodiment of the seventh aspect, exposing the coated wire comprises dipping at least the sensor tip in the hardening agent.

In an embodiment of the seventh aspect, certain of the present embodiments further comprise curing the membrane to harden the hardening agent.

In an embodiment of the seventh aspect, the hardening agent comprises cyanoacrylate.

In recognition of any of the problems described herein, in an eighth aspect certain of the present embodiments comprise a sensor device for measuring an analyte concentration in a host. The sensor device is configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor body comprises a stimulus-responsive material that changes at least one material property responsive to a stimulus.

In an embodiment of the eighth aspect, the at least one material property is at least one of hardness, shape, permeability, relative hydrophilicity, modulus of elasticity, or conformation of polymer orientation.

In an embodiment of the eighth aspect, the sensor body is hard ex vivo and soft in vivo.

In an embodiment of the eighth aspect, the stimulus that induces the change in the at least one material property is at least one of temperature, hydration, radiation, electrical stimulus, or a magnetic field.

In an embodiment of the eighth aspect, the sensor body is a polymer

In an embodiment of the eighth aspect, the sensor body is polyurethane, polyester, polyamide, polyacrylate, or polyether, or copolymers thereof.

In an embodiment of the eighth aspect, the stimulus-responsive material is a shape memory metal.

In an embodiment of the eighth aspect, the shape memory metal is copper-aluminum-nickel (Cu—Al—Ni), nickel-titanium (NiTi), iron-manganese-silicon (Fe—Mn—Si), or copper-zinc-aluminum (Cu—Zn—Al).

In an embodiment of the eighth aspect, the sensor body defines a first shape prior to insertion into the host's skin.

In an embodiment of the eighth aspect, the sensor body defines a memorized shape, and the sensor body returns to the memorized shape after insertion into the host's skin.

In an embodiment of the eighth aspect, the first shape is curved or straight, and the memorized shape is curved or straight.

In an embodiment of the eighth aspect, when the sensor body returns to the memorized shape stored spring energy is released from the sensor body.

In an embodiment of the eighth aspect, the released spring energy creates a whipping action that facilitates piercing the host's skin.

Another aspect of the present embodiments includes the realization that the materials used to form the membranes of analyte sensors are often soft, and thus tend to delaminate (i.e., peel back and sometimes peel off) as the sensor advances into skin and/or tissue. This problem is especially acute for sensors formed by a process in which the sensors are first coated with a membrane and then sharpened at the tip. This process exposes the sensor body, and leaves a thin coating of the membrane surrounding the sides of the sensor body at the tip. Some of the present embodiments provide solutions to this problem, including how to form the tip after applying the membrane, without damaging the tip, and while still maintaining the integrity of the tip.

In recognition of the foregoing problem, in a ninth aspect certain of the present embodiments comprise a method of making a sensor device configured for implantation in a host without use of an inserter. The method comprises forming a piercing tip on a sensor unit, the sensor unit including a sensor body, at least one electrode, and a membrane covering at least a portion of the at least one electrode. The membrane is applied to the sensor unit prior to forming the piercing tip on the sensor unit.

In an embodiment of the ninth aspect, the method further comprises applying the membrane to the sensor unit.

In an embodiment of the ninth aspect, forming the piercing tip comprises forming an annular channel about a circumference of a wire that is coated with the membrane.

In an embodiment of the ninth aspect, the annular channel extends through the membrane and partially into the wire In an embodiment of the ninth aspect, the method further comprises applying tension to the coated wire.

In an embodiment of the ninth aspect, the tension induces strain in the wire proximate the annular channel, causing the wire to neck and fracture.

In an embodiment of the ninth aspect, the necking forms the piercing tip on the sensor body.

In an embodiment of the ninth aspect, the method further comprises covering the piercing tip with a protective outer layer.

In an embodiment of the ninth aspect, forming the piercing tip comprises selectively removing portions of a membrane coating from wire stock.

In an embodiment of the ninth aspect, the wire stock is wound on a reel.

In an embodiment of the ninth aspect, the method further comprises singulating the wire stock at spaced locations to form a plurality of membrane-coated sensor wires.

In an embodiment of the ninth aspect, forming the piercing tip comprises exposing a distal end surface of the sensor body.

In an embodiment of the ninth aspect, the method further comprises applying a coating over the distal end of the sensor body.

In an embodiment of the ninth aspect, the coating renders the exposed distal end surface of the sensor body non-electroactive.

In an embodiment of the ninth aspect, forming the piercing tip comprises applying an end cap to a distal end of a membrane-coated sensor wire.

In an embodiment of the ninth aspect, the end cap includes the piercing tip.

In an embodiment of the ninth aspect, forming the piercing tip comprises applying a plurality of membrane layers to the sensor body.

In an embodiment of the ninth aspect, forming the piercing tip further comprises applying a rigid coating at a distal end of the sensor body over the plurality of membrane layers.

In an embodiment of the ninth aspect, forming the piercing tip further comprises shaping the rigid coating to produce the piercing tip.

In an embodiment of the ninth aspect, the method further comprises applying the membrane to the sensor body.

In an embodiment of the ninth aspect, the method further comprises applying the piercing tip to a distal end of the sensor body.

In an embodiment of the ninth aspect, the piercing tip is secured to the distal end of the sensor body by mechanical crimping, press fitting, welding, shrink tubing, or heating.

In an embodiment of the ninth aspect, the method further comprises applying a retractable introducer sheath around the sensor body.

In an embodiment of the ninth aspect, forming the piercing tip comprises applying the piercing tip to a distal end of the sensor body over the membrane.

In an embodiment of the ninth aspect, the piercing tip comprises a material that is biodegradable and/or bioabsorbable.

In an embodiment of the ninth aspect, the piercing tip material comprises polyvinylpyrrolidone (PVP), polyvinyl alcohol (PVA), or maltose.

In an embodiment of the ninth aspect, applying the piercing tip to a distal end of the sensor body over the membrane comprises casting the piercing tip onto the distal end of the sensor body and over the membrane using a mold.

In an embodiment of the ninth aspect, applying the piercing tip to a distal end of the sensor body over the membrane comprises injection molding or insert molding.

In an embodiment of the ninth aspect, applying the piercing tip to a distal end of the sensor body over the membrane comprises inserting a distal end of the sensor body into an open proximal end of the piercing tip.

In an embodiment of the ninth aspect, the method further comprises crimping the proximal end of the piercing tip.

In an embodiment of the ninth aspect, applying the piercing tip to a distal end of the sensor body over the membrane comprises overmolding the piercing tip to the distal end of the sensor body and over the membrane.

Another aspect of the present embodiments includes the realization that applying a membrane to a sharp sensor tip presents challenges. For example, the sharp tip can breach the membrane and/or cause the membrane to delaminate, particularly when the sensor is subjected to frictional forces during the process of sensor insertion. Also, applying a membrane to a sharp sensor tip may dull the tip, rendering the tip less effective for direct press insertion of the sensor. Some of the present embodiments provide solutions to these problems, including how to apply the membrane to a sharp tip, without damaging the tip, and while maintaining the integrity of the tip.

In recognition of the foregoing problem, in a tenth aspect certain of the present embodiments comprise a method of making a sensor device configured for implantation in a host without use of an inserter. The method comprises forming a piercing tip on a sensor unit, the sensor unit including a sensor body, at least one electrode, and a membrane covering at least a portion of the at least one electrode. The piercing tip is formed on the sensor unit prior to applying the membrane to the sensor unit.

In an embodiment of the tenth aspect, forming the piercing tip comprises dipping the sensor body in a membrane solution to form the membrane on the sensor body.

In an embodiment of the tenth aspect, forming the piercing tip further comprises, after the membrane solution dries, removing a portion of the membrane at a distal end of the sensor body to expose the distal end of the sensor body.

In an embodiment of the tenth aspect, removing the portion of the membrane at the distal end of the sensor body comprises laser ablation, electropolishing, bead blasting, dry ice blasting, or burning.

In an embodiment of the tenth aspect, the method further comprises applying a protective layer over the distal end of the sensor body.

In an embodiment of the tenth aspect, forming the piercing tip further comprises removing a portion of the membrane solution, prior to the membrane solution drying, at a distal end of the sensor body.

In an embodiment of the tenth aspect, removing the portion of the membrane solution comprises blotting or wiping the distal end of the sensor body.

In an embodiment of the tenth aspect, the method further comprises applying the membrane to the sensor body and the piercing tip.

In an embodiment of the tenth aspect, the method further comprises applying a coating to the piercing tip.

In an embodiment of the tenth aspect, the method further comprises applying a retractable introducer sheath around the sensor body.

In an embodiment of the tenth aspect, an outer diameter of the introducer sheath is substantially equal to, or less than, a diameter of the piercing tip at a proximal end thereof.

In an embodiment of the tenth aspect, the sensor body includes a core and an outer layer.

In an embodiment of the tenth aspect, the membrane is applied over the outer layer, but not over the core.

In an embodiment of the tenth aspect, the core and the outer layer comprise different materials.

In an embodiment of the tenth aspect, the core comprises a material that repels the membrane.

In an embodiment of the tenth aspect, the material of the core has a low surface energy.

In an embodiment of the tenth aspect, the material of the core is non-wetting.

In an embodiment of the tenth aspect, forming the piercing tip comprises electrochemical grinding.

In an embodiment of the tenth aspect, the membrane comprises a plurality of layers.

In an embodiment of the tenth aspect, a thickness of each layer is in a range from about 0.5 microns to about 10 microns.

In an embodiment of the tenth aspect, a thickness of at least one of the layers is less than a thickness of at least another one of the layers.

In an embodiment of the tenth aspect, the method further comprises applying the membrane to the sensor body and the piercing tip.

In an embodiment of the tenth aspect, the method further comprises removing the membrane from the piercing tip, but not from the sensor body.

In an embodiment of the tenth aspect, removing the membrane from the piercing tip comprises chemical etching, laser ablation, or mechanical stripping.

In an embodiment of the tenth aspect, the method further comprises applying the membrane to the sensor body and the piercing tip by dipping in a membrane solution.

In an embodiment of the tenth aspect, the method further comprises dipping the piercing tip in a solvent to dissolve the membrane and substantially remove the membrane from the piercing tip.

In an embodiment of the tenth aspect, the method further comprises dipping the piercing tip in a release agent that prevents the membrane from adhering to the piercing tip.

In an embodiment of the tenth aspect, forming the piercing tip comprises coating the piercing tip with a sacrificial material.

In an embodiment of the tenth aspect, the method further comprises applying the membrane to the sensor body and the piercing tip.

In an embodiment of the tenth aspect, the method further comprises treating the piercing tip to break down the sacrificial layer and remove the membrane from the piercing tip.

In an embodiment of the tenth aspect, the sacrificial material is light sensitive, heat sensitive, or soluble, and treating the piercing tip comprises applying light, applying heat, or applying a solvent.

In an embodiment of the tenth aspect, the method further comprises applying the membrane to the piercing tip by dipping the piercing tip in a membrane solution with the piercing tip pointed downward, and subsequently inverting the sensor unit, before the solution dries, such that piercing tip is pointed upward.

In an embodiment of the tenth aspect, the method further comprises applying the membrane to the sensor body by dipping the sensor body in a membrane solution with the piercing tip pointed upward, such that the sensor body is only partially submerged in the membrane solution and the membrane solution never contacts the piercing tip.

In an embodiment of the tenth aspect, the method further comprises removing an annular band of material from the sensor body just proximal of the piercing tip to form an annular channel, wherein a distal end of the channel defines an edge.

In an embodiment of the tenth aspect, the method further comprises dipping the sensor body and the piercing tip in a membrane solution.

In an embodiment of the tenth aspect, the edge causes a liquid meniscus of the membrane solution to break off, thereby leaving the piercing tip uncovered by the membrane.

In an embodiment of the tenth aspect, the sensor body includes a core and an outer layer.

In an embodiment of the tenth aspect, the method further comprises removing a first portion of the outer layer and a second portion of the outer layer to expose the core.

In an embodiment of the tenth aspect, the first portion of the outer layer is located adjacent the piercing tip, and the second portion of the outer layer is located proximal of the piercing tip.

In an embodiment of the tenth aspect, the method further comprises removing a portion of the core to form the piercing tip.

In an embodiment of the tenth aspect, the method further comprises attaching a cap over the piercing tip.

In an embodiment of the tenth aspect, the attached cap includes a sharp distal end.

In an embodiment of the tenth aspect, the attached cap comprises an absorbable material such that the cap is absorbed into a body of the host after the sensor body is inserted into skin and/or tissue of the host.

In an embodiment of the tenth aspect, the sensor body includes a planar, flexible printed circuit board (PCB) embedded in an outer core.

In an embodiment of the tenth aspect, the method further comprises removing a section of the outer core proximal of the piercing tip to form a window.

In an embodiment of the tenth aspect, removing the section of the outer core comprises laser ablation.

In an embodiment of the tenth aspect, an outer surface of the PCB in an area of the window includes a platinum layer that resists the laser ablation.

In an embodiment of the tenth aspect, the method further comprises dipping the sensor body in a membrane solution to form the membrane within the window.

In an embodiment of the tenth aspect, the sensor body includes a thin, flat microelectromechanical systems (MEMS) substrate.

In an embodiment of the tenth aspect, the substrate includes the piercing tip.

In an embodiment of the tenth aspect, the method further comprises forming the membrane on the substrate.

Another aspect of the present embodiments includes the realization that forming a sharp distal tip on a sensor presents challenges, such as contaminating the membrane surface and/or damaging the membrane so that it cannot perform its proper function. Contamination of the membrane can alter membrane properties such as diffusion. For example, a contaminant may reduce the permeability characteristics (e.g., permselectivity) of the membrane. Damage to the membrane can also affect the functionality of the sensor. For example, if membrane removal extends beyond the distal tip to a portion intended to cover the electroactive surface that forms an electrode, the sensor can become defective, as diffusion properties of the sensor become substantially altered and uncontrolled. On the other hand, if excess membrane material is present at the distal tip of the sensor, the distal tip of the sensor may become dull, such that it becomes less effective for piercing skin and/or tissue. Some of the present embodiments provide solutions to these problems, including how to form a sharp distal tip by removing material from the tip and how to form a sharp distal tip by adding material to the tip. Another aspect of the present embodiments includes the realization that a piercing tip can be formed on sensors during a step of singulating a sensor wire into individual sensors. For example, singulating processes may include, without limitation, mechanical pressing, hot pressing, laser ablation, extruding, milling, etc. By forming a piercing tip during singulation, a sharp distal tip can be formed prior to applying the membrane to the sensor, thereby avoiding cross-contamination and damaging the delicate membrane with a subsequent tip-forming step.

In recognition of the foregoing problems, in a eleventh aspect certain of the present embodiments comprise a method of making a sensor device configured for implantation in a host without use of an inserter. The method comprises forming a piercing tip on a sensor unit, the sensor unit including a sensor body, at least one electrode, and a membrane covering at least a portion of the at least one electrode. Forming the piercing tip comprises removing material from the sensor body.

In an embodiment of the eleventh aspect, forming the piercing tip comprises singulating wire stock while exposing the wire stock to cyanoacrylate vapor.

In an embodiment of the eleventh aspect, the method includes reel-to-reel continuous processing.

In an embodiment of the eleventh aspect, forming the piercing tip comprises dipping a distal end of the sensor body.

In an embodiment of the eleventh aspect, dipping the distal end of the sensor body comprises dipping in an etchant or a polishing solution.

In an embodiment of the eleventh aspect, forming the piercing tip comprises electropolishing.

In an embodiment of the eleventh aspect, forming the piercing tip comprises moving the sensor body relative to an abrasive surface with the sensor body forming an angle $\theta$ relative to the abrasive surface.

In an embodiment of the eleventh aspect, $\Theta$ is between 0° and 90°.

In an embodiment of the eleventh aspect, $\Theta$ is about 5°, or about 10°, or about 150.

In an embodiment of the eleventh aspect, the sensor body is held within a support fixture that is moved relative to the abrasive surface.

In an embodiment of the eleventh aspect, the sensor body includes an inner core and an outer layer, and forming the piercing tip comprises removing a portion of the outer layer at a distal end of the sensor body to expose a portion of the inner core.

In an embodiment of the eleventh aspect, removing the portion of the outer layer comprises mechanical stripping, laser ablation, bead blasting, abrasion, or chemical etching.

In an embodiment of the eleventh aspect, forming the piercing tip comprises applying tension to a sensor wire along a longitudinal axis of the sensor wire.

In an embodiment of the eleventh aspect, the applied tension causes the sensor wire to neck in an intermediate region.

In an embodiment of the eleventh aspect, the applied tension further causes the sensor wire to fail in the intermediate region.

In an embodiment of the eleventh aspect, the method further comprises applying heat to the sensor wire in the intermediate region, wherein the heat is applied simultaneously with the tension.

In an embodiment of the eleventh aspect, the heat is applied with a resistive heating element.

In an embodiment of the eleventh aspect, forming the piercing tip comprises positioning a sensor wire between opposing cutting blades and singulating the sensor wire into at least two pieces.

In an embodiment of the eleventh aspect, a cutting edge defined by converging surfaces of one of the cutting blades defines an angle between 30 degrees and 145 degrees.

In an embodiment of the eleventh aspect, the angle is not a right angle.

Also in recognition of the foregoing problems, in a twelfth aspect certain of the present embodiments comprise a method of making a sensor device configured for implantation in a host without use of an inserter. The method comprises forming a piercing tip on a sensor unit, the sensor unit including a sensor body, at least one electrode, and a membrane covering at least a portion of the at least one electrode. Forming the piercing tip comprises adding material to the sensor body.

In an embodiment of the twelfth aspect, forming the piercing tip comprises dipping the sensor body in a bath of a polymer material.

In an embodiment of the twelfth aspect, the method further comprises removing the sensor body from the bath and applying a voltage across the polymer material, thereby causing the polymer material to elongate and form the piercing tip.

In an embodiment of the twelfth aspect, the method comprises electrospinning.

In an embodiment of the twelfth aspect, forming the piercing tip comprises dipping the sensor body in a bath and withdrawing the sensor body from the bath, and as the sensor body is withdrawn a dip coating on the sensor body cures to form the piercing tip.

In recognition of any of the problems described herein, in a thirteenth aspect certain of the present embodiments comprise a sensor device for measuring an analyte concentration in a host, the sensor device being configured for implantation in the host without use of an inserter. The sensor device comprises a conductive core wire. The sensor device further comprises a nonconductive jacket disposed over at least a portion of the core wire. The sensor device further comprises at least one electrode disposed over the jacket and electrically connected to the core wire. The at least one electrode is formed by printing.

In an embodiment of the thirteenth aspect, the at least one electrode comprises a first electrode, a second electrode, and a third electrode, and the electrodes are axially spaced along the sensor device.

In an embodiment of the thirteenth aspect, the second electrode does not extend around the entire circumference of the jacket.

In an embodiment of the thirteenth aspect, the sensor device further comprises a conductive trace extending along the jacket between the first and third electrodes.

In an embodiment of the thirteenth aspect, the sensor device further comprises an insulator overlying at least a portion of the conductive trace.

In an embodiment of the thirteenth aspect, a distal end of the sensor device includes a piercing tip.

In an embodiment of the thirteenth aspect, a distal end of the sensor device is non-electroactive.

In recognition of any of the problems described herein, in a fourteenth aspect certain of the present embodiments comprise a sensor device for measuring an analyte concentration in a host, the sensor device being configured for implantation in the host without use of an inserter. The sensor device comprises a nonconductive core wire. The sensor device further comprises at least one electrode disposed over the core wire. The sensor device further comprises at least one conductive trace extending from the at least one electrode along the core wire. The at least one electrode is formed by printing.

In an embodiment of the fourteenth aspect, the at least one electrode comprises a first electrode, a second electrode, and a third electrode, and the electrodes are axially spaced along the sensor device.

In an embodiment of the fourteenth aspect, the first and second electrodes do not extend around the entire circumference of the core wire.

In an embodiment of the fourteenth aspect, a distal end of the sensor device includes a piercing tip.

In an embodiment of the fourteenth aspect, the at least one electrode is printed on the core wire with a platinum paste.

In recognition of any of the problems described herein, in a fifteenth aspect certain of the present embodiments comprise a sensor device for measuring an analyte concentration in a host, the sensor device being configured for implantation in the host without use of an inserter. The sensor device comprises a sensor body shaped as a flat sheet rolled into a cylinder.

In an embodiment of the fifteenth aspect, the cylinder includes an overlap region where opposite edges of the flat sheet converge.

In an embodiment of the fifteenth aspect, overlapping portions of the opposite edges are secured to one another.

In an embodiment of the fifteenth aspect, the overlapping portions are secured to one another with an adhesive.

In an embodiment of the fifteenth aspect, the adhesive dissolves after the sensor device is implanted in the host.

In an embodiment of the fifteenth aspect, upon dissolution of the adhesive, the rolled sensor body unrolls to reassume its flat shape.

In recognition of any of the problems described herein, in a sixteenth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises a retractable introducer sheath configured to cover at least a portion of the membrane during insertion of the sensor device.

In an embodiment of the sixteenth aspect, a proximal end of the tissue piercing element has a diameter greater than a diameter of the sensor body.

In an embodiment of the sixteenth aspect, a diameter of the introducer sheath is substantially equal to or less than the diameter of the proximal end of the tissue piercing element.

In recognition of any of the problems described herein, in a seventeenth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor body includes a cross-section that defines at least one trough that extends along a length of the sensor body.

In an embodiment of the seventeenth aspect, the cross-section of the sensor body defines a plus sign with four evenly spaced troughs.

In an embodiment of the seventeenth aspect, the cross-section of the sensor body defines a circle with a single trough.

In an embodiment of the seventeenth aspect, the at least one electrode is located in the at least one trough.

In an embodiment of the seventeenth aspect, the at least one electrode and the at least one membrane are flush with or recessed beneath an outer perimeter of the sensor body.

In recognition of any of the problems described herein, in an eighteenth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises a retractable introducer sheath configured to cover at least a portion of the membrane during insertion of the sensor device.

In recognition of any of the problems described herein, in a nineteenth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises at least one through hole extending through the sensor body.

In an embodiment of the nineteenth aspect, the membrane is disposed within the at least one through hole.

In recognition of any of the problems described herein, in a twentieth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor body includes a plurality of depressions.

In an embodiment of the twentieth aspect, the membrane is disposed within at least one of the depressions.

In an embodiment of the twentieth aspect, the membrane is flush with an outer surface of the sensor body, or recessed beneath the outer surface of the sensor body.

In an embodiment of the twentieth aspect, the depressions are randomly arranged.

In recognition of any of the problems described herein, in a twenty-first aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises a plurality of axially spaced depressions in the sensor body.

In an embodiment of the twenty-first aspect, the membrane is disposed within the depressions.

In an embodiment of the twenty-first aspect, the sensor device further comprises an outer layer of a material that is permeable to one or more selected analytes.

In recognition of any of the problems described herein, in a twenty-second aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises a protective outer layer disposed over the sensor body and the membrane.

In an embodiment of the twenty-second aspect, the protective outer layer comprises a material that dissolves upon insertion into skin and/or tissue of the host.

In an embodiment of the twenty-second aspect, the material of the protective outer layer comprises polyvinyl-pyrrolidone (PVP).

In recognition of any of the problems described herein, in a twenty-third aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor device further comprises an outer layer of a rigid material.

In an embodiment of the twenty-third aspect, the outer layer covers substantially all of the sensor body, but includes at least one window.

In an embodiment of the twenty-third aspect, the window is located over the at least one electrode such that the at least one electrode is exposed for contact with tissue and/or bodily fluids of the host.

In an embodiment of the twenty-third aspect, the outer layer comprises cyanoacrylate.

In recognition of any of the problems described herein, in a twenty-fourth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. The sensor body comprises a conductive wire and an outer coating disposed over the wire, and the outer coating has a greater thickness than the wire.

In an embodiment of the twenty-fourth aspect, the outer coating includes at least one window corresponding to a location of the at least one electrode.

In an embodiment of the twenty-fourth aspect, the membrane is disposed within the window.

In an embodiment of the twenty-fourth aspect, the membrane is recessed beneath an outer surface of the outer coating.

In an embodiment of the twenty-fourth aspect, the sensor device further comprises a highly permeable outer layer.

In an embodiment of the twenty-fourth aspect, the outer layer comprises a hydrogel.

In recognition of any of the problems described herein, in a twenty-fifth aspect certain of the present embodiments comprise a sensor device for measuring an analyte concentration in a host, the sensor device being configured for implantation in the host without use of an inserter. The sensor device comprises a sensor unit comprising a sensor body, at least one electrode, and a membrane covering at least a portion of the at least one electrode. The sensor device further comprises a piercing element at a distal end of the sensor unit, the piercing element being configured for piercing skin and/or tissue of the host. The sensor device further comprises a mounting unit spaced from the sensor tip and configured to support the sensor device on an exterior surface of the host's skin. Membrane is applied to the sensor body by printing.

In an embodiment of the twenty-fifth aspect, the sensor body comprises polytetrafluoroethylene (PTFE).

BRIEF DESCRIPTION OF THE DRAWINGS

The various present embodiments now will be discussed in detail with an emphasis on highlighting the advantageous features. These embodiments depict the novel and non-obvious sensors for continuous analyte monitoring, and related methods, shown in the accompanying drawings, which are for illustrative purposes only. The figures are not necessarily drawn to scale, and they are provided merely to illustrate the present embodiments. These drawings include the following figures, in which like numerals indicate like parts:

FIG. 34 is a schematic side elevation view of another process for making a sensor configured for direct press insertion according to the present embodiments;

FIGS. 35-37 are schematic cross-sectional side elevation views of another process for making a sensor configured for direct press insertion according to the present embodiments;

FIG. 52 is a schematic side elevation view of another process for making a sensor configured for direct press insertion according to the present embodiments;

FIG. 52A is a schematic cross-sectional side elevation view of another process for making a sensor configured for direct press insertion according to the present embodiments;

FIG. 53 is a schematic side elevation view of another process for making a sensor configured for direct press insertion according to the present embodiments;

FIG. 54 is a schematic side elevation view of another process for making a sensor configured for direct press insertion according to the present embodiments;

FIG. 54A is a detail view of the portion of FIG. 54 indicated by the circle 54A-54A in FIG. 54;

FIG. 60 is a schematic side elevation view of another process for making a sensor configured for direct press insertion according to the present embodiments;

FIGS. 61 and 62 are schematic side elevation views of another process for making a sensor configured for direct press insertion according to the present embodiments;

FIG. 68 is a schematic side elevation view of another process for making a sensor configured for direct press insertion according to the present embodiments;

FIG. 69 is a schematic side elevation view of another process for making a sensor configured for direct press insertion according to the present embodiments;

FIG. 70 is a schematic side elevation view of another process for making a sensor configured for direct press insertion according to the present embodiments;

FIG. 71 is a schematic side elevation view of another process for making a sensor configured for direct press insertion according to the present embodiments;

DETAILED DESCRIPTION

Figure 1:
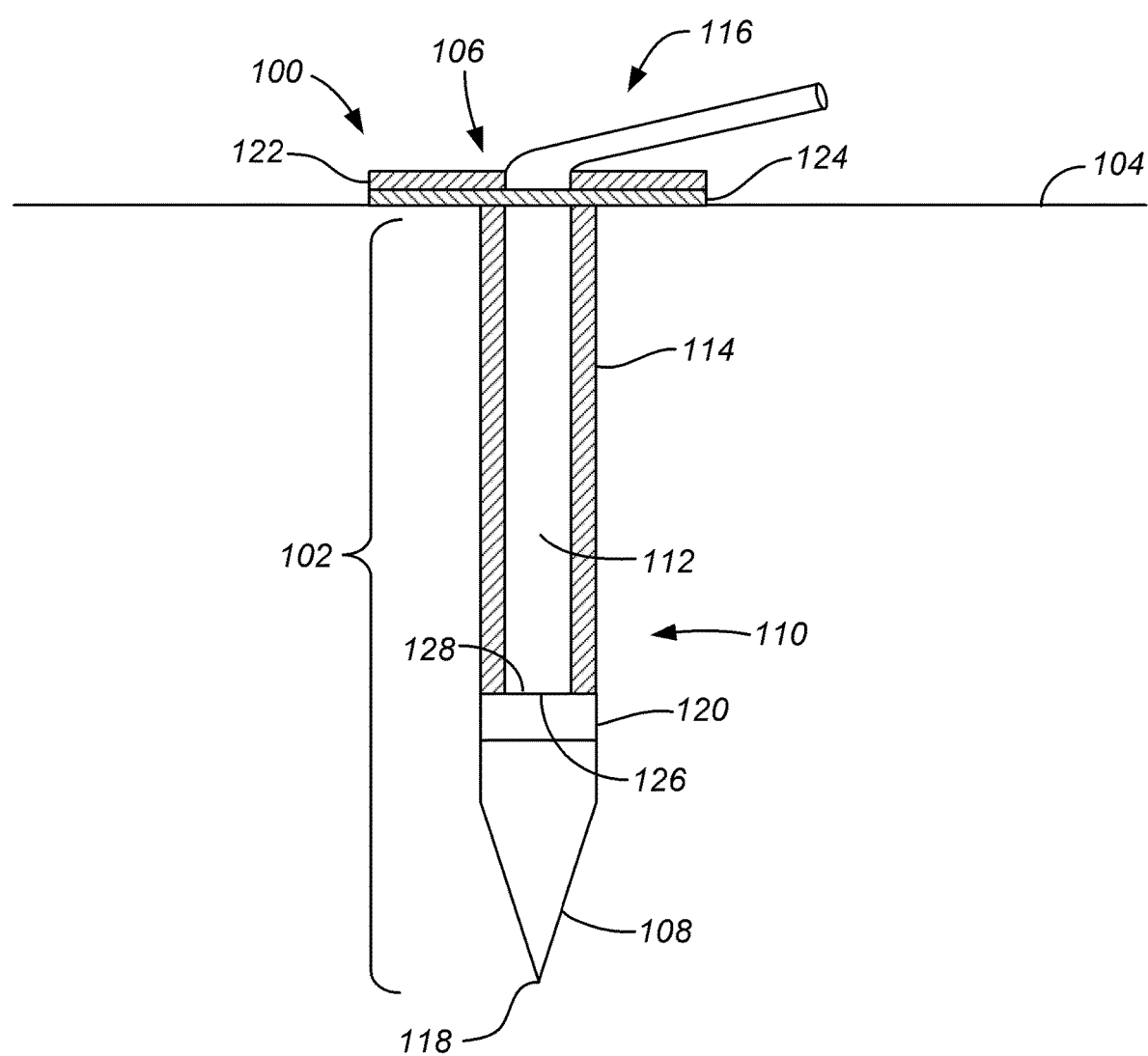
FIG. 1 is a schematic cross-sectional view of a continuous analyte sensor according to the present embodiments.

The following detailed description describes the present embodiments with reference to the drawings. In the drawings, reference numbers label elements of the present embodiments. These reference numbers are reproduced below in connection with the discussion of the corresponding drawing features.

The drawings and their descriptions may indicate sizes, shapes and configurations of the various components. Such depictions and descriptions should not be interpreted as limiting. Alternative sizes, shapes and configurations are also contemplated as within the scope of the present embodiments. Also, the drawings, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

Overview

The embodiments described herein provide various mechanisms for directly inserting a transcutaneous sensor into a host without the use of a separate applicator, i.e., other than the sensor device itself. Direct press insertion of a transcutaneous sensor (e.g., an electrode) having a wire-like geometry, especially a fine wire, may be technically challenging because of buckling risks associated with the sensor. Direct press insertion of a sensor also presents challenges relating to damage during the insertion process to the membrane disposed on the sensor. Without membrane protection, the membrane may be stripped off the sensor or be mechanically damaged during the insertion process. It is also desirable to avoid having exposed metal (or other electrically conductive material) at the tip of the sensor, because exposed metal may be electroactive and add background signal (noise) and/or cause the sensitivity of the sensor to vary. The embodiments described herein are designed to overcome the aforementioned challenges by providing miniaturized sensor devices capable of providing structural support (e.g., in the form of mechanical/structural properties such as column strength) for direct insertion of a transcutaneous sensor, and capable of protecting the membrane from damage during the insertion process.

FIG. 1 illustrates a schematic side view of one embodiment of a transcutaneous sensor device 100 configured to continuously measure analyte concentration (e.g., glucose concentration) in a host to provide a data stream representative of the host's analyte concentration, in accordance with the present embodiments. Sensors such as the one illustrated in FIG. 1 are sometimes referred to as "tack" sensors, due to their resemblance to a thumbtack.

In the particular embodiment illustrated in FIG. 1, the sensor device 100 comprises an in vivo portion 102 (also referred to as a sensor unit) configured for insertion under the host's skin 104, and an ex vivo portion 106 configured to remain above the host's skin surface after sensor insertion. The in vivo portion 102 comprises a tissue-piercing element 108 configured for piercing the host's skin 104, and a sensor body 110. The sensor body 110 comprises a support member 112 including one or more electrodes, and a membrane 114 disposed over at least a portion of the support member 112. The support member 112 may also be referred to as a sensor body 112, and the two terms are used interchangeably herein.

The ex vivo portion 106 comprises a mounting unit 116 that may include a sensor electronics unit (not shown) embedded or detachably secured therein, or alternatively may be configured to operably connect to a separate sensor electronics unit. Further details regarding the sensor device 100 and its components may be found in U.S. Patent Application Publication No. 2011/0077490, the disclosure of which is incorporated herein in its entirety.

Tissue-Piercing Element

The tissue-piercing element 108 of the sensor device 100 is configured to pierce the host's skin 104, and to open and define a passage for insertion of the sensor body 110 into a tissue of the host. In some embodiments, the tissue-piercing element 108 may be integral with the support member 112. In other embodiments, the tissue-piercing element 108 may be a discrete component. In such embodiments, the tissue-piercing element 108 may be secured to the support member 112, such as with an adhesive. Alternatively, the tissue-piercing element 108 may merely abut a blunt distal face of the support member 112 and/or the membrane 114. In such embodiments, an outer sleeve or band (not shown) may encircle a junction of the tissue-piercing element 108 and the support member 112/membrane 114.

The skin generally comprises multiple layers, including the epidermis, dermis, and subcutaneous layers. The epidermis comprises a number of layers within its structure including the stratum corneum, which is the outermost layer and is generally from about 10 to 20 microns thick, and the stratum germinativum, which is the deepest layer of the epidermis. While the epidermis generally does not contain blood vessels, it exchanges metabolites by diffusion to and from the dermis. While not wishing to be bound by theory, it is believed that because the stratum germinativum is supported by vascularization for survival, the interstitial fluid at the stratum germinativum sufficiently represents a host's analyte (e.g., glucose) levels. Beneath the epidermis is the dermis, which is from about 1 mm to about 3 mm thick and contains blood vessels, lymphatics, and nerves. The subcutaneous layer lies underneath the dermis and is mostly comprised of fat. The subcutaneous layer serves to insulate the body from temperature extremes. It also contains connective tissue and a small amount of blood vessels.

In some embodiments, the in vivo portion 102 of the sensor device 100 may have a length long enough to allow for at least a portion of the sensor body 110 to reside within the stratum germinativum. This may be desirable in some instances because the epidermis does not contain a substantial number of blood vessels or nerve endings. Thus, sensor insertion may be relatively painless, and the host may not experience much bleeding or discomfort from the insertion. In some of these embodiments, the in vivo portion 102 of the sensor device 100 may have a length of from about 0.1 mm to about 1.5 mm, or from about 0.2 mm to about 0.5 mm. In other embodiments, the in vivo portion 102 of the sensor device 100 may have a length that allows for at least a portion of the sensor body 110 to reside in the dermis layer. This may be desirable in some instances because the dermis is well vascularized, as compared to the subcutaneous layer, and thus may provide sufficient analytes (e.g., glucose) for measurement and reduce measurement lags associated with changes of analyte concentrations of a host, such as those that occur after meals. The metabolically active tissue near the outer dermis (and also the stratum germinativum) provides rapid equilibrium of the interstitial fluid with blood. In some of these embodiments, the in vivo portion 102 of the sensor device may have a length of from about 1 mm to about 7 mm, or from about 2 mm to about 6 mm. In still other embodiments, the in vivo portion 102 of the sensor device 100 may have a length that allows for at least a portion of the sensor body 110 to reside in the subcutaneous layer. While not wishing to be bound by theory, it is believed that because the subcutaneous layer serves to insulate the body from temperature extremes, the subcutaneous layer may reduce variations of analyte concentration readings associated with temperature fluctuations. In some of these embodiments, the in vivo portion 102 of the sensor device may have a length of from about 3 mm to about 10 mm, or from about 5 mm to about 7 mm.

Figure 2A:
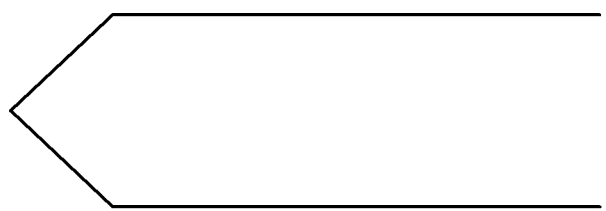
FIGS. 2A-2H are schematic side views of example shapes of tissue-piercing tips for a continuous analyte sensor according to the present embodiments.
Figure 2B:
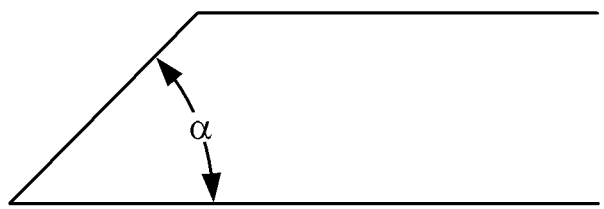
Figure 2C:
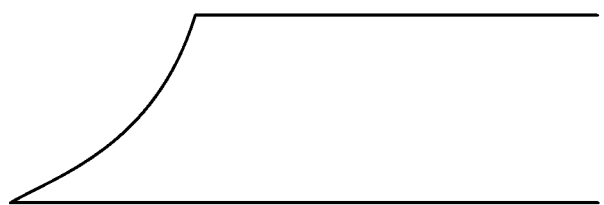
Figure 2D:
Figure 2E:
Figure 2F:
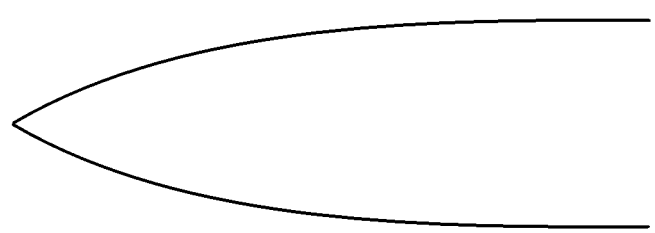
Figure 2G:
Figure 2H:

The tissue-piercing element may have any of a variety of geometric shapes and dimensions, including ones that minimize tissue trauma and reduce the force required for skin penetration. For example, in some embodiments, the tissue-piercing element may comprise a substantially conically-shaped distal tip, as illustrated in FIG. 1, such that the cross-sectional dimensions (e.g., diameter) of the tissue-piercing element tapers to a point 118 at the distal end of the tip, thereby providing a sharpened leading edge configured to facilitate skin penetration. As illustrated in FIG. 2B, in other embodiments, the distal tip of the tissue-piercing element may be beveled with a bevel angle α, such as, for example, an angle of from about 5° to about 66°, or from about 10° to about 55°, or from about 40° to about 50°. In further embodiments, one or more surfaces of the tip may be curved, such as illustrated in FIGS. 2C-2H and 3D, so as to facilitate skin penetration when the sensor device is pushed downwards. In some embodiments, a curved surface may be advantageous because it provides the tissue-piercing element with a greater cutting surface area than a straight surface, and thus provides a smoother and more controlled insertion of the sensor unit through the skin. Also, a tissue-piercing element with a curved surface may cause less trauma to the pierced tissue than one with a straight surface.

The tissue-piercing element of the sensor device is designed to have appropriate flexibility and hardness and sufficient column strength to allow it to remain intact and to prevent it from substantial buckling during insertion of the in vivo portion of the sensor device through the skin of the host. Any of a variety of biocompatible materials having these characteristics may be used to form the tissue-piercing element, including, but not limited to, metals, ceramics, semiconductors, organics, polymers, composites, and combinations or mixtures thereof. Metals that may be used include stainless steel (e.g., 18-8 surgical steel), nitinol, gold, silver, nickel, titanium, tantalum, palladium, gold, and combinations or alloys thereof, for example. Polymers that may be used include polycarbonate, polymethacrylic acid, ethylenevinyl acetate, polytetrafluorethylene (TEFLON©), and polyesters, for example. In some embodiments, the tissue-piercing element may serve as a reference electrode and comprise a conductive material, such as a silver-containing material, for example. In certain embodiments, the tissue-piercing element has sufficient column strength to allow the user to press the sensor unit through the skin using the force from a thumb or finger, without substantial buckling of the tissue-piercing element. Accordingly, the structure of the tissue-piercing unit does not fail when it is subjected to resistance (e.g., axial force) associated with the penetration of tissue and skin. In some embodiments, the tissue-piercing element may have a column strength capable of withstanding an axial load greater than about 0.5 Newtons (N), or greater than about 1 N, or greater than about 2 N, or greater than about 5 N, or greater than about 10 N, without substantial buckling. Often, an increase in the column thickness of an object will also increase its column strength. In some embodiments, the base 120 of the distal tip may have an outside diameter of from about 0.05 mm to about 1 mm, or from about 0.1 mm to about 0.5 mm, or from about 0.15 mm to about 0.3 mm, to provide the desired column strength for the tissue-piercing element.

Some of the tissue-piercing elements described herein are configured to protect the membrane of the sensor body. As described elsewhere herein, the membrane may be relatively delicate, and thus may be damaged during insertion of the sensor unit into the host. Consequently, any damage sustained by the membrane may affect the sensor device's performance and its ability to function properly. For example, in some embodiments one or more portions of the tissue-piercing element 108 may be formed with a cross-sectional area (along a plane transverse to the longitudinal axis of the tissue-piercing element 108) larger than that of the sensor body 110. By having a cross-sectional area larger than that of the sensor body 110, the tissue-piercing element 108 of the sensor device 100 is configured to pierce the host's skin 104 and to open and define a passage for insertion of the sensor body 110 into the tissue. Thus, the risk of a penetration-resistance force damaging and/or stripping the membrane 140 off from the rest of the sensor body 110 during the insertion process is reduced. In some embodiments, the largest dimension of the cross section transverse to a longitudinal axis of the tissue-piercing element 108 is less than about 0.1 mm, or less than about 0.05 mm, or less than about 0.03 mm.

In some embodiments, one or more layers of one or more polymers and/or bioactive agents may be coated onto the tissue-piercing element. The use of bioactive agents to coat the surface of the tissue-piercing element may provide a release of bioactive agents in the subcutaneous tissue during and/or after insertion of the in vivo portion of the sensor device. In further embodiments, one or more polymer layers may be used to control the release rate of the one or more bioactive agents. Such polymers may include, but are not limited to, parylene, parylene C, parylene N, parylene F, poly(hydroxymethyl-p-xylylene-co-p-xylylene) (PHPX), poly(lactic-co-glycolic acid) (PLGA), polyethylene-co-vinyl acetate (PEVA), Poly-L-lactic acid (PLA), poly N-butyl methacrylate (PBMA), phosphorylcholine, poly(isobutylene-co-styrene), polyoxyethylene (POE), polyglycolide (PGA), (poly(L-lactic acid), poly(amic acid) (PAA, polyethylene glycol (PEG), derivatives of one or more of these polymers, and combinations or mixtures thereof.

In some embodiments, one or more regions of the surface of the tissue-piercing element may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and dimensions, in accordance with the intended application. Use of reservoirs or depots may increase the amount of bioactive agents the tissue-piercing element is capable of carrying and delivering. In further embodiments, the tissue-piercing element may be hollow with a cavity and connected via various passages with one or more openings on its surface, so that bioactive agents may be released from the cavity via the openings. In some embodiments, for example as shown FIGS. 3A and 3B, the tissue-piercing element 310 comprises a pocket 312 shaped and dimensioned to support a sensor 314 with a membrane disposed thereon.

In certain embodiments, the in vivo portion of the sensor device is configured to remain substantially stationary within the tissue of the host, so that migration or motion of the sensor body with respect to the surrounding tissue is inhibited. Migration or motion may cause inflammation at the sensor implant site due to irritation, and may also cause noise on the sensor signal due to motion-related artifacts. Therefore, it may be advantageous to provide an anchoring mechanism that provides support for the in vivo portion of the sensor device to avoid the aforementioned problems. In some embodiments, the tissue-piercing element may comprise a surface with one or more regions that are textured. Texturing may roughen the surface of the tissue-piercing element and thereby provide a surface contour with a greater surface area than that of a non-textured (e.g., smooth) surface. Accordingly, the amount of bioactive agents, polymers, and/or coatings that the tissue-piercing element may carry and be released in situ is increased, as compared to that with a non-textured surface. Furthermore, it is believed that a textured surface may also be advantageous in some instances, because the increased surface area may enhance immobilization of the in vivo portion of the sensor device within the tissue of the host. In certain embodiments, the tissue-piercing element may comprise a surface topography with a porous surface (e.g. porous parylene), ridged surface, etc. In certain embodiments, the anchoring may be provided by prongs, spines, barbs, wings, hooks, a bulbous portion (for example, at the distal end), an S-bend along the tissue-piercing element, a gradually changing diameter, combinations thereof, etc., which may be used alone or in combination to stabilize the sensor within the subcutaneous tissue. For example, in certain embodiments, the tissue-piercing element may comprise one or more anchoring members configured to splay outwardly (e.g., in a direction toward a plane perpendicular to the longitudinal axis of the sensor unit) during or after insertion of the sensor unit. Outward deployment of the anchoring member facilitates anchoring of the sensor unit, as it results in the tissue-piercing element pressing against the surrounding tissue, and thus reduces (or prevents) movement and/or rotation of the sensor unit. In some embodiments, the anchoring members are formed of a shape memory material, such as nitinol, which may be configured to transform from a martensitic state to an austenitic state at a specific temperature (e.g., room temperature or body temperature). In the martensitic state, the anchoring members are ductile and in a contracted configuration. In the austenitic state, the anchoring members deploy to form a larger predetermined shape while becoming more rigid. While nitinol is described herein as an example of a shape memory material that may be chosen to form the anchoring member, it should be understood that other similar materials (e.g., shape memory material) may also be used.

The tissue-piercing element of the sensor device may be introduced subcutaneously at any of a variety of angles with respect to the mounting surface (the bottom surface of the mounting unit), and thus the skin surface. For example, in some embodiments the distal tip of the tissue-piercing element may extend substantially perpendicular to the mounting surface, but in other embodiments, the distal tip may extend at an angle with respect to the mounting surface of about 15°, 20°, 30°, 40°, 45°, 60°, 75° 80°, 90°, 105°, 100°, 120°, 135°, 140°, 150°, 160°, or 165°, for example.

In alternative embodiments, to provide protection of the membrane during insertion of the sensor device, the sensor body may be embedded or encapsulated in a needle formed of a biodegradable material. Following insertion, the needle gradually biodegrades, leaving behind the sensor body which may then be activated. Any of a variety of biodegradable materials (e.g., a non-interfering carbohydrate) may be used. In some embodiments, the biodegradable material may include a certain concentration of an analyte to be measured, so that an initial calibration point of the sensor device may be provided.

As illustrated in FIG. 1, the sensor device 100 may include a skin-contacting mounting unit 116 configured to be secured to a host. In some embodiments, the mounting unit 116 comprises a base 122 adapted for fastening to a host's skin. The base 122 may be formed from a variety of hard or soft materials and may comprise a low profile for reducing protrusion of the sensor device from the host during use. In some embodiments, the base 122 is formed at least partially from a flexible material configured to conform to skin contour, so as to reduce or eliminate motion-related artifacts associated with movement by the host. In certain embodiments, the base 122 of the mounting unit 116 includes an adhesive material or adhesive layer 124, also referred to as an adhesive pad, preferably disposed on the mounting unit's bottom surface, and may include a releasable backing layer (not shown). Thus, removing the backing layer and pressing the base 122 of the mounting unit 116 onto the host's skin 104 adheres the mounting unit 116 to the host's skin 104. Appropriate adhesive layers may be chosen and designed to stretch, elongate, conform to, and/or aerate the region (e.g. host's skin). In some embodiments, the mounting unit comprises a guiding portion (not shown) configured to guide insertion of the sensor device 100 through the host's skin 104 and to support a column strength of the support member 112 such that the sensor device 100 is capable of being inserted through the host's skin 104 without substantial buckling.

Figure 3A:
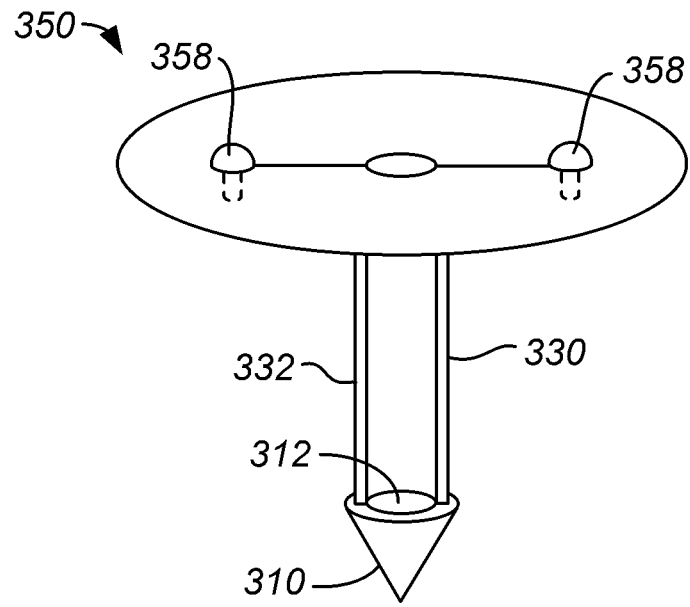
FIGS. 3A-3D are top perspective views of additional continuous analyte sensors according to the present embodiments.
Figure 3B:
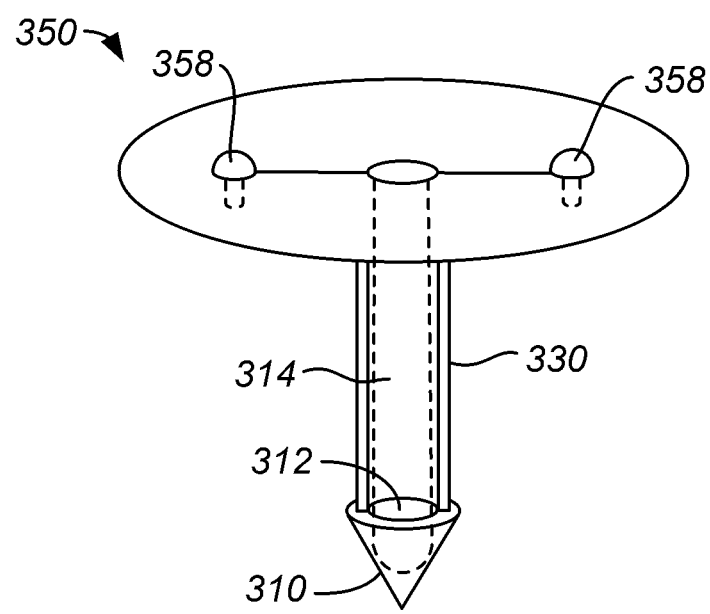
Figure 3C:
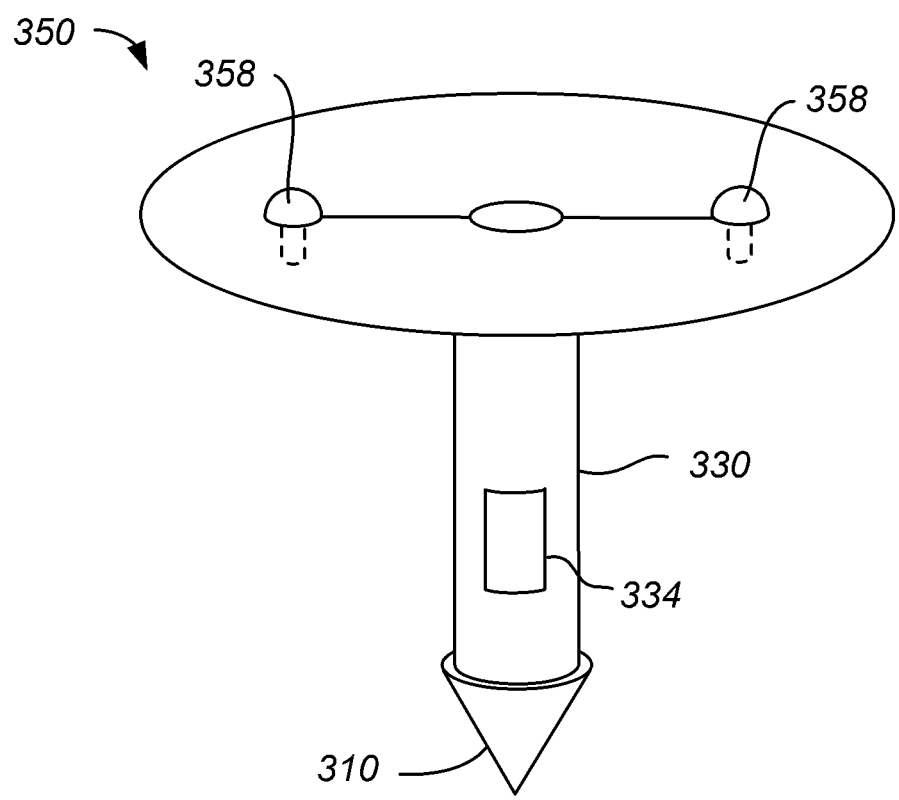
Figure 3D:
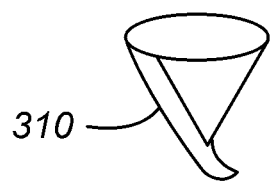

While FIG. 1 illustrates one configuration for providing membrane protection, other sensor body configurations may also be used. For example, some of the sensor bodies described herein may include a support member 330 configured to partially surround a sensor, as illustrated in FIGS. 3A and 3B, or configured to substantially surround a sensor, as illustrated in FIG. 3C. Unlike other embodiments described elsewhere herein, in the embodiments illustrated in FIGS. 3A-3C, the support member 330 does not comprise a working electrode. Rather, one or more working electrodes are arranged as components distinct from the support member 330. In some embodiments, the support member 330 may also serve as a reference electrode.

In the embodiment illustrated in FIG. 3A, the support member 330 comprises a longitudinal recess 332 configured to at least partially accommodate a sensor (e.g., a working electrode with a membrane disposed thereon). In some embodiments, the longitudinal recess may have a length corresponding to less than about 90% of the length of the support member 330, or less than about 75%, or less than about 50%, or less than about 33%, or less than about 25%. In other embodiments, the longitudinal recess may extend substantially across the entire length of the support member 330, as illustrated in FIG. 3B. In certain embodiments, the support member 330 may surround more than about 10% of the outer perimeter (e.g., circumference) of the sensor, or more than about 25%, or more than about 33%, or more than about 50%, or more than about 75%.

As illustrated in FIG. 3C, in some embodiments wherein the sensor (e.g., the working electrode) is substantially surrounded by the support member 330. The support member 330 may be provided with one or more window portions 334 (openings or slots extending through the wall thickness of the support member 330) that expose certain portions of the electrode to biological fluid (e.g., interstitial fluid), and thus allow biological fluid to diffuse toward and contact the working electrode's electroactive surface and the membrane disposed thereon. In this embodiment, the working electrode and the membrane disposed thereon are essentially housed within the support member 330, and are thus protected during packing, handling, and/or insertion of the device. The window portions 334 may have any of a variety of shapes and dimensions. For example, in some embodiments, the window portions may be formed to have a circular or substantially circular shape, but in other embodiments, the electrode may be formed with a shape resembling an ellipse, a polygon (e.g., triangle, square, rectangle, parallelogram, trapezoid, pentagon, hexagon, octagon), or the like. In certain embodiments, the window portions may comprise sections that extend around the perimeter of the longitudinal cross section of the support member. For example, the support member may be made by using a hypo-tube with window portions cut out in a spiral configuration, by ablation, etching, or other techniques.

Permeability

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. In some embodiments, from about 1, 2, 3, 4, or 5 picoAmps to about 25, 50, 100, 250, or 500 picoAmps of current is measured for every unit (mg/dl) of glucose measured.

Bioactive Agents

A variety of bioactive agents are known to promote fluid influx or efflux. Accordingly, incorporation of bioactive agents into the membrane may increase fluid bulk, bulk fluid flow, and/or diffusion rates (and promoting glucose and oxygen influx), thereby decrease non-constant noise. In some embodiments, fluid bulk and/or bulk fluid flow are increased at (e.g., adjacent to the sensor exterior surface) the sensor by incorporation of one or more bioactive agents. In some embodiments, the sensor is configured to include a bioactive agent that irritates the wound and stimulates the release of soluble mediators that are known to cause a local fluid influx at the wound site. In some embodiments, the sensor is configured to include a vasodilating bioactive agent, which may cause a local influx of fluid from the vasculature.

A variety of bioactive agents may be found useful in preferred embodiments. Example bioactive agents include but are not limited to blood-brain barrier disruptive agents and vasodilating agents, vasodilating agents, angiogenic factors, and the like. Useful bioactive agents include but are not limited to mannitol, sodium thiosulfate, VEGF/VPF, NO, NO-donors, leptin, bradykinin, histamines, blood components, platelet rich plasma (PRP), matrix metalloproteinases (MMP), Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulfate, Estradiol, prostaglandins, cox inhibitors, endothelial cell binding agents (for example, decorin or vimentin), glenipin, hydrogen peroxide, nicotine, and Growth Hormone. Still other useful bioactive agents include enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, proinflammatory factors and the like.

Bioactive agents may be added during manufacture of the sensor by incorporating the desired bioactive agent in the manufacturing material for one or more sensor layers or into an exterior biomaterial, such as a porous silicone membrane. For example, bioactive agents may be mixed with a solution during membrane formation, which is subsequently applied onto the sensor during manufacture. Alternatively, the completed sensor may be dipped into or sprayed with a solution of a bioactive agent, for example. The amount of bioactive agent may be controlled by varying its concentration, varying the indwell time during dipping, applying multiple layers until a desired thickness is reached, and the like, as disclosed elsewhere herein. In an alternative embodiment, the bioactive agent is microencapsulated before application to the sensor. For example, microencapsulated bioactive agent may be sprayed onto a completed sensor or incorporated into a structure, such as an outer mesh layer or a shedding layer. Microencapsulation may offer increased flexibility in controlling bioactive agent release rate, time of release occurrence and/or release duration.

Chemical systems/methods of irritation may be incorporated into an exterior sensor structure, such as the biointerface membrane (described elsewhere herein) or a shedding layer that releases the irritating agent into the local environment. For example, in some embodiments, a "shedding layer" releases (e.g., sheds or leaches) molecules into the local vicinity of the sensor and may speed up osmotic fluid shifts. In some embodiments, a shedding layer may provide a mild irritation and encourage a mild inflammatory/foreign body response, thereby preventing cells from stabilizing and building up an ordered, fibrous capsule and promoting fluid pocket formation.

A shedding layer may be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, may be used. The acid residues are chemical irritants that stimulate inflammation and wound healing. In certain embodiments, these compounds include glycolic acid and lactic acid based polymers, polyglactin, polydioxone, polydyconate, poly(dioxanone), poly(trimethylene carbonate) copolymers, and poly (caprolactone) homopolymers and copolymers, and the like.

In other example embodiments, the shedding layer may be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. No. 4,803,243 and U.S. patent). In one preferred embodiment, the shedding layer is comprised of polyurethane and a hydrophilic polymer. For example, the hydrophilic polymer may be polyvinylpyrrolidone. In one preferred embodiment, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other example embodiments, the shedding layer may include a silicone elastomer, such as a silicone elastomer and a poly(ethylene oxide) and poly(propylene oxide) co-polymer blend, as disclosed in copending U.S. patent application Ser. No. 11/404,417 filed on Apr. 14, 2006. In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC© polymer. In one embodiment, the co-polymer is PLURONIC© F-127. In one embodiment, at least a portion of the co-polymer is cross-linked. In one embodiment, from about 5% w/w to about 30% w/w of the membrane is the co-polymer.

A shedding layer may take any shape or geometry, symmetrical or asymmetrical, to promote fluid influx in a desired location of the sensor, such as the sensor head or the electrochemically reactive surfaces, for example. Shedding layers may be located on one side of sensor or both sides. In another example, the shedding layer may be applied to only a small portion of the sensor or the entire sensor.

In one example embodiment, a shedding layer comprising polyethylene oxide (PEO) is applied to the exterior of the sensor, where the tissue surrounding the sensor may directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise may be reduced or eliminated and sensor function may be improved.

In another example embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material may be absorbed into the lower portion of the porous silicone (e.g., the portion of the porous silicone that will be proximal to the sensor after the porous silicone has been applied to the sensor) prior to application of the porous silicone to the sensor.

Wound Suppression

Non-constant noise may be decreased by wound suppression (e.g., during sensor insertion), in some embodiments. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferents and reducing early noise.

Wounds may be suppressed by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, etc. In one example embodiment, the sensor is configured to have a low profile, a zero-footprint or a smooth surface. For example, the sensor may be formed of substantially thin wires, such as wires from about 50 m to about 116 m in diameter, for example. Preferably, the sensor is small enough to fit within a very small gauge needle, such as a 30, 31, 32, 33, 34, or 35 gauge needle (or smaller) on the Stubs scale, for example. In general, a smaller needle, the more reduces the amount of wounding during insertion. For example, a very small needle may reduce the amount of tissue disruption and thereby reduce the subsequent wound healing response. In an alternative embodiment, the sensor's surface is smoothed with a lubricious coating, to reduce wounding upon sensor insertion.

Wounding may also be reduced by inclusion of wound-suppressive agents (bioactive agents) that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor may create a locally quiescent environment and suppress wound healing. In a quiescent environment, bodily processes, such as the increased cellular metabolism associated with wound healing, may minimally affect the sensor. If the tissue surrounding the sensor is undisturbed, it may continue its normal metabolism and promote sensor function.

In some embodiment, useful compounds and/or factors for suppressing wounding include but are not limited to first-generation $H_1$-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine); second-generation $H_1$-receptor antagonists such as acrivastine, astemizole, cetirizine, loratadine, mizolastine, azelastine, levocabastine, and olopatadine; mast cell stabilizers such as cromoglicate (cromolyn) and nedocromil; anti-inflammatory agents, such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (e.g., L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone; immunosuppressive and/or immunomodulatory agents such as anti-proliferative, cell-cycle inhibitors (e.g., paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARy ligands (for example troglitazone, rosiglitazone, pioglitazone), halofugione, C-proteinase inhibitors, probucol, BCP671, EPC antibodies, catchins, glycating agents, endothelin inhibitors (for example, Ambrisentan, Tesosentan, Bosentan), Statins (for example, Cerivastatin), *E. coli* heat-labile enterotoxin, and advanced coatings; anti-infective agents, such as anthelmintics (mebendazole); antibiotics such as aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim; interferent scavengers, such as superoxide dismutase (SOD), thioredoxin, glutathione peroxidase and catalase, anti-oxidants, such as uric acid and vitamin C, iron compounds, Heme compounds, and some heavy metals; artificial protective coating components, such as albumin, fibrin, collagen, endothelial cells, wound closure chemicals, blood products, platelet-rich plasma, growth factors and the like.

While not wishing to be bound by theory, it is believed that, in addition to the analyte sensor configurations described elsewhere herein, application of a lubricious coating to the sensor may substantially reduce and/or suppress noise occurrence by substantially preventing injury to the host. Accordingly, in some embodiments, a lubricious coating may be applied to the in vivo portion of the sensor to reduce the foreign body response to the implanted sensor. The term "lubricous coating" as used herein is used in its ordinary sense, including without limitation, a surface treatment that provides a reduced surface friction. A variety of polymers are suitable for use as a lubricious sensor coating, such as but not limited to Teflon, polyethylene, polycarbonate, polyurethane, poly(ethylene oxide), poly(ethylene oxide)-poly(propylene oxide) copolymers, and the like. In one example embodiment, one or more layers of HydroMed™, a polyether-polyurethane manufactured by CardioTech International, Inc. (Wilmington, Mass.) is applied to the sensor (e.g., over the resistance domain).

Dissolvable Tip

Sensors such as those described above are sometimes referred to as "tack" sensors, due to their resemblance to a thumbtack. One aspect of the present embodiments includes the realization that tack sensors include a sharpened tip that remains implanted in the tissue throughout the usable life of the sensor. Leaving the sharpened tip in vivo for an extended period of time may cause trauma to surrounding tissue, leading to scarring and inhibition of wound healing. Some of the present embodiments provide solutions to this problem. In some embodiments, the tip is configured to dissolve during the implantable sensor session, for example, within about 3, 5, 7 or 10 days.

As described above, and with reference to FIG. 1, the tissue-piercing element 108 may be a discrete component, separate from, for example, the sensor body 112. In such embodiments, the sensor body 112 may include a blunt tip or distal face 126. The tissue-piercing element 108 similarly includes a blunt proximal face 128 that abuts the sensor body tip 126. As described above, the tissue-piercing element 108 may or may not be secured to the sensor body 112.

In some embodiments, the tissue-piercing element 108 may comprise a biodegradable material, or a material that rapidly dissolves upon insertion into the host. Upon implantation, degradation of the tissue-piercing element 108 may be spontaneous with acid residues. In such embodiments, any sensor membrane(s) is desirably pH insensitive. A rate of degradation of the tissue-piercing element 108 depends upon the amount of tip material present. For example, the material may biodegrade/dissolve within three days after insertion into the host, or within two days, or one day, or twelve hours, or six hours, or three hours, or two hours, or one hour. In certain embodiments, the material may dissolve within a timeframe before which the sensor begins operating. In such embodiments, the dissolved material of the tissue-piercing element 108 may not interfere with sensor calibration.

Example materials for the tissue-piercing element 108 include at least one of a salt, a metallic salt, a sugar, a synthetic polymer, a glue or adhesive (such as cyanoacrylate), polylactic acid (PLA), polyglycolic acid, poly(lactic-co-glycolic acid) (PLGA), a polyanhydride, a polyphosphazene, or any material with glass-like properties. In particular, PLA, PLGA, and polyanhydrides all have sufficient hardness for this type of application. For example, a hardness of the tissue-piercing element 108 may be in the range of 35 D to 55 D, such as for example 45 D.

In some embodiments, the material of the tissue-piercing element 108 may be tuned or modified to achieve desired properties, such as dissolution time, hardness, etc. For example, the tissue-piercing element 108 may be processed with annealing and hardening cycles, and/or cross-linking. Cross-linking may be, for example, light based, such as irradiation with UV light. In some embodiments, the tuning may comprise combining materials. For example, the hardness of the tissue-piercing element 108 may be improved by incorporating hydroxyapatite in a blend, similar to some bone implants. Such a blend dramatically increases hardness. Also, these inclusions tend to lead to faster dissolution times.

If a polymer material is selected for the tissue-piercing element 108, it may have a crystallinity, which can also be defined by a Rockwell Hardness. For example, the material may have a Rockwell Hardness of about 25D-65D, such as about 45D. An adequate Rockwell Hardness enables the polymer to undergo various processing steps without tearing or damage to the polymer.

Figure 4:
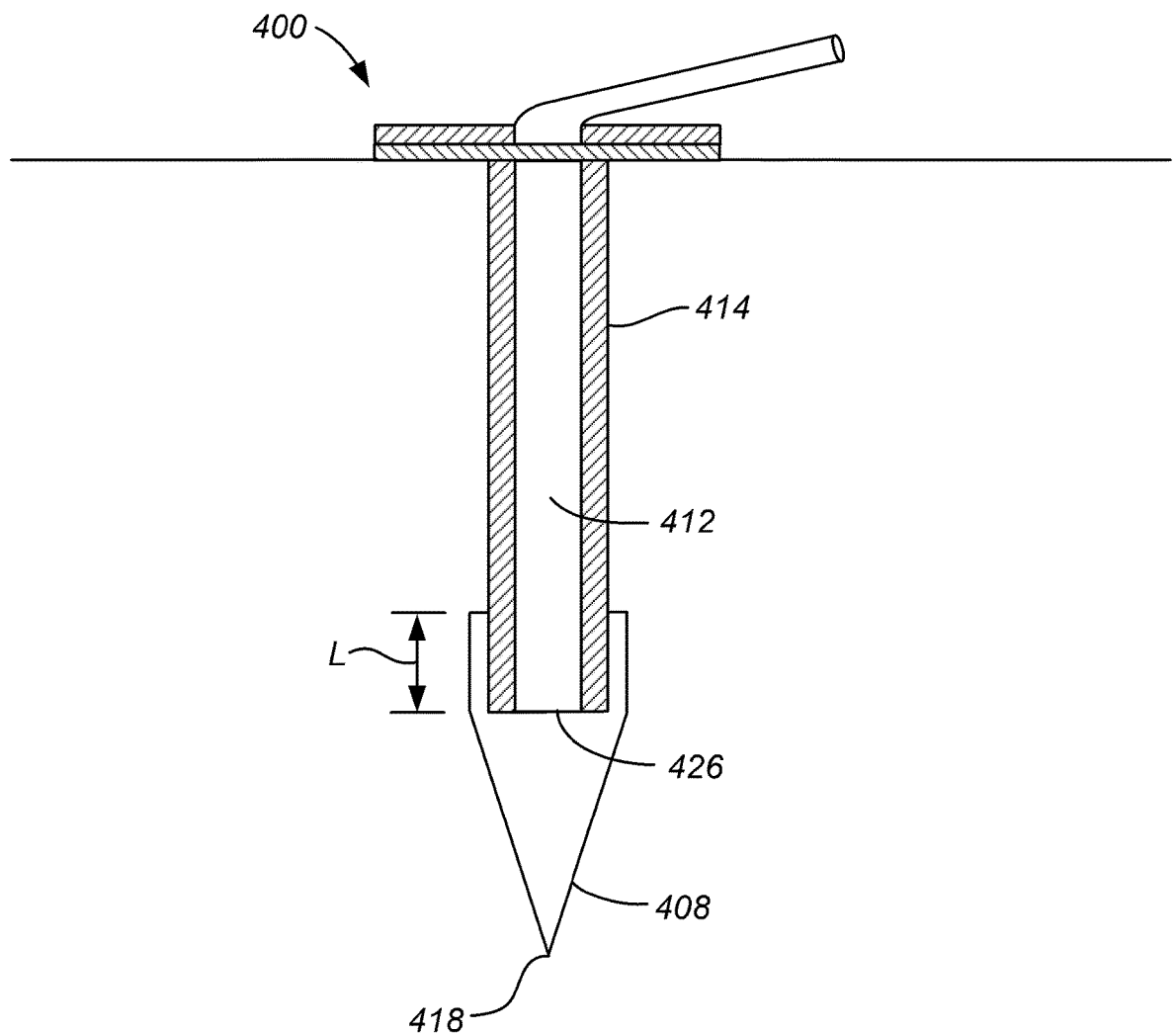
FIG. 4 is a continuous analyte sensor according to the present embodiments.

In some embodiments, the tissue-piercing element 108 may comprise a coating that covers at least a portion of the sensor body 112, including the sensor tip 126. For example, with reference to FIG. 4, a length L of the distal end of the sensor body 412 and membrane 414 may be dipped in a liquid bath (not shown). The length L may be chosen to coat enough of the sensor tip to achieve good adhesion without covering any electrodes on the sensor. For example, L may in the range of 0.1-4 mm, such as 2-3 mm. As the sensor is withdrawn from the bath, the coating remains over the length L, and extends distally from the sensor body tip 426, forming a dissolvable tissue-piercing tip 408. After the coating cures, the portion extending from the sensor tip may be sharpened to produce a tissue-piercing coating tip 418.

In certain example embodiments, a viscosity of the liquid bath is below 100 cP, and the withdrawal rate is 20-30 in/sec, with an immediate exposure to UV (or heat) cross-linking to cure and build thickness. A tip mold or draw-through fixture that clamps and cures in one step in order to form a sharp cone shape is advantageous.

Another embodiment to create a sharp sensor tip with a polymer is to apply a voltage to the material while it is being cured. The voltage causes the polymer to modify its shape to a point. The sharp tip remains when the curing is completed and the voltage is removed. Curing could comprise irradiating, drying, heating, etc. Another embodiment comprises heating the material and drawing it out like glass.

As discussed above, the sensor 400 may include one or more aspects that either suppress wounding, or promote rapid healing, or both. In certain embodiments, these aspects may be present in the dissolvable tip 408. For example, one or more bioactive agents may be integrated into the dissolvable tip 408 by combining it with the material of the liquid bath during the dipping process. Alternatively, before or after curing, the dissolvable tip 408 may be dipped in a subsequent liquid bath that coats the dissolvable tip 408 with one or more bioactive agents. Example bioactive agents are discussed at length above and will not be repeated here. However, certain bioactive agents may, for example, induce osmotic pressure or oncotic pressure.

In certain embodiments, the material of the dissolvable tip 408 may have an effect on the sensor 400. For example, if the dissolvable tip 408 is a salt, it could set up an osmotic pressure gradient that may pull fluids to the tissue surrounding the sensor 400, causing it to startup faster or avoid early signal attenuation.

Dissolvable Needle

Some of the present embodiments relate to sensors that require a needle for insertion into the host. For example, with reference to FIG. 5, the sensor 500 may be contained within a lumen 504 of a needle 502. Another aspect of the present embodiments includes the realization that the need to remove the needle after sensor insertion adds complexity to the insertion process, including the need to electrically connect the sensor to sensor electronics after insertion. Some of the present embodiments provide solutions to this problem.

Figure 5:
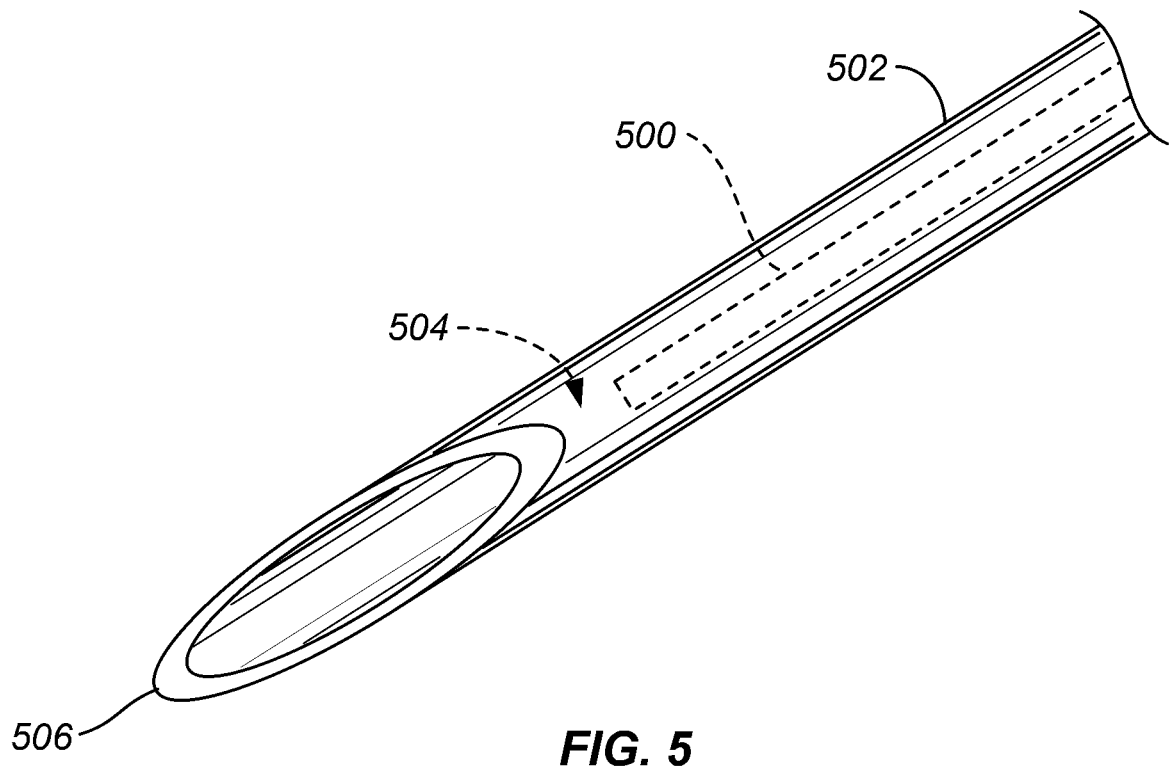
FIG. 5 is a front perspective view of a system for inserting a continuous analyte sensor into a host according to the present embodiments.

With reference to FIG. 5, the needle 502 may be similar to a standard hypodermic needle 502, including a lumen 504 and a sharp distal tip 506. However, the material of the needle 502 may be biodegradable, or capable of dissolving after insertion into a host. The material and material properties of the needle 502 may be similar to those discussed above with respect to the dissolvable tissue-piercing tip 506. These materials and material properties are discussed at length above, and will not be repeated here. However, polyanhydrides are one particularly advantageous material for the needle 502, as they may form tubes readily and those in turn may be sharpened by cutting.

Figure 6:
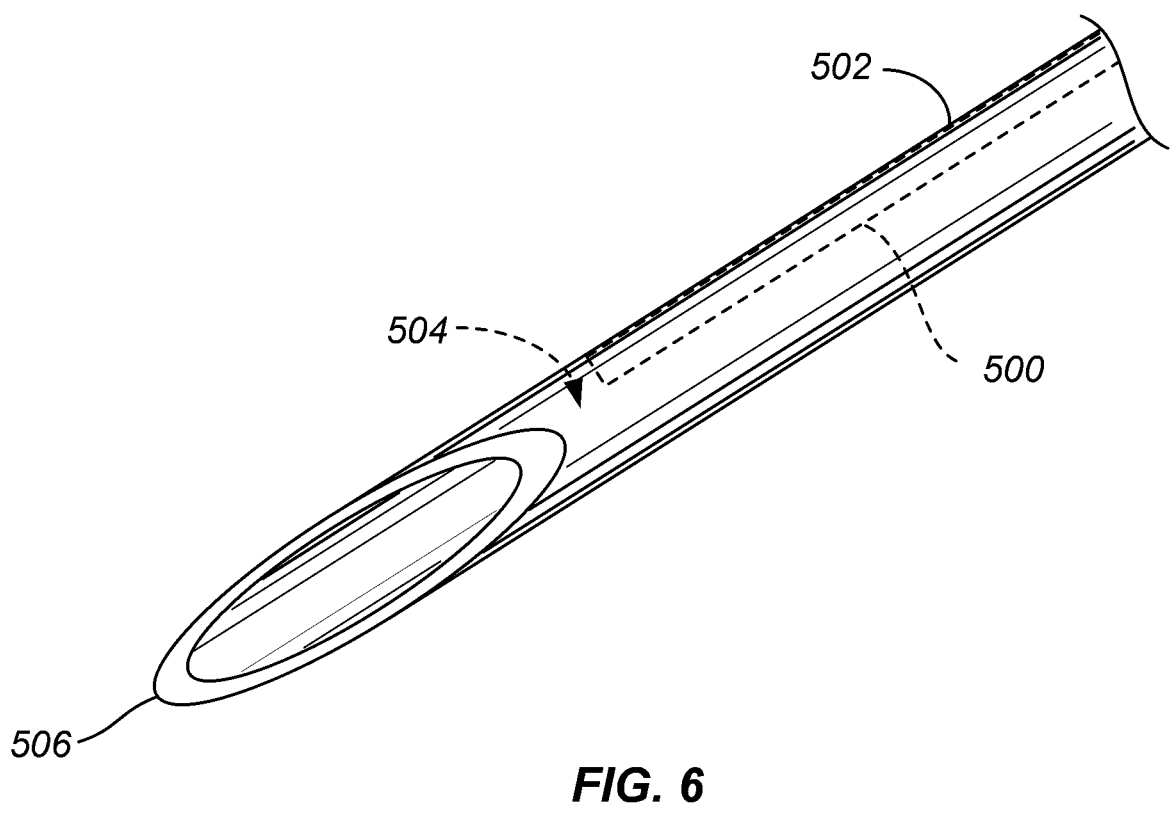
FIG. 6 is a front perspective view of another system for inserting a continuous analyte sensor into a host according to the present embodiments.

In some embodiments, the sensor 500 may be received within the lumen 504 but not attached to the needle 502 (FIG. 5), for example may be held via friction force within the needle and/or couple to a base, such as base 122 as shown in FIG. 1. In other embodiments, the sensor 500 may be attached to the needle 502 (FIG. 6) using mechanical or chemical coupling methodologies, as may be appreciated by one skilled in the art.

In the present embodiments, since the needle 502 is biodegradable/dissolvable, it does not need to be removed from the host after the sensor 500 is inserted. Instead, the needle 502 harmlessly biodegrades, thereby eliminating the traumatic tip 506 and leaving behind the sensor 500. The dissolvable needle 502 thus simplifies the process of inserting the sensor 500 into the host. In addition, since the needle 502 does not need to be withdrawn, the sensor 500 may be electrically connected to sensor electronics (not shown) prior to insertion. This aspect advantageously eliminates the need to connect the sensor 500 to sensor electronics after insertion, which may be challenging.

As with the embodiments of the dissolvable tissue-piercing tip 506 discussed above, the present dissolvable needle 502 may include one or more bioactive agents to suppress wounding and/or promote rapid wound healing. These bioactive agents may be similar to those discussed above, and may be applied to/integrated into the needle 502 using the same techniques discussed above.

In certain embodiments, the needle 502 may be at least partially dissolvable. In such embodiments, the needle may have stronger and weaker (or more and less dissolvable) portions, such that in vivo the weaker portions dissolve more quickly and the stronger portions then break away from one another. The stronger portions may ultimately dissolve, albeit more slowly than the weaker portions. Such embodiments may be described as "fractionate," referring to how the weaker portions dissolve quickly allowing the hard segments, such as PLA or PGA, that provide sufficient strength during insertion, to fragment away, while not harming the body during or after sensor insertion.

Membrane Hardening Agent

One aspect of the present embodiments includes the realization that the material of analyte sensor membranes is soft, and tends to peel back as the sensor advances into tissue. This problem is especially acute for sensors that are formed by a process in which they are first coated with a membrane and then sharpened at the tip. This process exposes the sensor body, and leaves a thin coating of the membrane surrounding the sides of the sensor body at the tip. Some of the present embodiments provide solutions to this problem.

Figure 7:
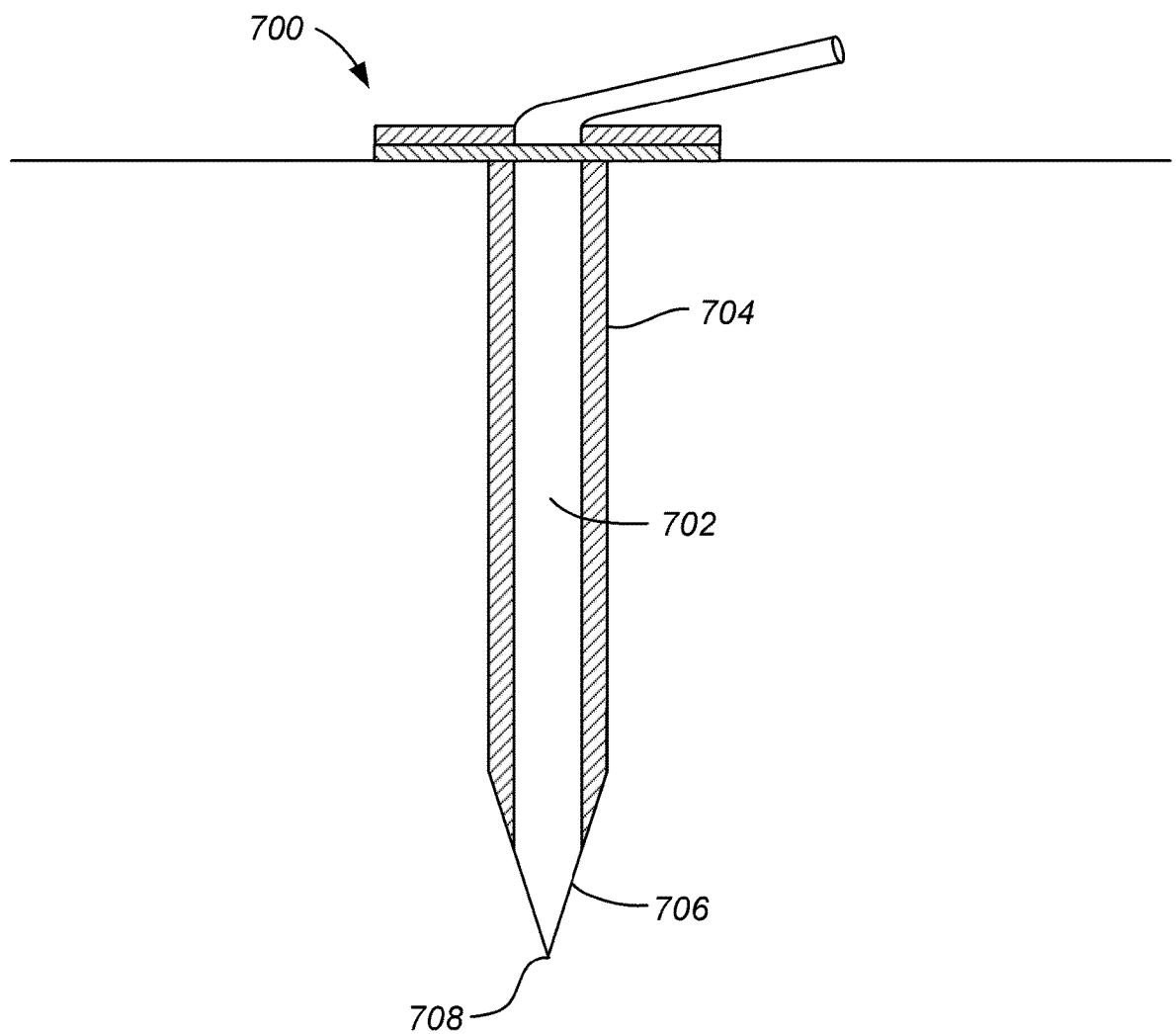
FIG. 7 is a continuous analyte sensor according to the present embodiments.

FIG. 7 illustrates a sensor unit 700 similar to the sensor device 100 described above and shown in FIG. 1. The sensor unit 700 includes a sensor body 702 at least partially covered by a membrane 704. Rather than having a discrete tissue-piercing element, as in the previous embodiments, instead the distal end 706 of the sensor body 702 and membrane 704 are sharpened to form a tissue-piercing tip 708. Since the sensor is sharpened after being coated with the membrane 704, a portion of the sensor body 702 is exposed at the sharpened tip 708. In an alternative embodiment illustrated in FIG. 8, the sensor body 802 may be sharpened prior to being coated with the membrane 804, so that the sharpened tip 808 is covered with membrane 804.

Figure 8:
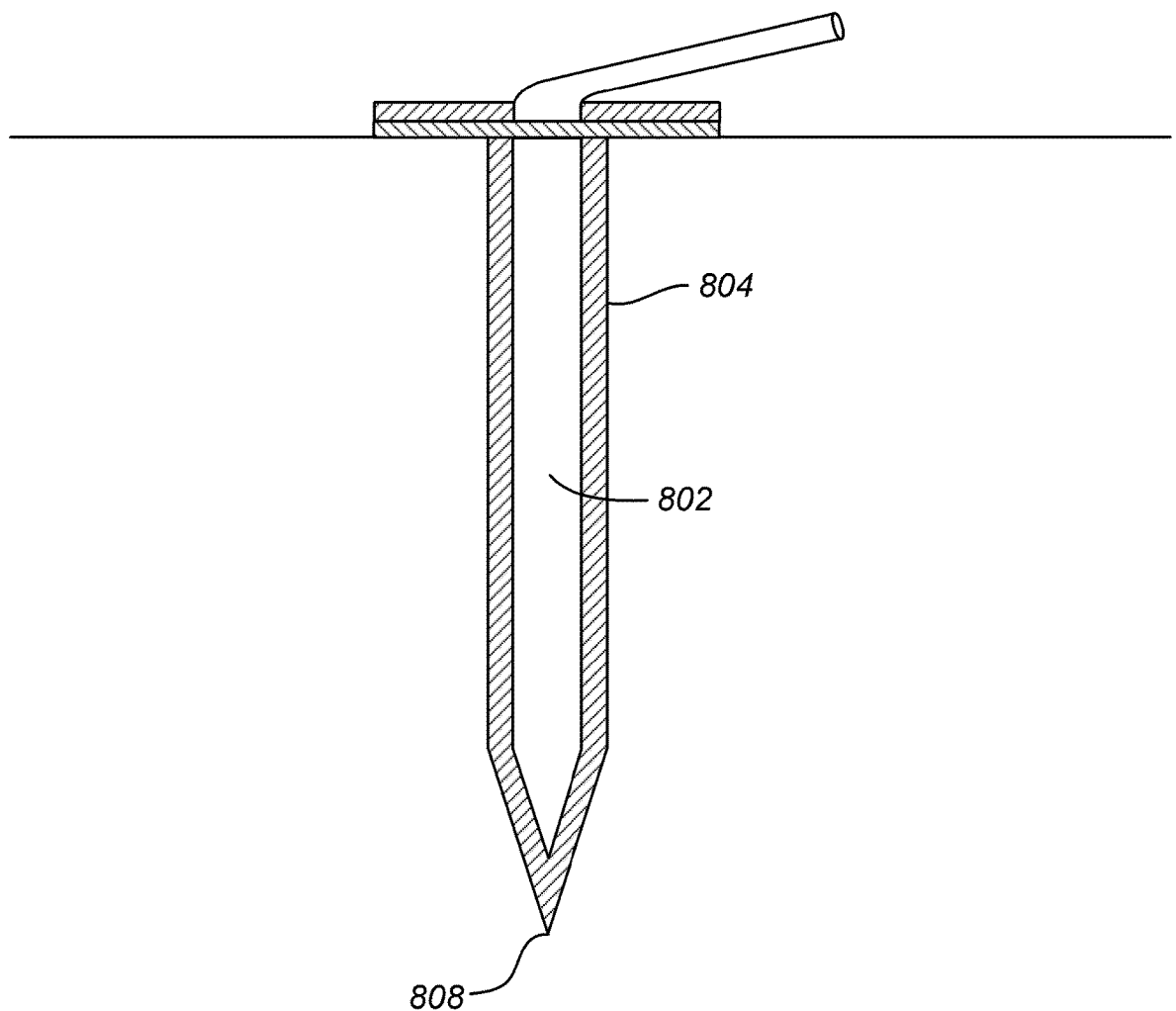
FIG. 8 is a continuous analyte sensor according to the present embodiments.

In the embodiments of FIGS. 7 and 8, the distal end of the sensor body 702/802 may be sharpened by any of a variety of methods, such as laser ablation, mechanical grinding, diamond wire, high-speed milling, abrasive water jet cutting, electric discharge machining by wire or plunge, electrochemical machining, electrochemical etching, electrochemical polishing, stamping, or any other method.

In both of the embodiments illustrated in FIGS. 7 and 8, the soft membrane 704, 804 is susceptible to peeling back as the sensor advances through tissue during the process of being inserted into the host. Also, due to its very small diameter, the sensor of FIGS. 7 and 8 may lack the column strength necessary to be inserted through the host's skin without substantial buckling. To solve these problems, certain of the present embodiments provide a hardening agent 900 that either covers the membrane 902 (FIG. 9) or is integrated into the membrane 902 (FIG. 10). The hardening agent 900 provides increased column strength to the sensor body 904 so that the sensor unit 906 is capable of being inserted through the host's skin 908 without substantial buckling. The hardening agent 900 may also increase adhesion of the membrane 902 to the sensor body 904 and/or stiffen the membrane 902 so that it is more resistant to peeling back as the sensor advances through tissue during the process of being inserted into the host. Preferably, however, the hardening agent 900 allows analyte permeability within the membrane 902 so that the ability of the sensor to function is not compromised.

Figure 9:
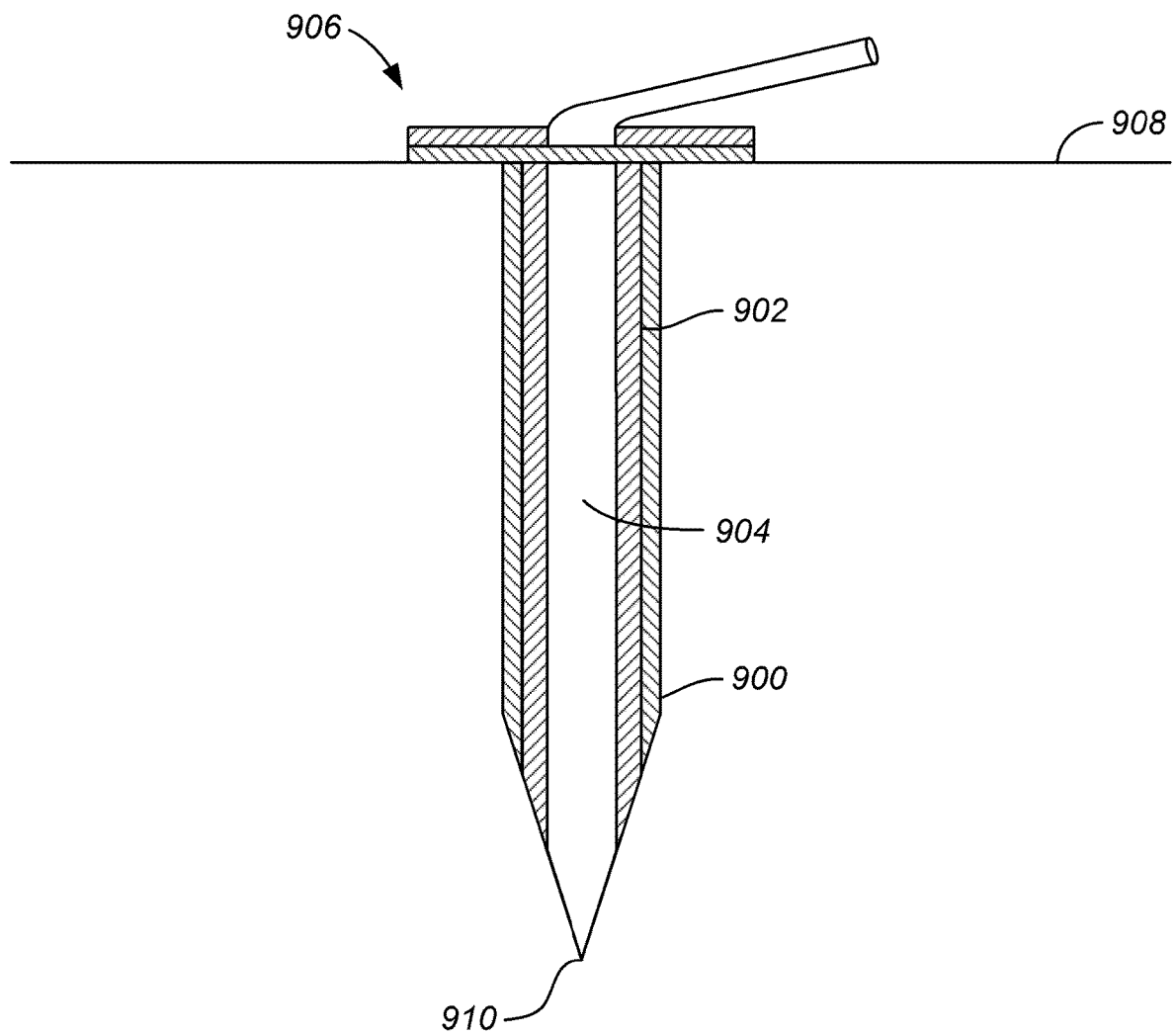
FIG. 9 is a continuous analyte sensor according to the present embodiments.
Figure 10:
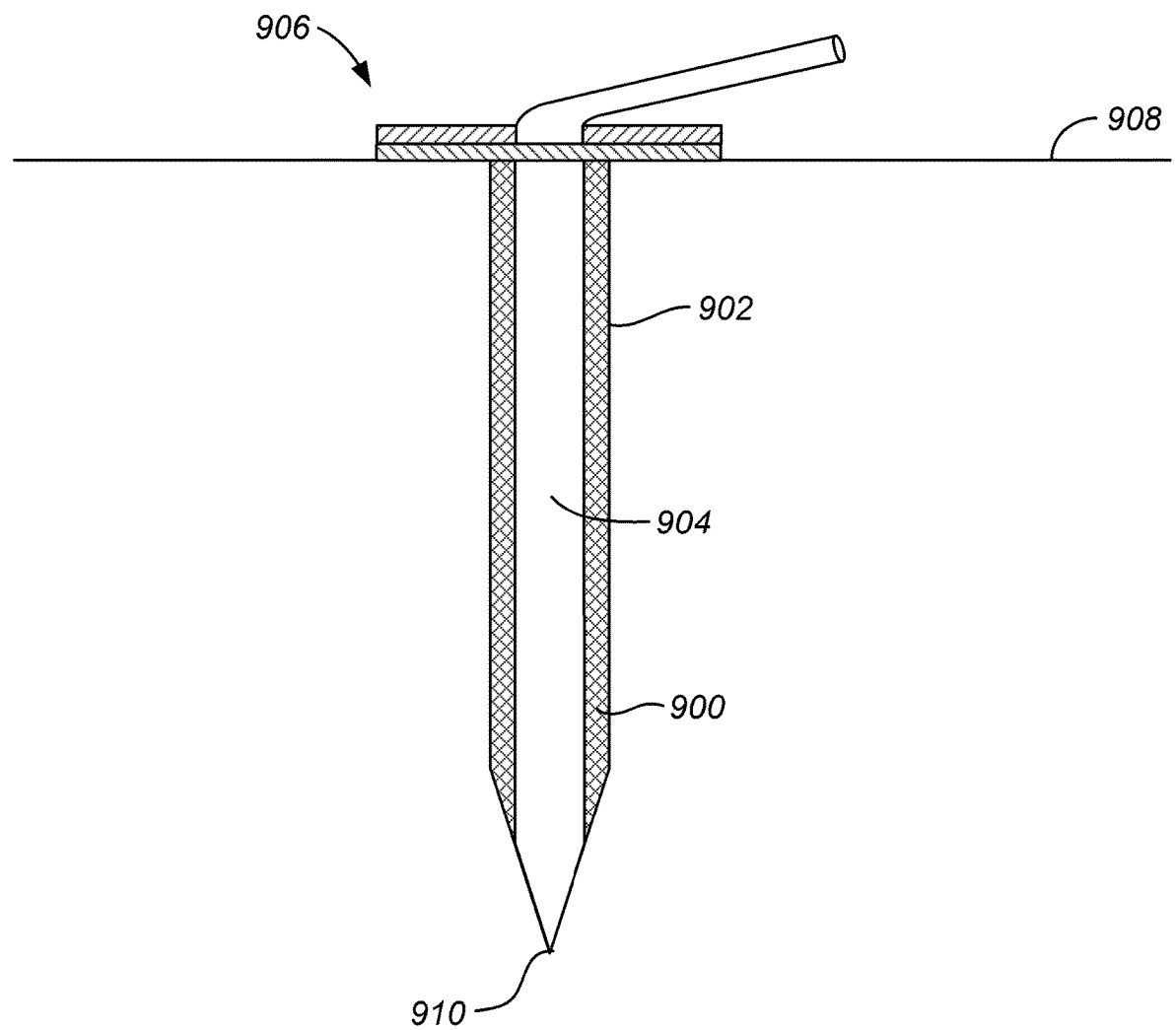
FIG. 10 is a continuous analyte sensor according to the present embodiments.

While FIGS. 9 and 10 illustrate embodiments in which a tip 910 of the sensor body 904 is exposed through the membrane 902/hardening agent 900, the present embodiments also contemplate that the tip 910 of the sensor body 904 could be covered by the membrane 902/hardening agent 900, similar to the embodiment of FIG. 8. Where the tip 910 of the sensor body 904 is exposed through the membrane 902/hardening agent 900, in certain embodiments the material of sensor body 904 is selected so that it does not react with a selected analyte and/or product of an analyte reaction. Such a reaction may create background current, which may adversely affect the performance of the sensor.

In one embodiment, the material of the sensor body 904 may be formed with a core that does not react with hydrogen peroxide. One such sensor body is platinum cladding on tantalum, where the tantalum core does not react with hydrogen peroxide or create additional background signal due to its electrochemical properties. The small amount of exposed platinum may not significantly contribute to the background signal.

In certain embodiments, the hardening agent 900 comprises cyanoacrylate. Cyanoacrylate is an advantageous material to use for this application, because it may permeate into the membrane, it cures quickly, it is very hard, and it may be machined after curing if needed. Cyanoacrylate may also deaden any enzyme that is on the tip, and coat any electrochemically active surfaces. Other example materials include epoxies and UV adhesives.

In one embodiment, a method of making a sensor device comprises coating a wire with a membrane. The coated wire is then cut to a desired length to form a sensor wire having a tip. Example methods for performing these steps are described in U.S. Patent Publication No. 2011-0027453-A1, the entire contents of which are hereby incorporated by reference herein. The coated sensor wire is then exposed to a hardening agent such that the membrane absorbs the hardening agent. Then, if necessary, the hardening agent is cured.

Exposing the coated sensor wire to the hardening agent may comprise dipping at least the sensor tip in a liquid bath of the hardening agent. After the sensor wire is withdrawn from the liquid bath, the membrane is cured to harden the hardening agent. Thereafter, the sensor tip may be sharpened to form a sharp point capable of piercing tissue. In alternative embodiments, the sensor wire may be sharpened prior to applying the membrane to the sensor wire, or after applying the membrane to the sensor wire but prior to applying the hardening agent.

In embodiments in which the sensor tip is sharpened after the membrane and hardening agent are applied, a deadening agent may be applied to the sharpened sensor tip to deaden any active surfaces exposed during the sharpening step. For example, platinum (Pt) or enzyme layer may be considered "active surfaces." In some embodiments, the deadening agent may comprise cyanoacrylate or a silane. Silanes may be particularly advantageous, since they may be lubricious, which may help the sensor penetrate into skin.

In embodiments that include a deadening agent, the deadening agent may be applied using vapor deposition, such as chemical vapor deposition (CVD) or physical vapor deposition (PVD). For example, a two-step application process may be used comprising a masking agent and then a spray agent followed by a rinse cycle.

In another embodiment, a method of making a sensor device comprises coating a wire with a membrane. The coated wire is then cut to a desired length to form a sensor wire having a tip. The coated wire is then exposed to a hardening agent such that the hardening agent covers the membrane. Additional process steps may then proceed similar to those in the foregoing embodiment, such as curing, sharpening, etc.

In another embodiment, a method of making a sensor device comprises cutting a wire to a desired length to form a sensor wire having a tip. The sensor tip is then sharpened to form a sharp point capable of piercing tissue. The sensor wire is then coated, including the sharpened sensor tip, with a membrane. The coated sensor wire is then exposed to a hardening agent such that the membrane absorbs the hardening agent. Additional process steps may then proceed similar to those in the foregoing embodiment, such as curing, etc.

In another embodiment, a method of making a sensor device comprises cutting a wire to a desired length to form a sensor wire having a tip. The sensor tip is then sharpened to form a sharp point capable of piercing tissue. The sensor wire is then coated, including the sharpened sensor tip, with a membrane. By coating the membrane, the host's fluid is separated from the enzyme by the protective membrane system, avoiding leaching of the enzyme into the host and ensuring a controlled pathway of diffusion of the host's fluid through the membrane system, including the enzyme. The coated sensor wire is then exposed to a hardening agent such that the hardening agent covers the membrane. Additional process steps may then proceed similar to those in the foregoing embodiment, such as curing, etc.

Stimulus Responsive Materials

In any of the embodiments described herein, the sensor body (e.g., wire) may be one or more "stimulus-responsive materials," which are materials that change at least one property responsive to a stimulus. For example, the sensor body may be a shape memory metal (or a more rigid metal like Ti) and/or a shape memory polymer. In such embodiments, the sensor body, while in a first state, may be held in a first configuration, which may be curved or straight. During or after the insertion process the wire transitions to a second state, which may be curved or straight.

In some embodiments, the sensor is in a straight, rigid state at a first temperature, and in a curved, flexible state at a second temperature. During use, the sensor body's original temperature is transformed to the first temperature (e.g., by heating or cooling), thereby causing the sensor to become straight and rigid, i.e., properties that are conducive for piercing of skin and tissue. After at least a portion of the senor pierces the skin and tissue, the sensor body reverts to a second temperature, at which it becomes curved and flexible, thereby providing comfort for the patient wearing the sensor.

In yet another embodiment, the sensor body comprises one or more "stimulus-responsive materials" that provide tissue compliant mechanical properties upon insertion and application of stimulus. It is advantageous to have the inserted body of the sensor conform to the natural tissue construct and modulus to reduce the injury and foreign body response caused by the presence of the sensor and body movement, as such injury or foreign body response may adversely alter the output of the sensor. For example, the tensile modulus of the sensor body may be between about 0.5-10 kPa.

Examples of material properties that may be changed responsive to a stimulus include, but are not limited to: hardness (e.g. from a hardness equivalent to that of a typical needle ex vivo, to softness closer in nature to subcutaneous tissue than a typical needle in vivo), shape, permeability, relative hydrophilicity, conformation of polymer orientation, etc. Examples of stimuli that may be used to change properties include, but are not limited to: temperature (e.g. 37° C. for in vivo change), pressure, hydration upon insertion to a subcutaneous environment, radiation (e.g. UV) provided by skin patch, electromagnetic stimulus, such as via a voltage, magnetic field, such as via inductive field, etc. Examples of stimulus-responsive materials include, but are not limited to: polymers, such as shape memory polymers, polyurethane, polyester, polyamide, polyacrylate, polyether, and copolymers thereof, alloys such as shape memory alloys (e.g., copper-aluminum-nickel (Cu—Al—Ni), nickel-titanium (NiTi), iron-manganese-silicon (Fe—Mn—Si), or copper-zinc-aluminum (Cu—Zn—Al)), etc.

One example includes a sensor body formed from polyurethane that changes its elastic modulus by 10× at 37° C. Other examples include a sensor body formed from a polyurethane copolymer that softens upon electrical stimulus or radiation (e.g., UV) stimulus applied right after sensor insertion, and others.

Sensors

Certain embodiments described herein provide various mechanisms for directly inserting a transcutaneous sensor into a host without the use of a separate applicator, i.e., other than the sensor device itself. Direct press insertion of a transcutaneous sensor (e.g., an electrode) having a wire-like geometry, especially a fine wire, may be technically challenging because of buckling risks associated with the sensor. Direct press insertion of a sensor also presents challenges relating to damage during the insertion process to the membrane disposed on the sensor. Without membrane protection, the membrane may be stripped off the sensor or be mechanically damaged during the insertion process. It is also desirable to avoid having exposed metal (or other electrically conductive material) at the tip of the sensor, because exposed metal may be electroactive and add background signal (noise) and/or cause the sensitivity of the sensor to vary. The embodiments described herein are designed to overcome the aforementioned challenges by providing miniaturized sensor devices capable of providing structural support (e.g., in the form of mechanical/structural properties such as column strength) for direct insertion of a transcutaneous sensor, and capable of protecting the membrane from damage during the insertion process.

In some embodiments, the sensor is designed with a configuration that enables printing of the electrodes (e.g., the working and/or reference electrode) onto the sensor body (e.g., the core). Unlike printing materials onto a planar substrate, printing materials (e.g., electrode materials) onto a wire presents unique challenges, particularly with wires intended for implantation with a diameter less than 400 microns (μm), such as the case with many of the sensor embodiments described herein. FIGS. 11-14 illustrate various sensor designs that enable printing of electrodes onto a sensor body formed with a wire shape.

Figure 11:
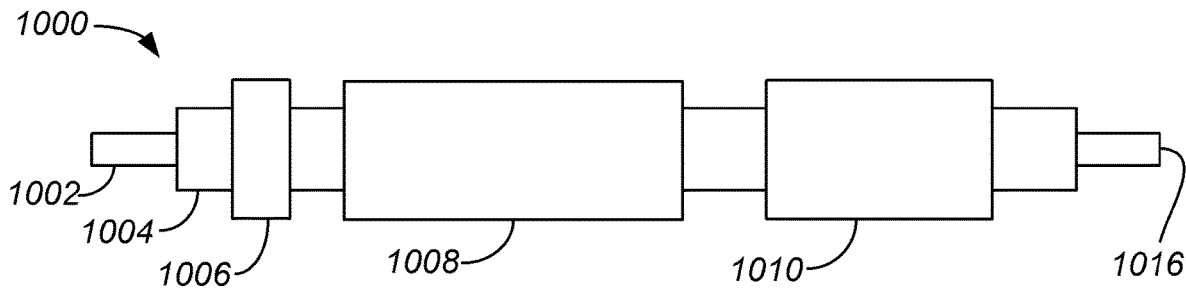
FIG. 11 is a schematic front elevation view of a sensor configured for direct press insertion according to the present embodiments.
Figure 12:
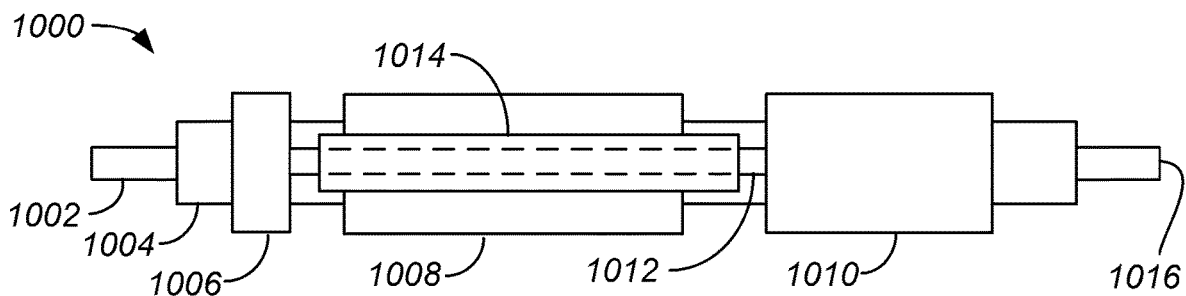
FIG. 12 is a schematic rear elevation view of the sensor of FIG. 11.

FIG. 11 is a front view of a sensor 1000, and FIG. 12 is a rear view of the sensor 1000. With reference to FIG. 11, the sensor 1000 comprises a conductive core wire 1002 with a nonconductive outer layer or jacket 1004. The core wire 1002 in some embodiments may be a conductive metal, such as and without limitation platinum, tantalum, platinum-iridium, or in other embodiments may be formed of a nonconductive material (e.g., a polymer or a non-conductive metal). In some embodiments, a portion of the core wire 1002 may form an electrode (e.g., a working, reference, or counter electrode). The nonconductive jacket 104 may be a polymer, such as and without limitation polyurethane, parylene, silicone, polyurethane, polyimide, or polyamide-imide. Axially spaced electrodes 1008, 1010 are provided over the nonconductive jacket 1004. In one embodiment, the sensor comprises a first electrode formed from the core wire 1002, a second electrode 1008, and a third electrode 1010. The electrodes 1008, 1010 may be, for example and without limitation, platinum, platinum-iridium, carbon, silver, silver/silver chloride, and/or any other material known to be used to form an electrodes (e.g., working, reference, or counter electrodes).

With reference to FIG. 12, the electrode 1008 does not extend around the entire circumference of the jacket 1004. The gap in the circumference permits a conductive trace 1012 to extend along the jacket 1004 between the electrode 1010 and a conductive component 1006 configured to join with a contact (not shown). A layer of electrically insulative material 1014 overlies the conductive trace 1012 to prevent contact between the conductive trace 1012 and the electrode 1008. In one example, the system comprises three electrodes, with the electrode 1008 comprising a reference electrode or counter electrode and the first and third electrodes 1002, 1010 comprising working electrodes. In another embodiment of a three-electrode system, the electrode 1010 serves as the reference or counter electrode, while the electrode 1008 serves as a working electrode. In another example, the system comprises two electrodes. In one such embodiment, the core wire 1002 does not serve as a working electrode, and thus may be formed of a nonconductive material. In this embodiment, one of the electrodes 1008 or 1010 serves as the working electrode, while the other electrode 1008 or 1010 serves as the reference or counter electrode.

As previously noted, the sensor 1000 of FIGS. 11 and 12 may advantageously be formed by printing, such as by 3-D printing. For example, the second and third electrodes 1008, 1010 may be printed on the exterior of the nonconductive jacket 1004. A distal end 1016 of the sensor 1000 may be sharpened to form a tissue piercing tip (not shown).

In embodiments in which the core 1002 does not serve as an electrode (e.g., in a two-electrode sensor system), the distal end 1016 of the core 1002 of the sensor 1000 may be made non-electroactive, so that it does not produce background signal. For example, the conductive core wire 1002 at the distal end 1016 can be inactivated through electrochemical polymerization. In other embodiments, the distal end 1016 of the senor may be capped by a non-conductive material, such as, for example, polyurethane, parylene, silicone, polyurethane, polyimide, polyamide-imide, or any other insulator(s).

Figure 13:
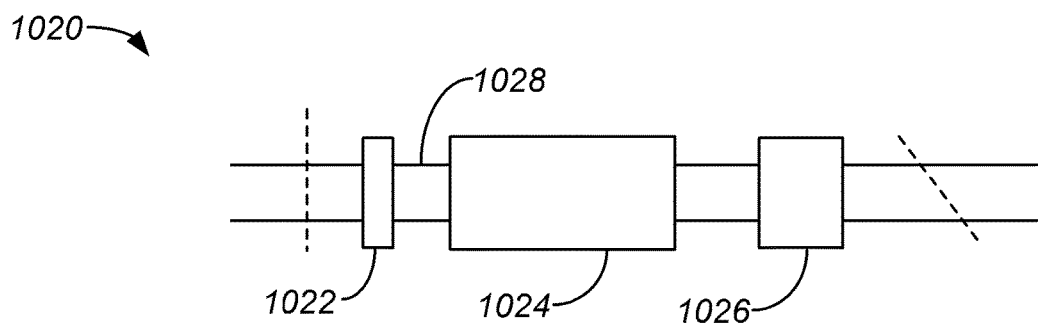
FIG. 13 is a schematic front elevation view of another sensor configured for direct press insertion according to the present embodiments.
Figure 14:
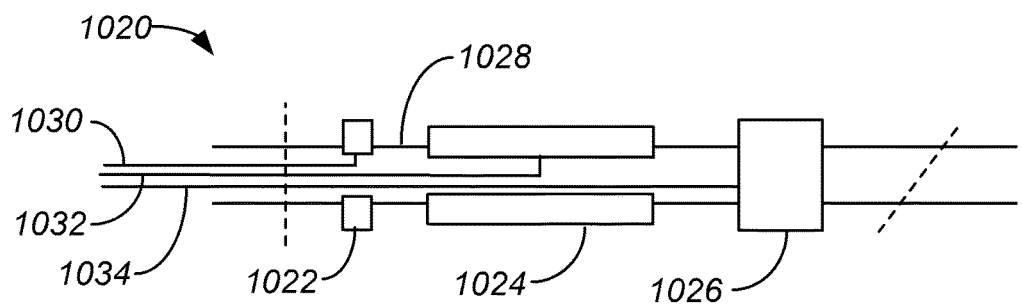
FIG. 14 is a schematic rear elevation view of the sensor of FIG. 13.

FIGS. 13 and 14 illustrate another sensor 1020 configured for direct press insertion according to the present embodiments. FIG. 13 is a front view of the sensor 1020, and FIG. 14 is a rear view of the sensor 1020. The sensor 1020 is somewhat similar to the sensor 1000 of FIGS. 11 and 12, except that the core wire 1002 may be omitted. Instead, the electrodes 1022, 1024, 1026 are provided over the nonconductive layer 1028 and electrically connected to sensor electronics (not shown) with conductive traces 1030, 1032, 1034 provided on the outer surface of the nonconductive layer 1028, as shown in FIG. 14. In the embodiment shown, the electrode 1024 does not extend around the entire circumference of the nonconductive layer 1028, thereby providing a conductive path for electrode 1026 around electrode 1024, without short circuit. Similarly, electrode 1022 also does not extend around the entire circumference of the nonconductive layer 1028, thereby providing conductive paths for electrodes 1026 and 1028 around electrode 1022. Electrodes 1022, 1024, 1026 may be a working electrode, a reference electrode, and/or a counter electrode. For example, in one embodiment, electrode 1026 serves as a working electrode, while electrode 1024 serves as a reference electrode, and electrode 1022 serves as a counter electrode. The elements illustrated in FIGS. 11-14, as well as every other figure provided herein, may not be drawn to scale and are provided merely to illustrate and help better understand the present embodiments.

Although the embodiments shown in FIGS. 11-14 are designed to have a configuration that enables printing of the electrodes, such sensor designs may, instead or in addition, be manufactured by any of a variety of techniques described herein or elsewhere.

Figure 15:
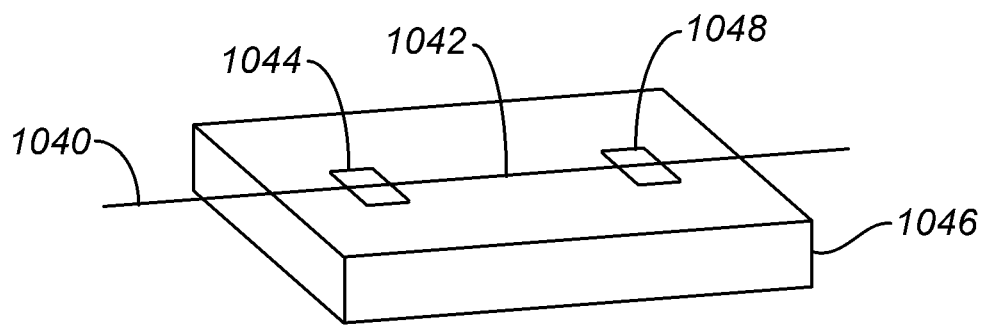
FIG. 15 is a schematic side perspective view of another sensor configured for direct press insertion according to the present embodiments.

Often, the sensor geometry and membrane properties may be difficult to control at the sharpened tip. There is also a potential for damage in this area. Accordingly, it would be desirable for the tip not to be a part of the working electrode. Furthermore, because electrode material (e.g., platinum) is often expensive, reducing the use of such material(s) (e.g., by not having the tip be part of the electrode) may be advantageous. FIG. 15 illustrates another sensor 1040 configured for direct press insertion according to the present embodiments. In this embodiment, the sensor 1040 includes a core wire 1042 and two electrodes 1044, 1048 provided along the wire 1042. In alternative embodiments, the sensor may comprise one, three, four, five, or more electrodes, with at least one of the electrodes being a working electrode, and at least one of the electrodes being a counter or reference electrode. The core wire 1042 may be formed of a conductive metal (e.g., tantalum or stainless steel) or a nonconductive material, such as a polymer or a nonconductive metal.

Referring again to FIG. 15, the electrodes 1044, 1048 may comprise a conductive material, such as, but not limited to, platinum, platinum-iridium, carbon, silver, silver/silver chloride, and/or any other material known to form an electrode (e.g., working, reference, or counter electrodes). In one embodiment, both electrodes 1044, 1048 are working electrodes and thus collectively form an array of working electrodes. In this particular embodiment, electrodes 1044, 1048 can share a conductive trace or pathway. In another embodiment, one electrode is a working electrode, and the other electrode is a reference or counter electrode. In some embodiments, the core wire 1042 may be surrounded by multiple layers of conductive materials with at least one insulating layer disposed between every two layers of conductive material. In these embodiments, the working electrodes each have their own electrical connection to an electrical contact through their individual conductive layers.

In one process for making the sensor 1040, the core wire 1042 may be positioned on a substrate 1046, and the electrodes 1044, 1048 may be printed (e.g., by pad printing) onto the core wire 1042 with a platinum paste. Any of a variety of printing techniques may be used, such as, but not limited to pad printing or 3-D printing. Depositing a layer of platinum paste selectively along the length of a non-conductive core wire 1042 may advantageously reduce material use and maintain a non-electroactive sensor tip. In some embodiments, in which the wire core 1042 is covered by multiple layers of conductive materials (with insulting layers disposed therebetween), these conductive materials may be formed of a conductive material that is not electroactive, such as tantalum, for example. A layer of platinum or silver/silver chloride, both of which are both conductive and electroactive, can then be pad printed onto these conductive layers to form an electroactive surface and thereby to form an electrode. By using this method, the sensor can be produced at lower cost, because the raw material costs for tantalum and other conductive, non-electroactive materials can be less than for materials that are both conductive and electroactive (e.g., platinum).

Often there is a tradeoff between ease of sensor insertion and patient comfort. A sensor formed of a rigid, inflexible material, all else being equal, is less likely to buckle during sensor insertion than a sensor that is soft and flexible. However, once implanted, because of its rigidity and the inflexibility, such a sensor may not be comfortable to the patient wearing the sensor, particularly if there is regular movement at the sensor site. Conversely, a sensor formed of a soft, flexible material is more likely to buckle during sensor insertion, and thus may not be a viable sensor design for a direct insertion implementation.

Figures 16, 17:
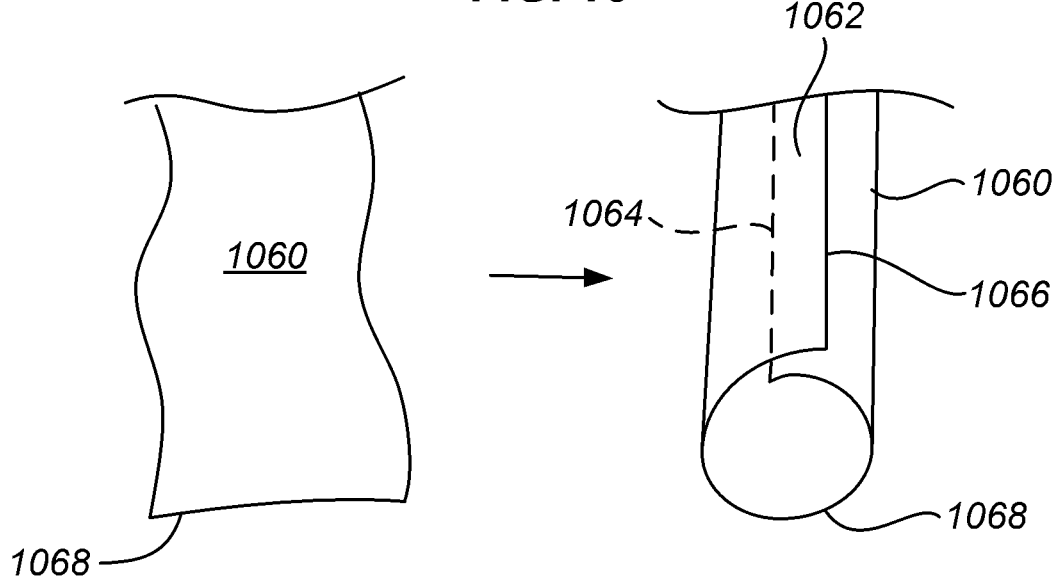
FIG. 16 is a schematic end perspective view of another sensor configured for direct press insertion according to the present embodiments.
FIG. 17 is a schematic end perspective view of the sensor of FIG. 16 after the sensor has been rolled into a cylinder.

FIGS. 16 and 17 illustrate one concept that overcomes the two above-described design criteria. With reference to FIG. 16, the sensor 1060 is formed on a flat substrate such as known planar substrate based sensors. The sensor 1060 may incorporate any of the sensor features (e.g., an electroactive surface and a membrane) described herein and any feature found in any conventional implantable sensor. Prior to sensor insertion, the flat sheet is rolled into a cylinder, as shown in FIG. 17. The rolled cylindrical form imparts a column strength sufficient for press insertion through the skin and tissue of the host during the implantation procedure. Rolling the planar sensor creates an overlap region 1062 where two opposite edges 1064, 1066 converge. The overlapping portions may be secured to one another, such as with an adhesive, a tie layer, a temporary bond, or the like, formed as would be appreciated by one skilled in the art. For example, an adhesive may be applied in the overlap region 1062, wherein the adhesive dissolves after the sensor 1060 is implanted. Upon dissolution of the adhesive, the rolled substrate may unroll to reassume its planar shape (FIG. 16). The planar sensor 1060 may be more pliable than the rolled sensor 1060, which may make the sensor 1060 more comfortable for the host. Alternatively, the adhesive may not completely dissolve, and may instead simply weaken, which may increase the flexibility or pliability of the sensor 1060 without allowing it to completely unroll. In the illustrated embodiment, the sensor 1060, in both its planar form (FIG. 16) and its rolled form (FIG. 17), includes a flat or straight leading end 1068. However, the sensor 1060, in either or both of its planar form and its rolled form, may include a beveled leading end such that the sensor mimics the shape of the leading (sharp) end of an insertion needle. In accordance with its unique design, the sensor 1060 illustrated in FIGS. 16 and 17 provides both strong resistance to buckling during sensor insertion and patient comfort after insertion.

In other embodiments, the column strength of the sensor may not be sufficient to completely prevent the possibility of buckling during sensor insertion. There are many possible reasons for this. For example, the sensor may be designed to focus on softness and flexibility to provide better comfort to the patient. To reduce the risk of buckling of the sensor during insertion, in some embodiments, a sheath may be used to provide the sensor with additional column strength during insertion.

Furthermore, the sheath may be designed to be formed, at least in part (e.g., the intraluminal surface), of a material with properties that reduce the risk of it damaging the membrane. Materials that may be used include, but are not limited to, silicone rubber, polyurethane, nylon, for example, or any other material that will not cause (or merely cause inconsequential) damage to the membrane. In addition to providing additional column strength, the sheath may also protect the membrane from contact with and (shear forces exerted by) skin and/or tissue, as the sensor slides past skin and/or tissue during deployment. In some embodiments, the intraluminal surface of the sheath is lubricous, i.e., has a low coefficient of friction, thereby reducing friction that may be present during retraction of the sheath. This protects the membrane from potential damage induced by tear and wear. The lubricious surface can be created by topical coating and/or blending the base material of the sheath with surface modifying additive(s) such as silicone, fatty acids, fluorinated polymers (e.g., PTFE), or other similar materials.

Figures 18, 19:
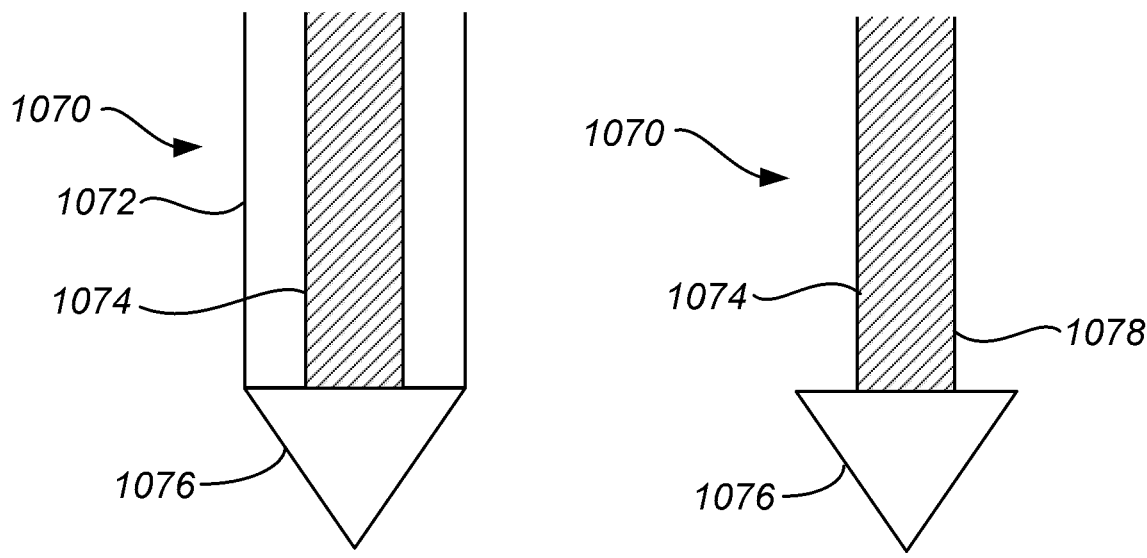
FIG. 18 is a schematic side elevation view of a sensor configured for direct press insertion according to the present embodiments.
FIG. 19 is a schematic side elevation view of the sensor of FIG. 18 after the retractable introducer sheath has been retracted.

With reference to FIG. 18, the sensor 1070 includes a retractable introducer sheath 1072 that covers the membrane 1074 during the insertion procedure. The introducer sheath 1072 not only protects the membrane 1074 during the insertion procedure, but also may support and provide additional column strength to the sensor 1070 for increased resistance to buckling. After insertion, the introducer sheath 1072 is retracted (FIG. 19), leaving the sensor 1070 with the uncovered membrane 1074 implanted within the host's skin and underlying tissue.

With reference to FIG. 19, in the illustrated embodiment the sensor 1070 includes a tissue piercing element 1076 having a diameter greater than that of the sensor body 1078. However, the relative dimensions of the illustrated components are only one example and are not limiting. The introducer sheath 1072 may have an outside diameter that is substantially equal to or less than the diameter of the tissue piercing element 1076. In alternative embodiments, a tissue piercing element may not be provided. A length of the introducer sheath 1072 may be substantially equal to, less than, or longer than the length of the sensor body 1078. As discussed above, following insertion of the sensor 1070, the introducer sheath 1072 is withdrawn from the skin. The introducer sheath 1072 may be withdrawn into a mounting unit (not shown). For example, the mounting unit may include a pull tab that may be manually (by the user) or automatically (by mechanical design triggered by connection of the electronics unit to the mounting unit) activated to remove the sheath.

Often, a membrane that is unprotected can become damaged and/or delaminated during sensor insertion. This can render the implantable sensor unusable. In some embodiments, the sensor is designed with a portion at the distal end that has a larger cross-sectional profile than other portions of the sensor. With this configuration, a shielding effect is created, whereby the above-described portion at the distal end shields (partially or completely) other portions of the sensor from having to contact tissue as the sensor slides past the tissue during sensor insertion. In some embodiments, one or more regions of the surface of the sensor body and/or the tissue piercing element may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and/or dimensions, in accordance with the intended application. Use of reservoirs or depots can increase the amount of bioactive agents the sensor is capable of carrying and delivering. In further embodiments, the sensor body and/or the tissue piercing element may be hollow with a cavity and connected via various passages with one or more openings on its surface, so that bioactive agents can be released from the cavity via the openings. In some embodiments, the sensor body and/or the tissue piercing element may comprise a pocket shaped and dimensioned to support a sensor with a membrane disposed thereon.

Figure 20:
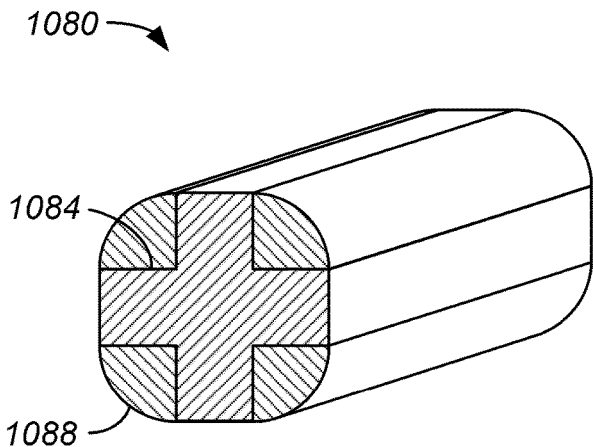
FIG. 20 is a schematic distal end perspective view of a sensor configured for direct press insertion according to the present embodiments.
Figure 22:
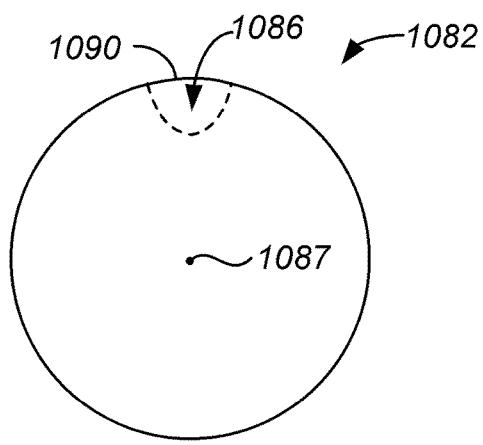
FIG. 22 is a schematic distal end elevation view of a sensor configured for direct press insertion according to the present embodiments.
Figure 21:
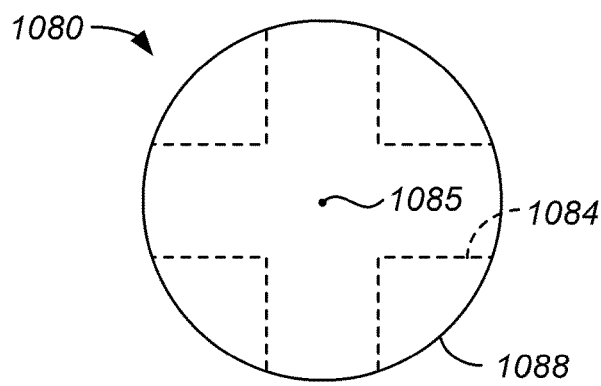
FIG. 21 is a schematic distal end elevation view of the sensor of FIG. 20.

FIGS. 20-22 illustrate embodiments that incorporate the foregoing concepts into their designs. As illustrated, each sensor 1080, 1082 includes a cross-section that defines at least one recessed area or trough that extends along the length of the sensor. With reference to FIGS. 20 and 21, the sensor 1080 defines a "plus sign" or x-shaped cross-section defining four evenly spaced troughs 1084 across the length of the sensor's longitudinal axis, except at the distal end 1085 (FIG. 21). At the distal end 1085, the sensor 1080 comprises a plurality of outer perimeter sections 1088 that provide the distal end of the sensor 1080 with a larger cross-sectional profile than the rest of the sensor 1080. With reference to FIG. 22, along its longitudinal axis, the sensor 1082 defines a circular cross-section having a single trough or cutout 1086, except at the distal end 1087 where there is no trough or cutout and where the cross-section is completely circular. The troughs 1084, 1086 may define spaces for disposing the electrodes, and the membranes that cover the electrodes, such that the electrodes and membranes are at least flush with or preferably recessed beneath an outer perimeter 1088, 1090 of the sensor 1080, 1082. Recessing the electrodes and membranes (or locating them flush with the sensor outer perimeter) protects the membranes from damage from shearing forces caused by the host's skin/tissue during the sensor insertion procedure by creating a spacing between the membranes and the host's skin and tissue. The troughs my not extend fully to the tip of the sensor body, to further protect the membranes during sensor insertion. After the sensor 1080, 1082 is inserted, settling/relaxation of the host's tissue increases the desired contact between the electrodes and the host's bodily fluids as needed for proper sensor functioning. The cross-sectional shapes illustrated in FIGS. 20-22 are merely examples. The present embodiments include sensors of any of a variety of cross-sectional shapes, including, without limitation, any general polygon, a star (having any number of points), a square, a pentagon, a heptagon, an octagon, an ellipse, or the like. The present embodiments may have any number of troughs for locating electrodes, for example, one, two, three, five, nine, twelve, or more.

Figure 23:
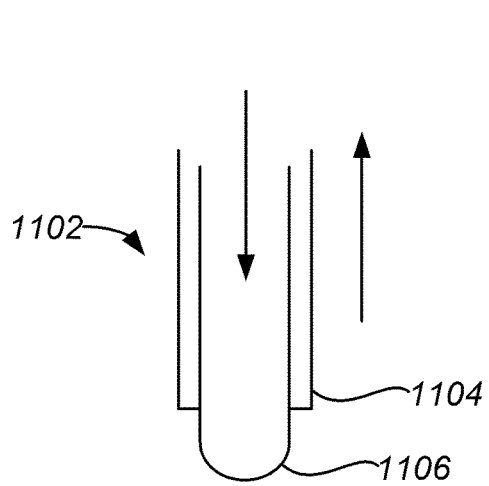
FIG. 23 is a schematic side elevation view of a sensor configured for direct press insertion according to the present embodiments.

FIG. 23 illustrates another sensor 1102 configured for direct press insertion according to the present embodiments. The sensor 1102 of FIG. 23 includes a protective sheath 1104 that covers the sensor 1102 during the insertion process. After the sensor 1102 is inserted, the sheath 1104 is retracted partially or fully to expose the sensor 1102 and/or the sensor tip 1106. Similar to the embodiment illustrated in FIG. 18, the protective sheath 1104 not only protects the membrane during the insertion procedure, but also may provide additional column strength for increased resistance to buckling. Furthermore, the sheath adds volume and cross-sectional area to the sheath/sensor assembly. Thus, when the sheath is removed (partially or fully), a small spacing may be created between the sheath and the surrounding tissue. This spacing then becomes occupied by the surrounding tissue as the tissue moves toward the sensor. While not wishing to be bound by theory, it is believed that a better tissue-sensor interface may be formed (for example, with less trauma, less inflammation, less risk of bleeding, etc.) when the tissue moves toward and contacts the sensor, rather than the other way around.

Figure 24:
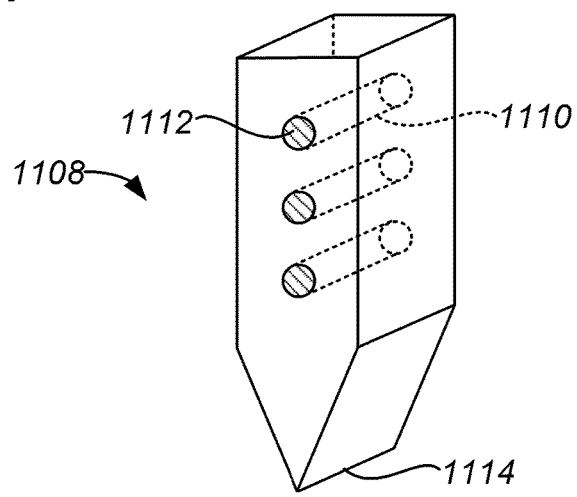
FIG. 24 is a schematic side perspective view of a sensor configured for direct press insertion according to the present embodiments.

FIG. 24 illustrates another sensor 1108 configured for direct press insertion according to the present embodiments. The sensor 1108 includes one or more through holes 1110, and the membrane(s) 1112 is/are disposed within the through holes 1110. In the illustrated embodiment, the sensor 1108 includes a tissue piercing distal tip 1114, but in alternative embodiments the tissue piercing distal tip 1114 may be omitted. In some embodiments, the through holes are shaped and dimensioned to enhance certain sensor characteristics. Although the through holes 1110 shown in FIG. 24 are substantially circular, in some embodiments, the through holes may be shaped or dimensioned differently. These differences may cause the electroactive surface in each of these through holes to behave differently and/or measure differently. For example, a deep through hole may contain a larger volume of interstitial fluid, compared to a shallow through hole. Accordingly, in some circumstances, the electrode corresponding to the deep through hole may provide a better signal-to-noise ratio or some other characteristic. On the other hand, because the volume of water displaced in the shallow through hole is a faster turnover rate, the electrode corresponding to the shallow though hole may have less lag issues, which can be important when a patient's analyte concentration is changing rapidly. In other embodiments, the shapes and dimensions of the different through holes may be designed differently to measure different species. For example, one of the through holes may have a shape and/or dimension that differs from another and that allows its corresponding electrode to better measure oxygen, rather than a different analyte (e.g., glucose).

Figure 25:
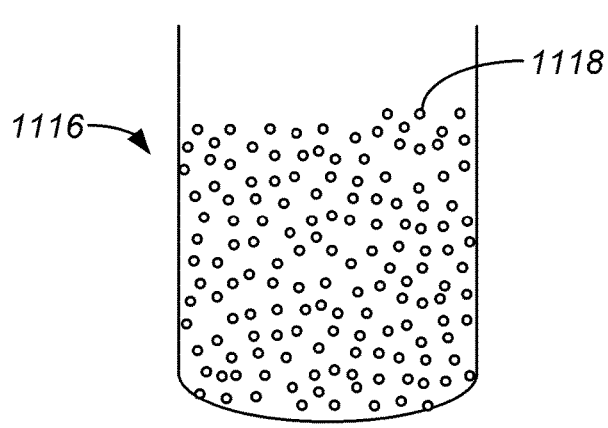
FIG. 25 is a schematic side elevation view of a sensor configured for direct press insertion according to the present embodiments.

Instead of, or in addition to through holes, the sensor may include one or more depressions 1118 in which the membrane(s) is/are disposed. For example, FIG. 25 illustrates another sensor 1116 configured for direct press insertion according to the present embodiments. The sensor 1116 shown in FIG. 25 includes a plurality of depressions 1118, or dimples, or pores, or cavities, etc. (hereinafter referred to as depressions 1118 for simplicity) in its outer surface. The depressions 1118 may be arranged in a pattern, or randomly arranged.

In some embodiments, the sensor 1116 may be covered by a particle-containing membrane system that comprises a conductive component dispersed in a non-conductive component (e.g., a polymer membrane material). The conductive component may comprise a plurality of conductive particles dispersed through the membrane system, some of which are covered at least in part by an enzyme material (e.g., glucose oxidase) configured to produce a species that is measured by the conductive particles to produce a signal. The conductive particles may comprise any of a variety of conductive, electroactive materials, such as, for example, platinum, platinum-iridium, graphite, silver, silver chloride, carbon, and/or conductive polymers.

In other embodiments, at least one of the depressions 1118, such as some of the depressions 1118 or all of the depressions 1118, may contain enzyme and/or membrane material. For example, the membrane may be flush with an outer surface of the sensor 1116, or recessed beneath an outer surface of the sensor 1116. Recessing the membrane(s) (or locating them flush with the sensor 1116 outer surface) protects the membranes from damage from shearing forces caused by the host's skin/tissue during the sensor insertion procedure by creating a spacing between the membranes and the host's skin and tissue. After the sensor 1116 is inserted, settling/relaxation of the host's tissue increases the desired contact between the electrodes and/or membranes and the host's bodily fluids as needed for proper sensor functioning. Alternatively, the membrane may protrude from the outer surface of the sensor 1116. The sensor 1116 shown in FIG. 25 may further include an outer bioprotective layer (not shown) or a bio-interface layer formed of a hydrophilic material to allow for easy sensor insertion with low push forces and reduced friction with surrounding tissue.

In some embodiments, the sensor may comprise a rigid outer layer that provides additional column strength to provide additional resistance to buckling during sensor insertion.

Figure 26:
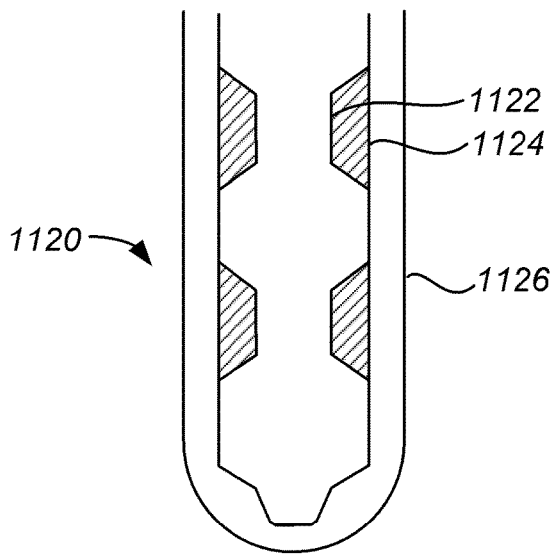
FIG. 26 is a schematic side cross-sectional view of a sensor configured for direct press insertion according to the present embodiments.

FIG. 26 illustrates another sensor 1120 configured for direct press insertion according to the present embodiments. The sensor 1120 includes a plurality of axially spaced depressions 1122 configured for receiving enzyme and/or membrane material 1124. The sensor 1120 further includes an outer layer 1126 of a material that is permeable to one or more selected analytes, including without limitation glucose. The outer layer 1126 not only shields and protects the underlying sensor 1120/membrane 1124 system during the sensor insertion procedure, but may also provide hardness and/or increased column strength for resistance to buckling during insertion. Because the outer layer 1126 is very permeable to one or more selected analytes, it does not have a substantial negative impact on the functionality of the sensor 1120.

Any of the embodiments described herein may incorporate an outer layer. Examples of materials for the outer layer 1126 include, without limitation, non-glucose limiting hydrogel, a polymer and/or carbohydrate film (e.g., a cellulose acetate film) or a metal film with micro porous structures or micro channels that permit analytes (e.g., glucose) to pass therethrough, or a lattice structure formed of metal or a hard polymer and formed with openings sized to permit analytes to pass therethrough. Polymers and/or sugars that may be used include, without limitation, cyanoacrylate polymers, polyurethanes, polyurethane urea, polyacrylates, polystyrene, polysulfone, polyetherketone, polycarbonate (e.g., polytrimethylcarbonate), polyimide, polyester, polyether, epoxide, maltose, PVP, polyethylene, L-lactide, or polycaprolactone.

As noted above, hardness of the outer layer 1126 may provide the sensor with additional column strength and enhance its ability to protect the membrane. With respect to any of the sensors described in this application that comprise an outer layer, the outer layer may be formed with a material that has a hardness on the Shore A scale of from about 30 to about 95, sometimes from about 70 to about 90, other times from about 50 to about 70.

Figure 27:
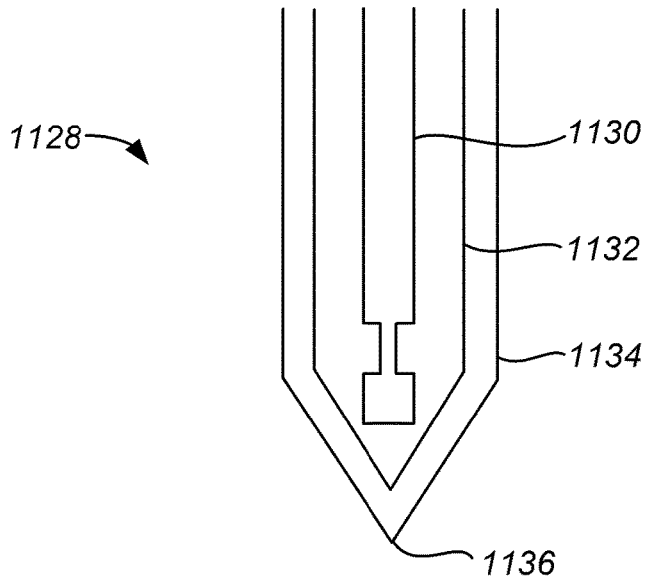
FIG. 27 is a schematic side elevation view of a sensor configured for direct press insertion according to the present embodiments.

FIG. 27 illustrates another sensor 1128 configured for direct press insertion according to the present embodiments. The sensor 1128 includes a sensor body 1130 with an overlying membrane 1132 and a protective outer layer 1134 disposed over the sensor 1128/membrane 1132 system. The protective outer layer 1134 not only shields and protects the underlying sensor 1128/membrane 1132 system during the sensor insertion procedure, but may also provide hardness and/or stiffness for increased column strength and resistance to buckling during insertion. The protective outer layer 1134 may comprise a dissolving material, such as a polymer, for example and without limitation. In some embodiments, the protective layer is formed of a material that is in a rigid state when dehydrated and/or at room (or lower than room) temperature. In this rigid state, the protective layer protects the membrane from damage during insertion and also improves the column strength of the senor, thereby enabling insertion. When exposed to body temperature and/or hydration, the protective layer becomes soft and flexible. In this state, the protective outer layer provides the patient wearer with better comfort. Examples of dissolving and/or degradable polymers include, without limitation, polyvinyl-pyrrolidone (PVP), polymerized sugar such as caramel, polyvinyl acetate, polyethylene glycol, polyesters, polyaminoacid, polycarbonate, polyanhydride, polylactic acid, polyglycolic acid, polydioxanone, polyhydroxybutyrate, polyhydroxyvalerate, polycaprolactone, polyanhydrides (e.g., aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, polyphosphazenes, and combinations or copolymers thereof and other similar polymers. Examples of non-polymeric dissolving materials include, without limitation, sugars (e.g., maltose), liquid oleic acid, vitamin E, peanut oil, and cottonseed oil, and other similar compounds. After the sensor 1128 is inserted and the protective outer layer 1134 dissolves, the sensor 1128 becomes more flexible (compared to the coated sensor 1128) for enhanced comfort of the host. Alternatively, the protective outer layer 1134 may comprise a material that does not completely dissolve, but rather softens after insertion into the host to enhance the comfort and wearability of the sensor 1128. Examples of softening materials include, without limitation, hydrophilic polymers, shape memory polymers including, but not limited to polyurethanes, polyesters, polyamides, polycarbonate, polyether, polylactic acid, polyglycolic acid, polydioxanone, polyhydroxybutyrate, polyhydroxyvalerate, polycaprolactone, polyanhydrides, polyorthoesters, polyaminoacids, pseudo-polyaminoacids, polycyanocrylates, or polyphosphazenes, and copolymers, blends, or combinations thereof and other similar polymers. The protective outer layer 1134 may be formed by dipping the sensor body 1130 and membrane 1132 in a liquid solution of the outer layer 1134 material, which subsequently solidifies and hardens. The dipping process may be tailored to produce a thinner coating at the tip 1136 to aid insertion. The liquid solution may be reactive and non-reactive, the reactive solution may be further reacted to increase the protective strength and mechanical support for insertion.

Figure 28:
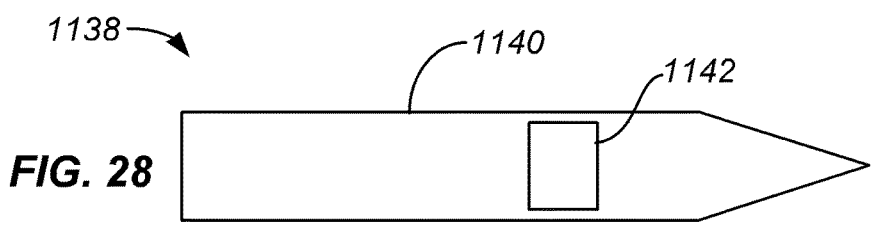
FIG. 28 is a schematic side elevation view of a sensor configured for direct press insertion according to the present embodiments.

FIG. 28 illustrates another sensor 1138 configured for direct press insertion according to the present embodiments. The sensor 1138 includes an outer layer 1140 of a rigid or stiff material. The outer layer 1140 covers substantially all of the sensor 1138, but includes at least one opening or window 1142. The window(s) 1142 is/are located over the electrodes such that the electrodes (and any membrane(s) overlying the electrodes) are exposed for contact with the tissue and/or bodily fluids of the host. The outer layer 1140 not only shields and protects the underlying sensor 1138/membrane system during the sensor insertion procedure, but may also provide hardness and/or increased column strength for resistance to buckling during insertion. Example materials for the outer layer 1140 include, without limitation, cyanoacrylate polymers, polyurethanes, polyurethane urea, polyacrylates, polystyrene, polysulfone, polyetherketone, polycarbonate (e.g., polytrimethylcarbonate), polyimide, polyester, polyether, epoxide, maltose, PVP, polyethylene, L-lactide, or polycaprolactone.

Figure 29:
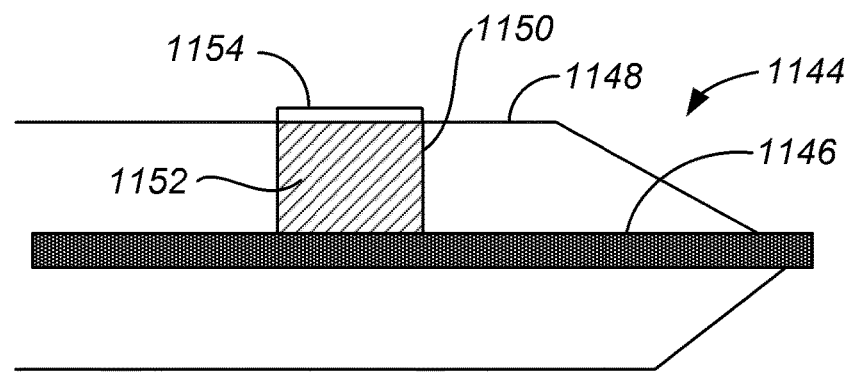
FIG. 29 is a schematic side elevation view of a sensor configured for direct press insertion according to the present embodiments.

FIG. 29 illustrates another sensor 1144 configured for direct press insertion according to the present embodiments. The sensor 1144 includes a conductive wire 1146, which may comprise a metal or any other conductive material. An outer coating 1148 is disposed over the wire 1146. The outer coating 1148 may have a greater thickness than the wire 1146. For example, the outer coating 1148 may be 1.5× thicker than the wire 1146, 2× thicker than the wire 1146, 2.5× thicker than the wire 1146, 3× thicker than the wire 1146, 3.5× thicker than the wire 1146, or the outer coating 1148 may have any thickness relative to the wire 1146. The outer coating 1148 may comprise a polymer such as, without limitation, cyanoacrylate polymers, polyurethanes, polyurethane urea, polyacrylates, polystyrene, polysulfone, polyetherketone, polycarbonate, polyimide, polyester, polyether, epoxide, polytetrafluoroethylene, and copolymers, combinations, or blends thereof.

The outer coating 1148 may include at least one opening or window 1150 corresponding to a location (or locations) of the electrode(s). For example, the window(s) 1150 may be formed by ablation, such as by laser ablation. Membrane 1152 may be disposed within the window(s) 1150, and may be recessed beneath an outer surface of the outer coating 1148. The recessed membrane 1152 is spaced from the host's skin and/or tissue during the sensor insertion process, thereby protecting the membrane 1152 from damage that could occur due to friction between the membrane 1152 and the host's skin and/or tissue.

The sensor 1144 may further include a highly permeable outer layer 1154 such as, without limitation, a hydrogel, overlying the membrane 1152 in the area(s) of the window (s) 1150. The highly permeable outer layer 1154 provides a mechanical buffer against damage to the membrane 1152 and/or electrode(s) located beneath the highly permeable outer layer 1154.

Advantageously, the sensor 1144 of FIG. 29 enables, but does not require, reel-to-reel continuous processing. Also, if desired, the entire sensor 1144 assembly, including all or some of the components shown in FIG. 29, can be further processed with laser ablation and/or a mechanical die to remove any excess material and/or to create a fresh edge to face the host's tissue.

Figure 30:
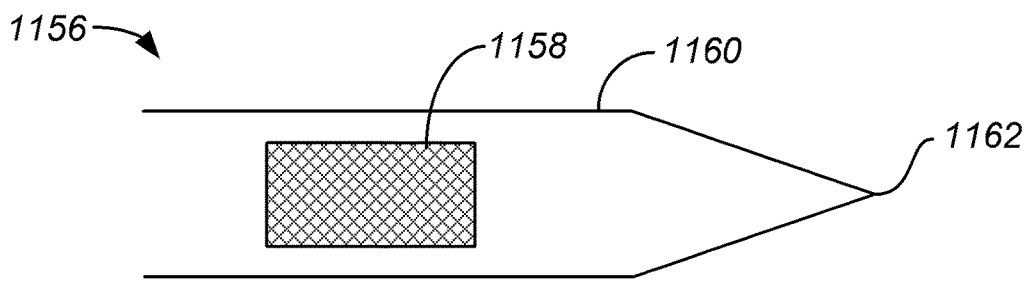
FIG. 30 is a schematic side elevation view of a sensor configured for direct press insertion according to the present embodiments.

FIG. 30 illustrates another sensor 1156 configured for direct press insertion according to the present embodiments. The sensor 1156 includes a membrane 1158 that is only applied in one or more regions of the sensor 1156. The membrane 1158 may be flush with an outer surface 1160 of the sensor 1156, recessed beneath the outer surface 1160 of the sensor 1156, or protruding from the outer surface 1160 of the sensor 1156. In embodiments in which the membrane 1158 is flush with or recessed beneath the outer surface 1160 of the sensor 1156, the membrane 1158 may be located within one or more openings or windows in the outer surface 1160 of the sensor 1156. The membrane 1158 may be applied to the sensor 1156 according to any desired process, such as printing and lithographic processing where the deposit of the membrane can be site specific. In some embodiments, printing is preferable, because it permits a very localized, controlled membrane deposition.

The outer surface 1160 of the sensor 1156 of FIG. 30, in areas other than the membrane 1158, may comprise a polymer, such as, without limitation, polytetrafluoroethylene (PTFE), cyanoacrylate polymers, polyurethanes, polyurethane urea, polyacrylates, polystyrene, polysulfone, polyetherketone, polycarbonate, polyimide, polyester, polyether, epoxide, and combinations, blends, or copolymers thereof. The distal end of the polymer may include a piercing tip 1162 configured to penetrate skin and/or tissue, and which has properties desirable for insertion. This sensor 1156 of FIG. 30 advantageously simplifies processes for making the sensor 1156 by not "dulling" the distal tip 1162 by applying membrane 1158 to the tip 1162. This sensor 1156 of FIG. 30 advantageously can be used in combination with other modes of membrane protection, such as any of the embodiments described elsewhere herein.

Manufacturing Techniques

One aspect of the present embodiments includes the realization that the materials used to form the membranes of analyte sensors are often soft, and thus tend to delaminate (i.e., peel back and sometimes peel off) as the sensor advances into skin and/or tissue. This problem is especially acute for sensors formed by a process in which the sensors are first coated with a membrane and then sharpened at the tip. This process exposes the sensor body, and leaves a thin coating of the membrane surrounding the sides of the sensor body at the tip. Some of the present embodiments provide solutions to this problem, including how to form the tip after applying the membrane, without damaging the tip, and while still maintaining the integrity of the tip.

With respect to sensor manufacturing, two approaches relate to whether the membrane coating step should precede the sharpened tip formation step, or whether the sharpened tip formation step should precede the membrane coating step. With the first approach, the membrane is coated onto the sensor workpiece prior to formation of the sharpened distal dip. With this first approach, the technical challenges involve finding techniques that permit creation of the sharpened tip, without causing damage to the membrane, and/or without creating excess membrane at the tip.

Figure 30A:
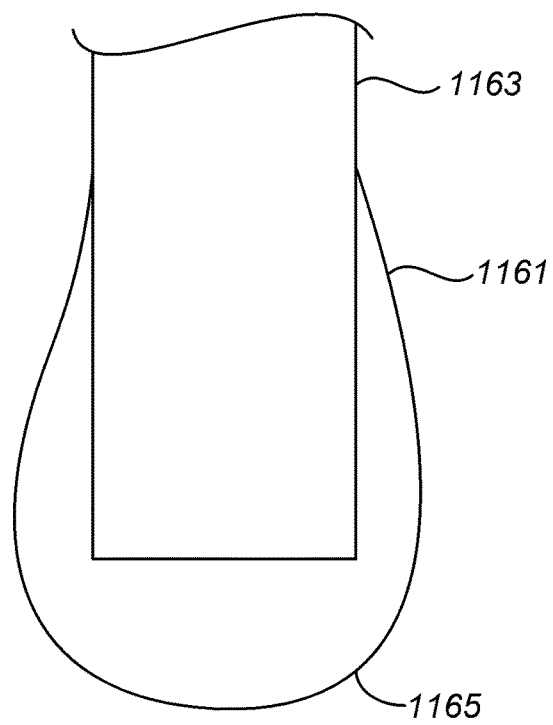
FIGS. 30A and 30B are schematic side elevation views of a process for making a sensor configured for direct press insertion according to the present embodiments.
Figure 30B:
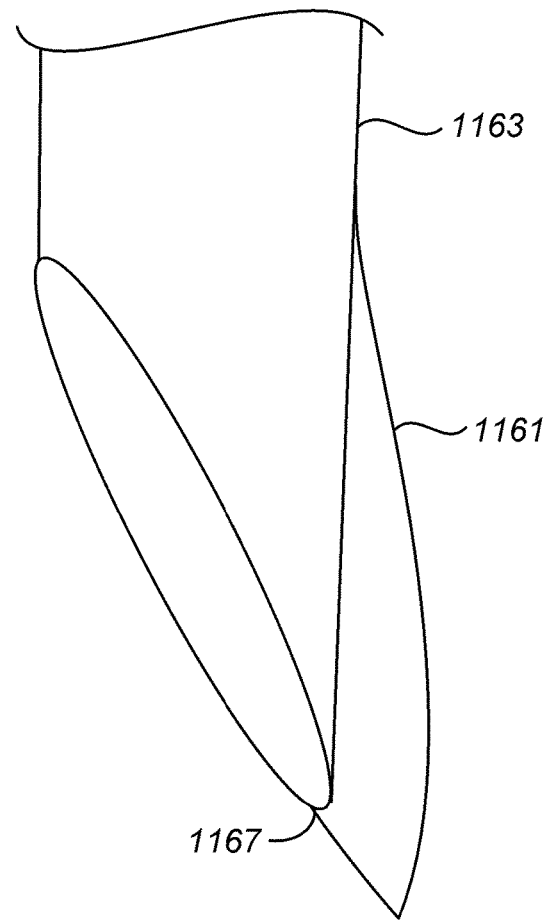

With reference to FIGS. 30A and 30B, in one method that adopts the first approach, a membrane 1161 is coated onto a sensor workpiece 1163. In some instances involving dipping, a bead 1165 (FIG. 30A) may form at one end of the workpiece 1163. Laser ablation, or mechanical cutting or grinding, for example, is then used to sharpen the distal end of the workpiece 1163 into a tip 1167 (FIG. 30B). By doing so, the bead 1165 on the distal end of the workpiece 1163 is removed. In the illustrated embodiment, sharpening the distal end of the workpiece 1163 comprises removing material from only one side of the workpiece 1163, thus forming a tip 1167 having a shape similar to a hypodermic needle point. In alternative embodiments, material may be removed from two opposite sides of the workpiece 1163 to form a wedge-shaped tip. In still further alternative embodiments, material may be removed from the workpiece 1163 about a full 3600 to form a cone-shaped tip.

Figures 31, 32, 33:
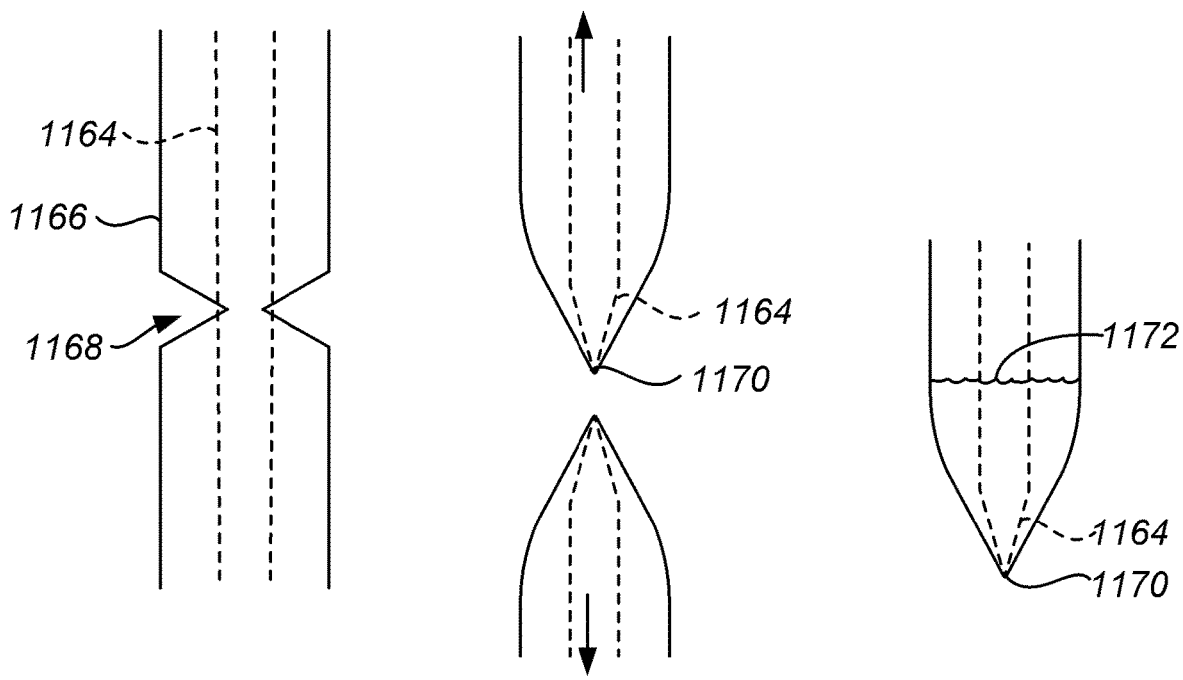
FIGS. 31-33 are schematic side elevation views of another process for making a sensor configured for direct press insertion according to the present embodiments.

FIGS. 31-33 illustrate another process for making a sensor that adopts the first approach. With reference to FIG. 31, a conductive wire 1164 includes a membrane coating 1166. The wire 1164 may be a metal, such as and without limitation, tantalum, platinum, stainless steel, platinum-iridium, silver, silver chloride, palladium, or any other metal.

The process of FIGS. 31-33 may include a step of applying the membrane 1166 to the wire 1164, or the process may commence with the wire 1164 already having been coated with the membrane 1166. An annular channel 1168 is then formed about the entire circumference of the coated wire 1164. The channel 1168 extends through the membrane 1166 and partially into the wire 1164. The channel 1168 may be formed by any process, such as mechanical cutting, grinding, laser ablation, heating, etc. In the illustrated embodiment, the channel 1168 has a v-shaped cross-section, but the channel 1168 may have any of a variety of cross-sectional shapes. This process has been found to prevent the membrane from covering the distal tip, which is advantageous, because in other processes membrane must be subsequently removed from the tip, which adds another process step.

With reference to FIG. 32, tension is applied to the coated wire 1164, either subsequent to the channel 1168 being formed, or simultaneously therewith. The tension induces strain in the wire 1164 in the region of the channel 1168, causing the wire 1164 to neck and eventually fracture. The necking process produces a sharp tip 1170 at the end of each of the two severed wire pieces 1164, and each of the sharp tips 1170 comprises the conductive wire material 1164, which may be a metal. In some embodiments, in addition to subjecting the channel 1168 of the wire 1164 to tension, the channel 1168 may also be subjected to heating. During or after the necking process, in some instances, the tips 1170 may be in a soft and/or malleable condition. In some embodiments, the surface of the tip may be subjected to further mechanical processing (e.g., through use of a sharpener, grinder, mold, etc.) to shape the distal tip so that it is sharp. The sharp tips 1170 advantageously can be used to pierce skin and/or tissue during the sensor insertion process.

With reference to FIG. 33, the sharp tips 1170 formed as a result of pulling the coated wire 1164 apart may subsequently be covered with a protective outer layer 1172 to protect the exposed conductive wire 1164 and/or the membrane 1166. The protective outer layer 1172 may comprise, for example and without limitation, a hardened polymer, such as cyanoacrylate polymers, polyurethanes, polyurethane urea, polyacrylates, polystyrene, polysulfone, polyetherketone, polycarbonate, polyimide, polyester, polyether, epoxide, polytetrafluoroethylene, and copolymers, combinations, or blends thereof. In addition, the protective outer layer 1172 may comprise any other protective layer materials described herein or elsewhere and also possess the mechanical properties described herein with respect to a protective outer layer. The protective outer layer 1172 may be applied with any process, such as solution-based coating where the reactive monomers and/or oligomers or non-reactive polymer are pre-dissolved, mixed or dispersed, extrusion, or printing, or any other process described herein or elsewhere related to coating.

Sensors formed by the process of FIGS. 31-33 advantageously include a sharp tip 1170 that can be used to pierce skin and/or tissue during the sensor insertion process. In certain embodiments, the membrane 1166 preferably does not overlap the sharp tip 1170 to avoid dulling the tip 1170, which, in turn, would render the tip 1170 less effective for piercing skin and/or tissue.

FIG. 34 corresponds to another process for making a sensor that adopts the first approach described above, in which the membrane is coated onto the sensor workpiece prior to formation of the sharpened distal dip. The process includes wire stock 1174 having a membrane coating 1176. The wire stock 1174 may be a material that is nonconductive and non-electroactive, such as and without limitation, polyurethanes, polyurethane urea, polyacrylates, polystyrene, polysulfone, polyetherketone, polycarbonate, polyimide, polyester, polyether, polyamide, and blends, combinations, or copolymers thereof. The process of FIG. 34 may include a step of applying the membrane 1176 to the wire stock 1174, or the process may commence with the wire stock 1174 already having been coated with the membrane 1176.

The wire stock 1174 shown in FIG. 34 is wound on a reel 1178, and the process of FIG. 34 is well suited for use in a continuous reel-to-reel process. However, the reel 1178 shown in FIG. 34 is just one example and is not limiting.

In the process of FIG. 34, the entire length of wire stock 1174 is coated with the membrane 1176. Portions of the membrane 1176 are then selectively removed at spaced locations along the wire stock 1174 as the wire stock 1174 is unwound from the reel 1178. The membrane 1176 may be removed at various locations in relation to the finished sensor, such as at the tip and/or at any other locations along the length of the finished sensor. In one non-limiting example, the membrane 1176 may be removed with a laser 1180 in a laser ablation process. After certain portions of membrane 1176 are removed, the wire stock 1174 is singulated at spaced locations to form a plurality of membrane-coated sensor wires. The membrane-coated sensor wires advantageously have no membrane 1176 at the sensor tip, where the membrane 1176 could blunt the tip and make the tip unsuitable for piercing skin and/or tissue.

In an alternative process, the singulation step itself may remove membrane 1176 from the sensor tip. Thus, for example, no separate step (besides singulating) may be performed to remove the membrane 1176 from the sensor tip. In yet another alternative process, the membrane removal and singulation steps may be performed as described above, but the wire stock 1174 may comprise a conductive material, such as a metal. After singulation, another material, such as a polymer cap or second coating, may then be applied to cover the sensor tip to prevent the tip from generating background signal when the sensor is inserted in the host.

There is a need for an implantable sensor that incorporates a layer of rigid material in the distal end of the sensor to not only protect the underlying membrane or to increase the sensor's column strength, as described elsewhere herein, but to inhibit shifting of the sensor membrane during sensor insertion. A typical sensor membrane is fragile and may be displaced during the process of sensor insertion, causing poor sensor performance. It is preferable for the sensor to remain in place on the sensor wire with little to no mechanical displacement relative to the sensor wire. Shifting of the membrane can cause the membrane to no longer cover the electrode(s). Similarly, in extreme cases, the membrane may become completely delaminated from the sensor. In addition, the sensor tip may be exposed before or during the insertion process, potentially generating background signal and/or causing variable sensor sensitivity. Further, it is sometimes desired to grind or otherwise process the tip of the sensor after the membrane has been applied. The grinding or other processing may expose the sensor wire, which can also generate background signal and/or cause variable sensor sensitivity. With reference to FIGS. 35-37, a process for making a sensor adopts the first approach described above of coating the membrane onto the sensor workpiece prior to forming the sharpened distal dip. The process involves a conductive wire 1182 having a membrane coating 1184. The wire 1182 may be a conductive material, including, but not limited to any conductive material disclosed elsewhere herein. In an alternative embodiment, a process similar to that shown in FIGS. 35-37 may involve a bare wire 1182 (i.e., with no membrane thereon) and a step of applying the membrane 1184 to the wire 1182. With reference to FIG. 36, a distal end 1186 of the membrane-coated wire 1188 is ground to produce a sharp tip 1190. Alternatively, the sharp tip 1190 may be produced by processes other than grinding, including any other sharpening, cutting, or singulating techniques disclosed herein or elsewhere. Through grinding or other processing, the distal end 1192 of the sensor wire 1182 is exposed.

With reference to FIG. 37, a coating 1192 is applied over the distal end 1186 of the membrane-coated wire 1188. The coating 1192 may be, for example, and without limitation, a hard polymer such as cyanoacrylate, or cyanoacrylate polymers, polyurethanes, polyurethane urea, polyacrylates, polystyrene, polysulfone, polyetherketone, polycarbonate, polyimide, polyester, polyether, epoxide, or any other material(s) capable of preventing detectable membrane movement during sensor insertion. The coating 1192 may be applied by any desired process, such as, and without limitation, dip coating, spraying, vapor deposition, extrusion, molding, or printing. The coating 1192 advantageously creates an impermeable barrier on the exposed end surface 1192 of the conductive sensor wire 1182, rendering the end surface 1192 non-electroactive, and therefore not capable of producing background signal or causing variable sensor sensitivity. The coating 1192 may also permeate into the membrane 1184 to harden or stiffen the membrane 1184 and cause it to more firmly adhere to the wire 1182, making the membrane 1184 more mechanically stable.

As noted above, with respect to sensor manufacturing, two approaches relate to whether the membrane coating step should precede the sharpened tip formation step, or whether the sharpened tip formation step should precede the membrane coating step. With the first approach, which is described above, the membrane is coated onto the sensor workpiece prior to formation of the sharpened distal dip. With a second approach, the workpiece is formed with a sharpened distal tip prior to the membrane coating process. With the second approach, one common technical challenge involves impeding or preventing membrane material from coating the sharpened distal tip and thereby dulling the tip, which in turn makes it more difficult (or more painful) for sensor insertion.

In some embodiments, materials (e.g., membrane or outer layer material) are coated onto a sensor workpiece (e.g., a sensor wire) using a dipping technique, wherein the sensor workpiece is dipped into a solution comprising a material that is to form a film or layer over the workpiece. Often, the distal end of the workpiece is the portion of the workpiece that is dipped first, because during the dipping process it is disposed at a lower vertical position than other portions of the workpiece. Because of gravity, the applied coating will typically sag toward the lowest end (i.e., the distal end) of the sensor workpiece, resulting in dulling of the distal tip, which in some embodiments is used to pierce skin and/or tissue. While not wishing to be bound by theory, it is believed that, holding everything else equal, with a coating formed from a low viscosity solution, the gravity-induced sagging issue may be worse, as compared to a high viscosity solution.

Figure 38:
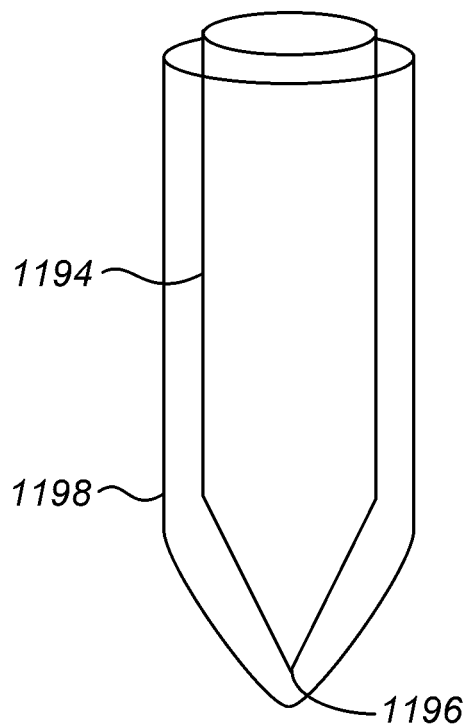
FIGS. 38 and 39 are schematic side elevation views of another process for making a sensor configured for direct press insertion according to the present embodiments.
Figure 39:
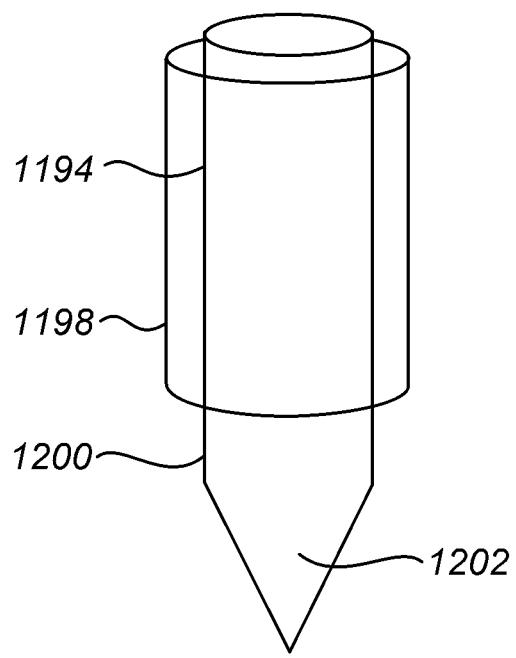

FIGS. 38 and 39 illustrate a process designed to overcome these technical challenges. With reference to FIG. 38, the process includes a sensor wire 1194 having a sharp distal tip 1196. The sensor wire 1194 is dipped, tip side down, in a membrane solution to form a membrane 1198 on the sensor wire 1194. After the membrane solution dries, a portion of the solidified membrane 1198 is removed at the distal end 1200 of the sensor wire 1194, as shown in FIG. 39. The membrane 1198 may be removed using any of a variety of processes, such as and without limitation, laser ablation, electropolishing, bead blasting, dry ice blasting, burning, or any other process. After the membrane 1198 is removed from the distal end 1200 of the sensor wire 1194, the exposed portion 1202 of the sensor wire 1194 may be coated with a protective layer (not shown), such as a hard polymer. Example materials for the protective layer include without limitation, cyanoacrylate polymers, polyurethanes, polyurethane urea, polyacrylates, polystyrene, polysulfone, polyetherketone, polycarbonate, polyimide, polyester, polyether, epoxide, and any other materials disclosed herein or elsewhere used to form the protective layer.

Figure 40:
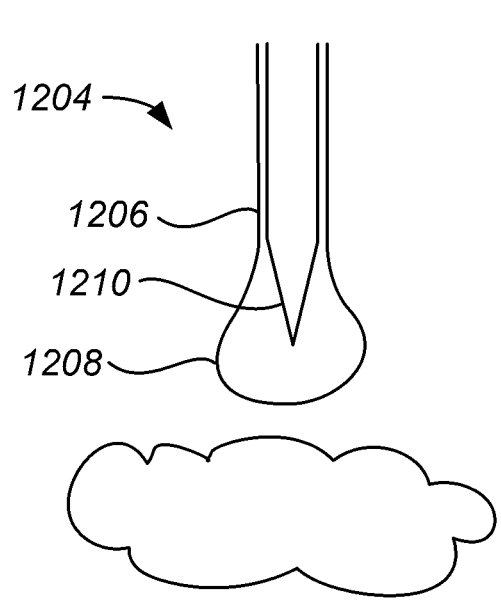
FIGS. 40 and 41 are schematic side elevation views of another process for making a sensor configured for direct press insertion according to the present embodiments.
Figure 41:
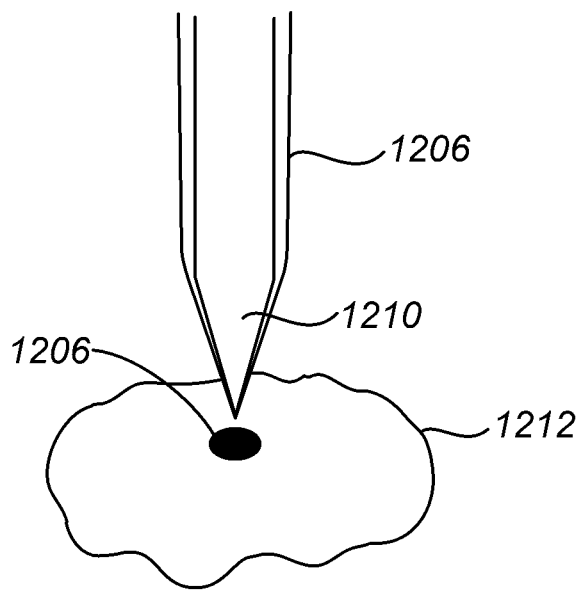

FIGS. 40 and 41 illustrate another process for removing membrane material from the distal end of the sensor wire. With reference to FIG. 40, the sensor 1204 has been dipped in a membrane solution, and the still wet solution 1206 forms a bead 1208 at the distal end 1210 of the sensor. With reference to FIG. 41, the distal end 1210 may be blotted or wiped with a fibrous body 1212 while the membrane solution 1206 is still wet. Some of the membrane solution 1206 at the distal end 1210 of the sensor 1204 is absorbed by the fibrous body 1212, as shown in FIG. 41. The fibrous body 1212 may comprise, for example and without limitation, a cloth, a cotton swab, a wicking pad, a sponge, etc. In another embodiment, instead of absorbing the excess membrane coating at the distal end, a tip may be used to contact the bead 1208 to break its surface tension, thereby causing some (if not all) of the excess membrane coating to drip off the distal tip. In certain embodiments, this procedure can be performed in conjunction with the above-described processes for absorbing excess membrane coating.

Figure 42:
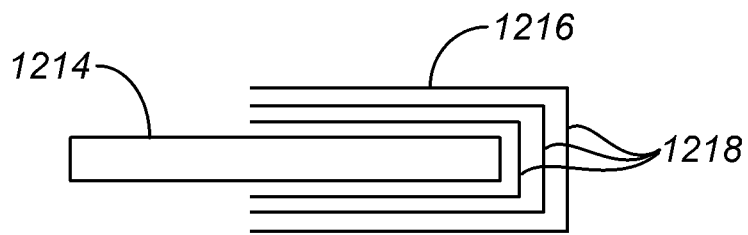
FIGS. 42 and 43 are schematic cross-sectional side elevation views of another process for making a sensor configured for direct press insertion according to the present embodiments.
Figure 43:
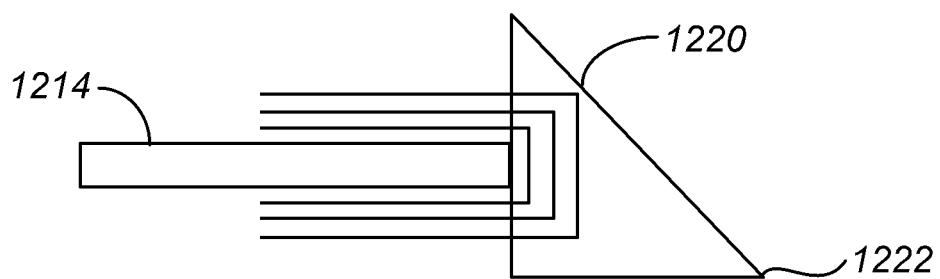

FIGS. 42 and 43 illustrate another process for making a sensor configured for direct press insertion according to the present embodiments. With reference to FIG. 42, the process includes a wire 1214 having a membrane coating 1216. The wire 1214 may be a conductive material, such as a metal, such as and without limitation, tantalum, platinum, or any other material described herein or elsewhere for use as a conductive and/or electroactive metal. The process of FIGS. 42 and 43 may include a step of applying the membrane 1216 to the wire 1214, or the process may commence with the wire 1214 already having been coated with the membrane 1216. The membrane 1216 may comprise a single layer, or a plurality of layers 1218 as illustrated.

With reference to FIG. 43, an end cap 1220 is applied to the tip of the membrane-coated wire 1214. The end cap 1220 comprises a material that is rigid, and preferably resistant to biofouling (e.g., resistant to protein adhesion to the membrane, which can reduce the membrane's permeability to analyte), and that can be formed or machined. Example materials include, without limitation, polytetrafluoroethylene (PTFE), cyanoacrylate polymers, polyurethanes, polyurethane urea, polyacrylates, polystyrene, polysulfone, polyetherketone, polycarbonate, polyimide, polyester, polyether, epoxide. The end cap 1220 may be applied to the sensor via any desired process, such as coating, injection molding, or mechanical interlocking from a preformed tip made from polymer or metal. The end cap 1220 may include a pointed tip 1222, or may be processed to produce a pointed tip 1222. The pointed tip 1222 is configured for piercing skin and/or tissue so that the sensor is configured for direct press insertion. The end cap 1220 advantageously facilitates direct press insertion while at the same time covering the distal end of the sensor wire 1214 so that it is not electroactive. The end cap 1220 may also provide a barrier that shields the distal end of the membrane 1216, making the membrane 316 less likely to be displaced from the end of the sensor wire 1214.

Figure 44:
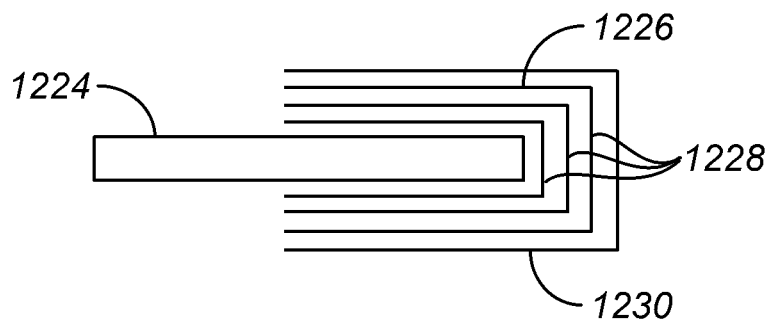
FIGS. 44 and 45 are schematic cross-sectional side elevation views of another process for making a sensor configured for direct press insertion according to the present embodiments.
Figure 45:
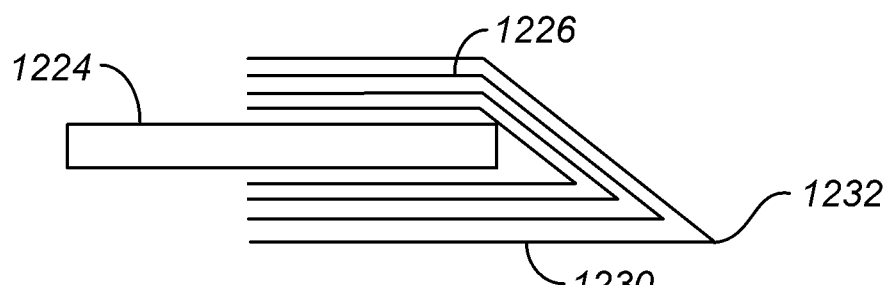

FIGS. 44 and 45 illustrate another process for making a sensor configured for direct press insertion according to the present embodiments. With reference to FIG. 44, the process includes a wire 1224 having a membrane coating 1226. The wire 1224 may be a conductive material, such as a metal, such as and without limitation, tantalum, platinum, silver, silver chloride, and any other conductive metal described herein or elsewhere. The membrane 1226 may include more than one layer 1228, such as two layers, three layers, four layers, five layers, or any number of layers. The process of FIGS. 44 and 45 may include a step of applying the membrane 1226 to the wire 1224, or the process may commence with the wire 1224 already having been coated with the membrane 1226. Applying the membrane 1226 to the wire 1224 may comprise printing, coating, vapor deposition, extrusion, or any other process described herein or elsewhere for coating a material onto a sensor workpiece. And, in the case of a multilayer membrane 1226, the process for forming each layer 1228 may be repeated any number of times until the desired number of layers is achieved. And, at least one layer 1228 of the multilayer membrane 1226 may be formed by a process that is different from a process or processes used to form at least one other layer 1228.

With further reference to FIG. 44, a rigid coating 1230 is formed at the tip of the sensor over the membrane 1226. The rigid coating 1230 may comprise cyanoacrylate polymers, polyurethanes, polyurethane urea, polyacrylates, polystyrene, polysulfone, polyetherketone, polycarbonate, polyimide, polyester, polyether, polyamide, epoxide, or any other rigid polymers described herein or elsewhere for forming an outer layer (e.g., a protective outer layer). A process for forming the rigid coating 1230 may comprise solution based coating, extrusion, or molding, or any other process described herein or elsewhere for coating a material onto a sensor workpiece.

With reference to FIG. 45, the rigid coating 1230 is shaped to produce a pointed tip 1232. The pointed tip 1232 is configured for piercing skin and/or tissue so that the sensor is configured for direct press insertion. The rigid coating 1230 with pointed tip 1232 advantageously facilitates direct press insertion while at the same time covering the distal end of the sensor wire 1224 so that it is not electroactive. The rigid coating 1230 also provides a barrier that shields the distal end of the membrane 1226, making the membrane 1226 less likely to be displaced from the end of the sensor wire 1224.

Figure 46:
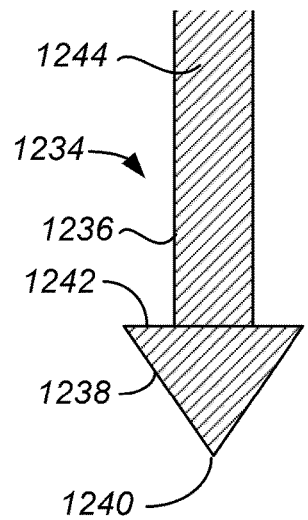
FIGS. 46-48 are schematic side elevation views of another process for making a sensor configured for direct press insertion according to the present embodiments.
Figure 47:
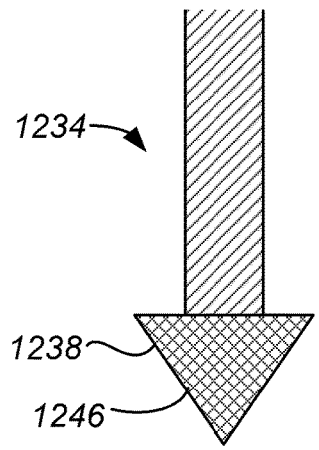
Figure 48:
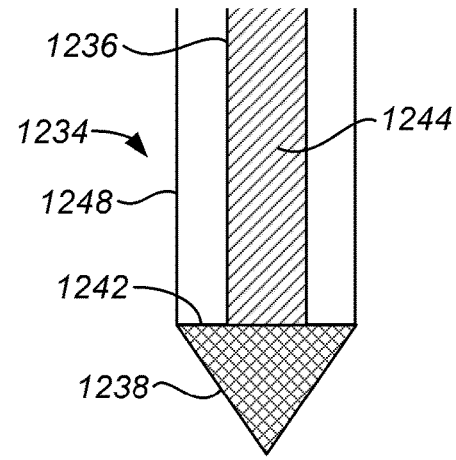

FIGS. 46-48 illustrate another process for making a sensor configured for direct press insertion according to the present embodiments. A sensor produced according to the process of FIGS. 46-48 advantageously does not expose the end of the sensor wire, such that the sensor wire at the tip is not electroactive and does not produce background signal or negatively affect the sensitivity of the sensor. With reference to FIG. 46, the sensor 1234 includes a sensor body 1236 and a piercing tip 1238. The tip 1238 includes a substantially triangular cross-section with a pointed distal end 1240. A proximal end 1242 of the tip 1238 defines a diameter that is greater than a diameter of the sensor body 1236. However, the illustrated shape of the sensor 1234 is just one example and is not limiting.

With further reference to FIG. 46, a membrane 1244 is applied to the sensor 1234, including the sensor body 1236 and the piercing tip 1238. The membrane 1244 may be applied by any desired method, such as dip coating, spray coating, brush coating, printing, extrusion, or any other method described herein or elsewhere for coating a membrane onto a sensor workpiece (e.g., sensor body). With reference to FIG. 47, a coating 1246 is applied to the piercing tip 1238 of the sensor 1234. The coating 1246 prevents the piercing tip 1238 from functioning as an electroactive surface. In some embodiments, the coating

1246 may comprise a material (e.g., silicone) that prevents a certain analyte (e.g., glucose) from passing therethrough. In other embodiments, the coating 1246 may comprise a material that inactivates the membrane 1244, for example, by denaturing the enzyme in the membrane 1244 needed for generating a signal. The coating 1246 may be applied by any desired method, such as any of the methods described herein or elsewhere for coating a material onto a workpiece. In yet other embodiments, instead of applying a coating 1246, the membrane 1244 may be inactivated by a light source or a heat source that can be used to denature the enzyme in the membrane 1244.

With reference to FIG. 48, a retractable introducer sheath 1248 is applied around the sensor body 1236. An outer diameter of the introducer sheath 1248 is substantially equal to, or less than, the diameter of the piercing tip 1238 at its proximal end 1242. The introducer sheath 1248 covers and protects the membrane 1244 during the sensor insertion procedure, making it less likely that the membrane 1244 will be displaced or damaged.

Figure 49:
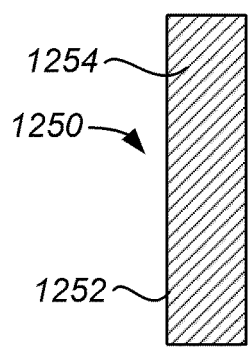
FIGS. 49-51 are schematic side elevation views of another process for making a sensor configured for direct press insertion according to the present embodiments.
Figure 50:
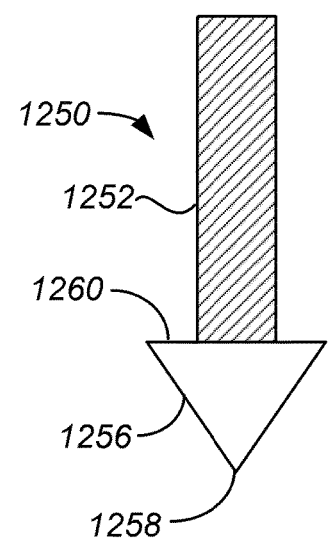
Figure 51:
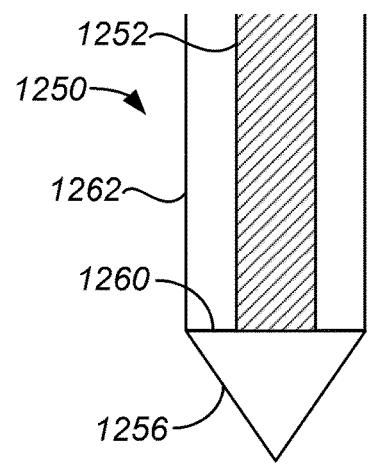

FIGS. 49-51 illustrate another process for making a sensor configured for direct press insertion according to the present embodiments. A sensor produced according to the process of FIGS. 49-51 advantageously does not expose the end of the sensor wire, such that the sensor wire at the tip is not electroactive and does not produce background signal or negatively affect the sensitivity of the sensor. With reference to FIG. 49, the sensor 1250 includes a sensor body 1252, and a membrane 1254 is applied to the sensor body 1252. The sensor body 1252 may be a conductive material, such as a metal, such as and without limitation, tantalum, platinum, or any other conductive metal disclosed herein or elsewhere. The membrane 1254 may be applied by any desired method, such as dip coating, spray coating, brush coating, printing, extrusion, and/or combinations thereof.

With reference to FIG. 50, a piercing tip 1256 is applied to the distal end of the sensor body 1252. The tip 1256 may be formed in a separate process, or formed as part of the same process for forming the sensor body 1252. The tip 1256 may be attached to the distal end of the sensor body 1252 by any desired process, such as mechanical crimping, press fitting, welding (such as ultrasonic welding), shrink tubing, application of heat, etc. The tip 1256 may comprise the same material as the sensor body 1252, or a different material. For example, the tip 1256 may be conductive, such as metallic, or non-conductive, such as non-metallic. Example materials for the tip 1256 include, without limitation, cyanoacrylate polymers, polyurethanes, polyurethane urea, polyacrylates, polystyrene, polysulfone, polyetherketone, polycarbonate, polyimide, polyester, polyether, polyamide, and epoxide.

The tip 1256 includes a substantially triangular cross-section with a pointed distal end 1258. A proximal end 1260 of the tip 1256 defines a diameter that is greater than a diameter of the sensor body 1252. However, the illustrated shape of the sensor 1250 is just one example and is not limiting.

With reference to FIG. 51, a retractable introducer sheath 1262 is applied around the sensor body 1252. An outer diameter of the introducer sheath 1262 is substantially equal to, or less than, the diameter of the piercing tip 1256 at its proximal end 1260. The introducer sheath 1262 covers and protects the membrane 1254 during the sensor insertion procedure, making it less likely that the membrane 1254 will be displaced or damaged. The introducer sheath 1262 may be metallic or non-metallic, for example. A non-metallic sheath may be made from, for example and without limitation, polyolefin, polyurethanes, polyurethane urea, polyacrylates, polystyrene, polysulfone, polyetherketone, polycarbonate, polyimide, polyester, polyether, polyamide, epoxide, or any other material.

The process of FIGS. 49-51 advantageously maintains sharpness of the piercing tip 1256 by not applying membrane 1254 to the tip 1256. And, because there is no membrane 1254 on the piercing tip 1256, it is less likely that the membrane 1254 will be breached and/or delaminate during the sensor insertion process.

FIG. 52 illustrates another process for making a sensor configured for direct press insertion according to the present embodiments. The sensor 1264 includes a sensor body 1266, a membrane 1268 over the sensor body 1266, and a sharp distal tip 1270 applied over the membrane 1268. The tip 1270 may be formed by any process, such as and without limitation, dipping, adhering, melting/cooling, solvent cast/drying, molding (e.g., extrusion or injection molding, press molding, or polymerizing in-situ in a mold), machining of a substrate piece, 3-D printing, casting, sintering, forging, machining, or other known methods of manufacturing implantable devices. In some embodiments, the material of the tip 1270 may comprise, for example, and without limitation, a biodegradable/bioabsorbable material. Example materials include, without limitation, polymers such as polyvinylpyrrolidone (PVP) and/or polyvinyl alcohol (PVA), sugars such as maltose, and others.

The process of FIG. 52 advantageously creates a sharp tip 1270 after the membrane 1268 has been applied to the sensor body 1266. Thus, no membrane 1268 is applied over the sharp tip 1270, which could dull the tip 1270. Another advantage, with respect to embodiments having a tip 1270 comprising a material that is biodegradable/bioabsorbable, is comfort of the host, since the tip 1270 dissolves after insertion. Using a biodegradable/bioabsorbable tip can avoid the potential of leaving the tip inside the body, if the tip becomes detached from the sensor.

One aspect of the present embodiments includes the realization that applying a membrane to a sharp sensor tip presents challenges. For example, the sharp tip can breach the membrane and/or cause the membrane to delaminate, particularly when the sensor is subjected to frictional forces during the process of sensor insertion. Also, applying a membrane to a sharp sensor tip may dull the tip, rendering the tip less effective for direct press insertion of the sensor. Some of the present embodiments provide solutions to these problems, including how to apply the membrane to a sharp tip, without damaging the tip, and while maintaining the integrity of the tip.

FIG. 52A corresponds to another process for making a sensor configured for direct press insertion according to the present embodiments. The sensor 1269 includes a core wire 1271, and an electrically insulative layer 1273 over the core wire 1271. The insulative layer 1273 includes a gap 1275 that exposes a portion of the core wire 1271 just proximal of the distal tip 1277. A conductive layer 1279 is disposed over the insulative layer 1273 proximal of the gap 1275, but not distal of the gap 1275. The conductive layer 1279 may comprise for example, and without limitation, silver chloride. A membrane coating 1281 covers the conductive layer 1279, the exposed portion of the core wire 1271, and the portion of the insulative layer 1273 distal of the gap 1275. The distal tip 1277 of the core wire 1271 is sharpened prior to application of the membrane coating 1281.

FIG. 53 corresponds to another process for making a sensor configured for direct press insertion according to the present embodiments. The sensor 1272 includes a sensor body 1274 having a core 1276 and an outer layer 1278, and a membrane 1280 applied over the outer layer 1278, but not over the core 1276. The core 1276 and the outer layer 1278 comprise different materials. The core 1276 comprises a material that is rigid enough to form a piercing tip 1282, and may comprise a material that does not necessarily adhere well to (or even repels) the membrane 1280. For example, the material of the core 1276 may have a low surface energy and be non-wetting. By contrast, the outer layer 1278 comprises a material to which the membrane 1280 readily adheres.

Example materials for the core 1276 include, without limitation, stainless steel, titanium, tantalum and/or a polymer, and the first layer may comprise platinum, platinum-iridium, gold, palladium, iridium, graphite, carbon, a conductive polymer, and/or an alloy. Alternatively, the core 1276 may comprise a material that is pretreated or coated with another material that repels coating of the membrane 1280. Example materials for the pretreated core 1276 include, without limitation, materials that discourage the formation of films, such as polytetrafluoroethylene. The pretreatment may comprise, for example, and without limitation, engineering the surface of the core 1276 to facilitate breaking up of film. Alternatively, the pretreatment may comprise a coating with a hydrophobic substance (e.g., a superhydrophobic material), if the portion of the coated membrane first deposited, is hydrophilic, or conversely a coating with a hydrophilic substance (e.g., a superhydrophilic material), if the portion of the coated membrane first deposited, is hydrophobic. The hydrophobicity of a surface can be measured by its contact angle with water. The greater the water contact angle, the higher the hydrophobicity of the surface. Generally, if the water contact angle is smaller than 90°, the surface is considered hydrophilic, and if the water contact angle is larger than 90°, the surface is considered hydrophobic. In some embodiments, the surface of the pretreated core 1276 is hydrophobic and has a contact angle greater than about 120°, sometimes greater than about 135°, and sometimes greater than about 160°. In some embodiments, the surface of the pretreated core 1276 is hydrophilic and has a contact angle less than about 60°, sometimes less than about 45°, and sometimes less than about 30°.

Example materials for the membrane material include, without limitation, any material that may be used to form a membrane on an analyte sensor. Membrane materials that may be used include, but are not limited to, those described in U.S. Patent Publication No. 2009-0247856-A1, which is incorporated by reference herein in its entirety. The membrane described in U.S. Patent Publication No. 2009-0247856-A1 may also be used to form a membrane on any of the sensors described herein.

In the process corresponding to FIG. 53, the outer layer 1278 and/or membrane 1280 may be applied to the core 1276 or the sensor body 1274 by any of a variety of coating techniques, such as, for example, dipping, spraying, electro-depositing, dipping, casting, or a combination of these techniques. In some embodiments, the core 1276 may be advanced through a series of stations with any of a variety of other transport mechanisms, such as, for example, a robotic system, a conveyor system, and other like systems. These other transport mechanisms may be used in combination with (or as an alternative to) a reel-to-reel system. For example, in one embodiment, a reel-to-reel system is used to move the core 1276 in the form of an elongated body, before it is singulated into individual workpieces, and a robotic system is used to move the individual workpieces after the singulation process. Processes that may be used to apply the outer layer and/or membrane include, but are not limited to, those described in U.S. Patent Publication No. 2011-0027458-A1, which is incorporated by reference herein in its entirety.

The sharp distal tip 1282 may be formed by any of a variety of techniques, such as, for example and without limitation, cutting by mechanical grinding, diamond wire, high-speed milling, abrasive water jet cutting, electric discharge machining by wire or plunge, electrochemical etching, electrochemical polishing, electrochemical machining, stamping, laser cutting, or any other methods for cutting and/or shaping a workpiece. In certain embodiments, the sharp distal tip 1282 is formed by electrochemical grinding, which is a process that removes electrically conductive material by grinding with a negatively charged abrasive grinding wheel, an electrolyte fluid, and a positively charged workpiece (which in this case is the sensor 1272). Material removed from the workpiece remains in the electrolyte fluid, which may remove residual coatings formed on the surfaces of the sharpened distal tip. The techniques described above (e.g., electrochemical etching, electrochemical grinding) may also be used to form a sharp distal tip on any of the sensors described herein.

FIGS. 54 and 54A correspond to another process for making a sensor configured for direct press insertion according to the present embodiments. The sensor 1284 includes a sensor body 1286 and a membrane 1288 applied over the sensor body 1286. With reference to FIG. 54A, the membrane 1288 comprises a plurality of layers 1290, wherein a thickness of each layer 1290 is less than a thickness of a typical single-layer membrane, but the thickness of the aggregated layers 1290 is substantially equal to a thickness of a typical single-layer membrane. For example, the membrane 1288 may comprise two layers 1290, or three layers 1290, or four layers 1290, or any other number of layers 1290. A thickness of each layer 1290 may be from about 0.5 microns to about 10 microns, sometimes from about 1 micron to about 5 microns, or any other thickness suitable for application in an implantable analyte sensor. A thickness of the layers 1290 may vary, wherein one or more of the layers 1290 are thicker or thinner than other layers 1290. In the process corresponding to FIGS. 54 and 54A, applying the membrane layers 1290 to the sensor body 1286 may comprise any of a variety of coating techniques, such as, for example, printing, dipping, extrusion, spraying, electro-depositing, casting, or combinations thereof.

Figure 55:
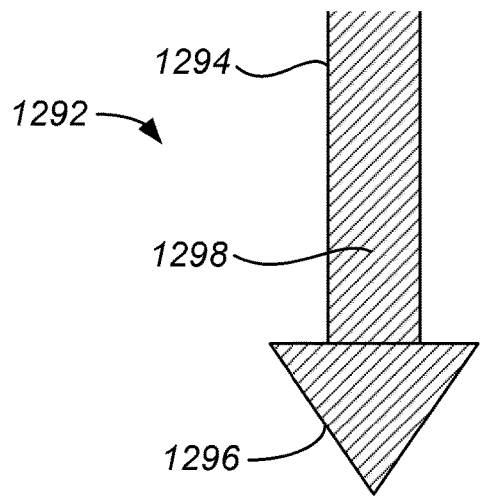
FIGS. 55 and 56 are schematic side elevation views of another process for making a sensor configured for direct press insertion according to the present embodiments.
Figure 56:
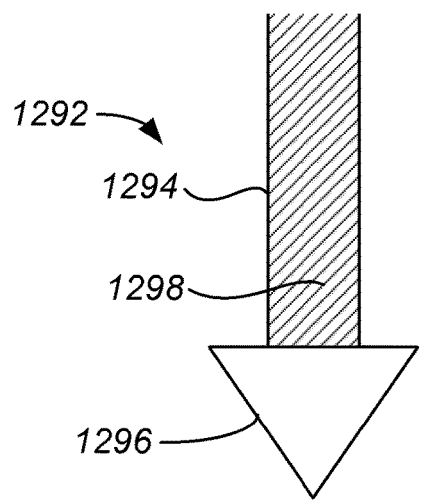

FIGS. 55 and 56 illustrate another process for making a sensor configured for direct press insertion according to the present embodiments. With reference to FIG. 55, the sensor 1292 includes a sensor body 1294 with a sharp distal tip 1296. A membrane 1298 is applied over the sensor body 1294 and the tip 1296. Then, with reference to FIG. 56, the membrane 1298 is removed from the tip 1296, but not from the sensor body 1294. The membrane 1298 may be removed using any process, such as, without limitation, etching (e.g., dry, wet, reactive-ion, and/or chemical etching), laser ablation, mechanical stripping (such as abrading), UV light, or any other process for removing polymer material from a substrate.

Figure 57:
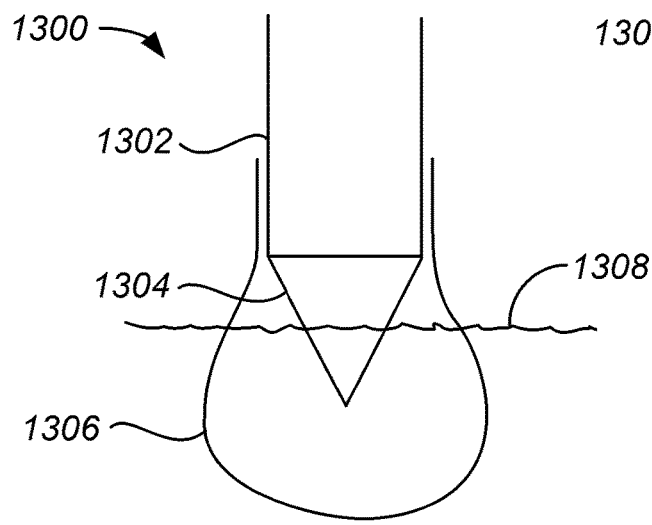
FIGS. 57 and 58 are schematic side elevation views of another process for making a sensor configured for direct press insertion according to the present embodiments.
Figure 58:
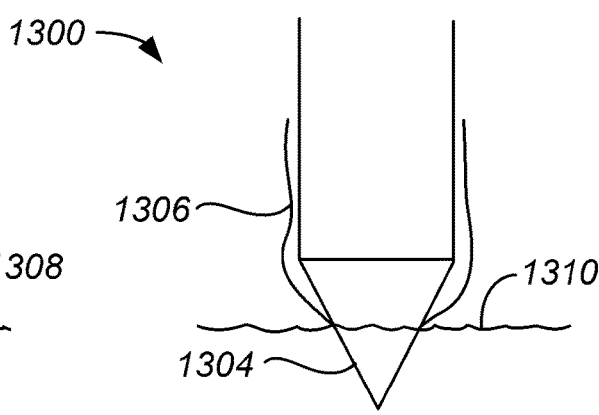

FIGS. 57 and 58 illustrate another process for making a sensor 1300 configured for direct press insertion according to the present embodiments. With reference to FIG. 57, the sensor 1300 includes a sensor body 1302 with a sharp distal tip 1304. A membrane 1306 is applied over the sensor body 1302 and the tip 1304 by dipping in a membrane solution 1308. Due to gravity, the deposited membrane 1306 forms a "bead" in the area of the distal tip 1304. This geometry is typical when a membrane is applied with a dipping process, particularly when the membrane solution has a certain viscosity. In certain instances, the bead of membrane 1306 material over the distal tip 1304 disadvantageously dulls the tip 1304. Thus, with reference to FIG. 58, the process includes a step of dipping the membrane-covered distal tip 1304 in a solvent 1310 to dissolve the membrane 1306 and substantially remove the membrane 1306 material from the sharp tip 1304 of the sensor 1300. The solvent 1310 may comprise, for example, and without limitation, tetrahydrofuran (THF), dimethylacetamide (DMAC), hexafluoroisopropanol, methylene chloride, methanol, methylethylketone, toluene, and dimethyl formamide. In some embodiments, the distal bead can also be avoided by removing the excess material at the tip before solidifying via wiping, blowing, etc.

Figure 59:
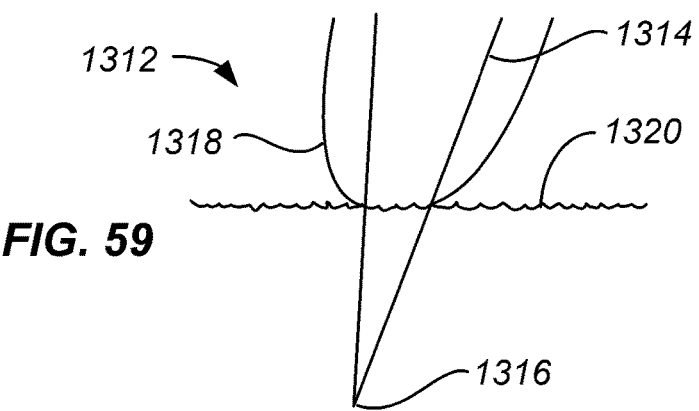
FIG. 59 is a schematic side elevation view of another process for making a sensor configured for direct press insertion according to the present embodiments.

FIG. 59 corresponds to another process for making a sensor configured for direct press insertion according to the present embodiments. The sensor 1312 includes a sensor body 1314 with a sharp distal tip 1316. A membrane 1318 is applied over the sensor body 1314 and the tip 1316 by dipping in a membrane solution (not shown). Then, before the membrane solution dries, the tip 1316 is dipped in a release agent 1320 that prevents the membrane 418 from adhering to the tip 1316. The release agent 1320 may comprise, for example, and without limitation, silicone, petroleum oil, fluorinated compounds (e.g., tetra fluoro ethylene-perfluoro alkylvinyl ether copolymer or perfluoroalkoxy), polytetrafluoroethylene, polyimide, polyetherimide, polyethersulfide, glycerin, or the like.

FIG. 60 corresponds to another process for making a sensor configured for direct press insertion according to the present embodiments. The sensor 1322 includes a sensor body 1324 with a sharp distal tip 1326. The sharp tip 1326 is coated with a sacrificial material 1328 that protects the tip 1326 during a subsequent step of applying a membrane 1330 to the sensor 1322, and that is later removed, as described below. The sacrificial material 1328 may any of a variety of materials that allows for simple removal. In certain embodiments, the sacrificial material may be light sensitive, heat sensitive, soluble, and/or pH sensitive, etc.

In any of the processes described herein for producing a sharp tip at the distal end of a fine sensor wire, including but not limited to those processes described in the foregoing paragraphs, the sensor wire may be embedded in a sacrificial material prior to any steps of removing material of the wire (such as grinding, laser cutting, etc.). The sacrificial material may increase the strength of the wire material and thereby enhance the efficacy of the material removal process by reducing the likelihood that the wire will break during the material removal process. Examples of sacrificial materials suited for use in the process of FIG. 60 include, without limitation, sugar, salts, degradable polymers, and waxes.

After the sacrificial material 1328 is applied to the sharp distal tip 1326 of the sensor 1322, the membrane 1330 is applied to the sensor 1322. Use of the sacrificial material allows for simplified application of the membrane, such that the membrane 1330 during the application process may cover not only the sensor body 1324 but also the distal tip 1326. The distal tip 1326 can then be treated to break down and/or remove the sacrificial layer and thereby facilitate removal of the membrane 1330 from the sharp distal tip 1326 without damaging the tip 1326. The type of post-membrane application treatment depends upon the type of sacrificial material(s) used, but may comprise, for example, and without limitation, applying light, heat, a solvent, and/or combinations thereof.

In another process, the membrane may be applied to the sensor, including over the sharpened distal tip, without any sacrificial material. The portion of the membrane applied to the distal tip may subsequently be heated until it softens enough such that it can be removed, for example, mechanically by scraping. For example, the softening step may comprise melting the membrane.

FIGS. 61 and 62 illustrate another process for making a sensor configured for direct press insertion according to the present embodiments. The sensor 1332 includes a sensor body 1334 with a sharp distal tip 1336. In a typical dipping process for applying a membrane 1338, the sensor 1332 is dipped vertically with the distal tip 1336 pointed downward, as shown in FIG. 61. If the membrane solution 1338 is allowed to dry with the distal tip 1336 pointed downward, gravity will pull the membrane 1338 solution downward, causing a bead to form. The bead dulls the distal tip 1336, rendering it less effective for piercing skin and/or tissue.

The process corresponding to FIG. 62 solves this problem by using gravity to lessen the likelihood of a bead forming. With reference to FIG. 62, the sensor 1332 is inverted, such that the sharp tip 1336 points upward, after dipping in the membrane solution 1338 and before the solution dries. In this orientation, gravity pulls the membrane solution 1338 away from the tip 1336, thereby reducing the likelihood of a bead forming. Instead, the membrane 1338 is more evenly distributed over the distal end of the sensor 1332, preserving the sharp distal tip 1336, as shown in FIG. 62. In an alternative process, the sensor 1332 may be rotated about an axis perpendicular to a longitudinal axis of the sensor 1332 while the membrane solution 1338 dries, allowing centripetal force to pull the membrane 1338 away from the tip 1336. In the process of rotating the sensor 1332, the sensor 1332 may be oriented horizontally, for example.

Figure 63:
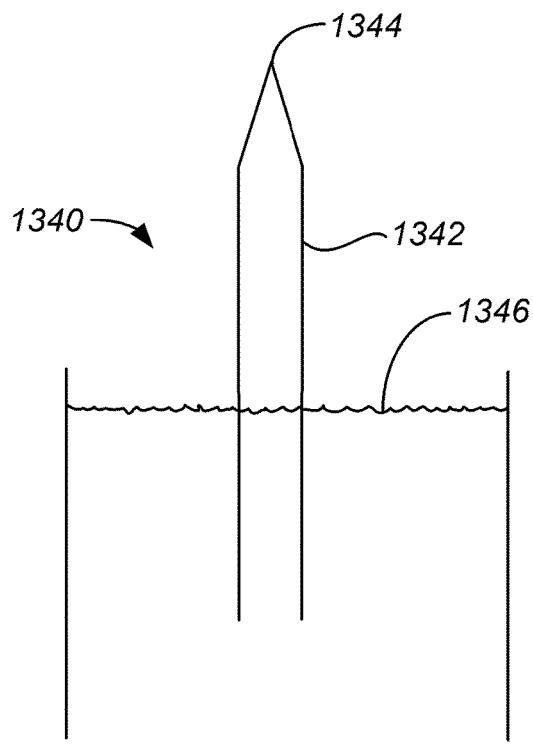
FIG. 63 is a schematic side elevation view of another process for making a sensor configured for direct press insertion according to the present embodiments.

FIG. 63 illustrates another process for making a sensor configured for direct press insertion according to the present embodiments. The sensor 1340 includes a sensor body 1342 with a sharp distal tip 1344. When dipping the sensor 1340 in a membrane solution 1346, the sensor 1340 is inverted, such that the sharp tip 1344 points upward. The sensor 1340 is only partially submerged, such that the membrane solution 1346 never contacts the sharp tip 1344. The sensor 1340 is subsequently removed from the membrane solution 1346 and allowed to dry. Because the membrane solution 1346 never contacts the sharp tip 1344, the sharpness of the tip 1344 is preserved.

Figure 64:
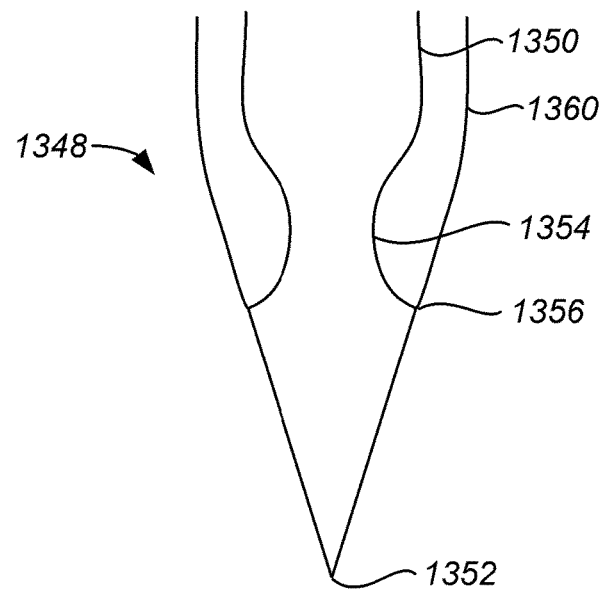
FIG. 64 is a schematic side elevation view of another process for making a sensor configured for direct press insertion according to the present embodiments.

FIG. 64 illustrates another process for making a sensor configured for direct press insertion according to the present embodiments. The sensor 1348 includes a sensor body 1350 with a sharp distal tip 1352. Just proximal of the tip 1352, an annular channel 1354 or depression is formed on the sensor body 1350. In some embodiments, a band of material is removed from the sensor 1348 to form the annular channel 1354 or depression. However, in other embodiments, the annular channel 1354 or depression may be formed by any of a variety of processes employed to alter the shape of a wire, such as, but not limited to, etching, skiving, grinding, or stamping. A distal end of the channel 1354 defines an edge 1356. When the sensor 1348 is subsequently dipped in a membrane solution, the edge 1356 causes the liquid meniscus of the membrane solution to break off, thereby leaving the tip 1352 of the sensor 1348 uncovered by the membrane 1360. Advantageously, the membrane 1360 does not blunt the sharp tip 1352.

One aspect of the present embodiments includes the realization that forming a sharp distal tip on a sensor presents challenges, such as contaminating the membrane surface and/or damaging the membrane so that it cannot perform its proper function. Contamination of the membrane can alter membrane properties such as diffusion. For example, a contaminant may reduce the permeability characteristics (e.g., permselectivity) of the membrane. Damage to the membrane can also affect the functionality of the sensor. For example, if membrane removal extends beyond the distal tip to a portion intended to cover the electroactive surface that forms an electrode, the sensor can become defective, as diffusion properties of the sensor become substantially altered and uncontrolled. On the other hand, if excess membrane material is present at the distal tip of the sensor, the distal tip of the sensor may become dull, such that it becomes less effective for piercing skin and/or tissue. Some of the present embodiments provide solutions to these problems, including how to form a sharp distal tip by removing material from the tip and how to form a sharp distal tip by adding material to the tip.

Figure 65:
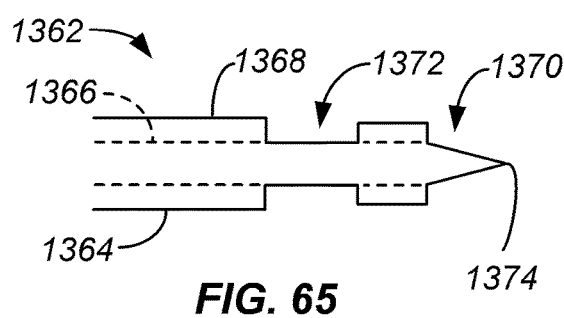
FIGS. 65-67 are schematic side elevation views of another process for making a sensor configured for direct press insertion according to the present embodiments.
Figure 66:
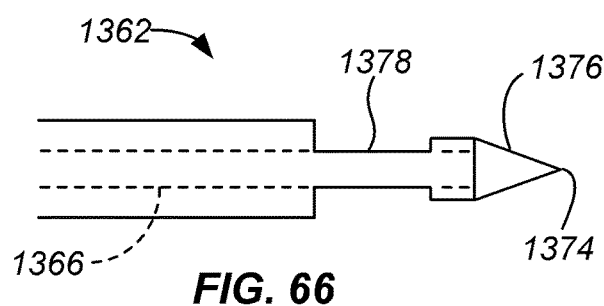
Figure 67:
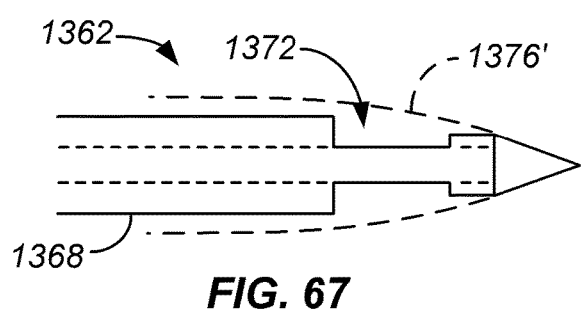

FIGS. 65-67 illustrate another process for making a sensor configured for direct press insertion according to the present embodiments. With reference to FIG. 65, the sensor 1362 includes a sensor body 1364 comprising a core 1366 and an outer layer 1368. The core 1366 may comprise, for example and without limitation, tantalum or any other material. The outer layer 1368 may comprise, for example and without limitation, platinum or any other material.

A first portion or band 1370 and a second portion or band 1372 of the outer layer 1368 are removed to expose the core 1366. The first band 1370 of removed material is located at the distal tip 1374 of the sensor body 1364, and the second band 1372 is located proximal of the distal tip 1374. The first and second bands 1370, 1372 may be removed using any process, such as skiving, etching, grinding, stamping, or any other processes. A portion of the core 1366 is also removed at the tip 1374 to form the sharp distal tip 1374. The core 1366 material may be removed using any process.

With reference to FIG. 66, a cap 1376 is attached over the distal tip 1374 of the sensor 1362. The attached cap 1376 includes a sharp distal end, and extends over a portion of the exposed core 1366, leaving a portion 1378 of the core 1366 proximal of the cap 1376 exposed. The cap 1376 may comprise an absorbable material such that the cap 1376 dissolves and/or is absorbed into the body of the host after the sensor 1362 is inserted into the host's skin and/or tissue. The material of the cap 1376 may comprise a dissolving polymer, such as, without limitation, degradable polymers including polyvinyl-pyrrolidone (PVP), polymerized sugar such as caramel, polyvinyl acetate, polyethylene glycol, polyesters, polyaminoacid, polycarbonate, polyanhydride, polylactic acid, polyglycolic acid, polydioxanone, polyhydroxybutyrate, polyhydroxyvalerate, polycaprolactone, polyanhydrides (e.g., aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, polyphosphazenes, and combinations or copolymers thereof and other similar polymers.

FIG. 67 illustrates an alternative configuration for the cap 1376' in which the cap 1376' extends farther proximally along the sensor 1362. For example, the cap 1376' may extend far enough proximally to cover at least a portion of the outer layer 1368 proximal of the area where the second band 1372 of the outer layer 1368 was removed.

In some embodiments, the elongated body (e.g., wire), precursor to individual workpieces that correspond to individual sensor pieces, is exposed to an agent that inactivates catalytic sites (e.g., enzymatic domains). The inactivating agent may be in any of a variety of forms, such as liquid or vapor. For example, in the process corresponding to FIG. 68, wire stock 1380 is exposed to vapor 1382 (e.g., cyanoacrylate) during singulation (i.e., the process of cutting wire stock into individual workpieces corresponding to sensor pieces). The vapor 1382 inactivates the catalytic sites at the sensor tip, thereby solving the problem of an elevated baseline signal from exposed metal at the tip. The process of FIG. 68 is advantageously well suited for, but does not require, reel-to-reel continuous processing.

Various processes are contemplated for producing a sharp tip at the distal end of a fine sensor wire. For example, the distal end of the sensor wire may be ground, or laser cut/laser ablated, or milled, or thermoformed (particularly for plastic materials), or processed according to any other technique(s) that can be used to shape the distal tip. The various processes for producing a sharp tip may produce a variety of tip shapes, such as, without limitation, beveled (similar to a hypodermic needle profile), cone shaped (similar to a pencil tip), or stepped (similar to an acupuncture needle).

FIG. 69 corresponds to another process for making a sensor configured for direct press insertion according to the present embodiments. In the process corresponding to FIG. 69, a distal end 1384 of a sensor wire 1386 is dipped in a chemical 1388 to remove material from the end of the wire 1386 and form a pointed tip 1390. The chemical 1388 into which the wire 1386 is dipped may be, for example, an etchant, such as an acid, or a polishing solution. In an alternative embodiment, the material may be removed from the end of the wire 1386 via electropolishing. In further embodiments, the material may be removed mechanically, for example, by mechanical scraping or mechanical polishing. Referring back to FIG. 69, the process illustrated therein may be advantageous for forming a tip on a very fine flexible wire where more traditional processes for forming a sharp tip, such as grinding, may not work well.

FIG. 70 corresponds to another process for making a sensor configured for direct press insertion according to the present embodiments. In the process of FIG. 70, a distal end 1392 of a sensor wire 1394 is dragged across an abrasive surface 1396 with the sensor wire 1394 held at an angle η between 0° and 900 relative to the abrasive surface 1396. For example, Θ may be from about 150 to about 55°, sometimes from about 150 to about 30°, and other times from about 300 to about 45°, or any other appropriate angle. The wire 1394 may be held within a support fixture (not shown) as it is moved relative to the abrasive surface 1396. Alternatively, the wire 1394 may be held still and the abrasive surface 1396 may be moved relative to the wire 1394. The process of FIG. 70 may, for example, produce a wedge-shaped tip 1398 having a single flat bevel 1400 on the distal end 1392 of the wire 1394. The wedge-shaped tip 1398 may be simpler and/or less expensive to produce than a multifaceted (e.g. pyramidal) or conical point.

In the process of FIG. 70, a support fixture for holding the wire 1394 may comprise a block having a small hole for receiving the wire 1394, with a longitudinal axis of the hole being oriented at the angle Θ relative to the abrasive surface 1396. In another alternative, the wire 1394 may be held between two flat blocks cut at the angle Θ relative to the abrasive surface 1396.

FIG. 71 corresponds to another process for making a sensor configured for direct press insertion according to the present embodiments. In FIG. 71, a sensor wire 1402 includes an inner core 1404 and an outer layer 1406. The inner core 1404 has a very small diameter, such as, for example, less than about 400 µm, less than about 200 µm, or less than about 100 µm. In the process of FIG. 71, a portion of the outer layer 1406 at the distal end of the sensor wire 1402 is removed from the inner core 1404 to expose a short length 1408 of the inner core 1404 at the distal end only. The exposed length 1408 of the inner core 1404 has a sufficiently small diameter that it can penetrate skin and/or tissue. The exposed portion 1408 of the inner core 1404 is preferably long enough to penetrate the host to a desired depth, but preferably as short as possible to achieve the desired depth so that the outer layer 1406 provides support to the exposed portion 1408 of the inner core 1404 to increase the column strength of the exposed portion 1408. The outer layer 1406 may be removed from the inner core 1404 using any process, such as mechanical stripping, laser ablation, bead blasting, abrasion, chemical etching, or any other process.

Figure 72:
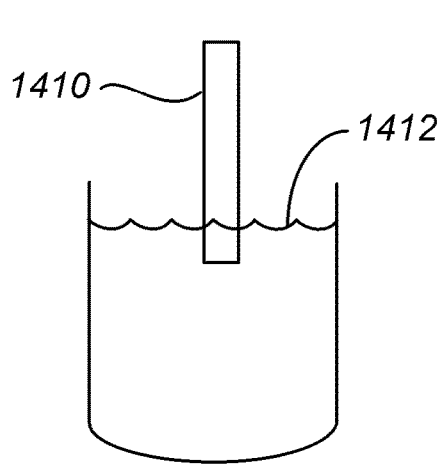
FIGS. 72 and 73 are schematic side elevation views of another process for making a sensor configured for direct press insertion according to the present embodiments.
Figure 73:
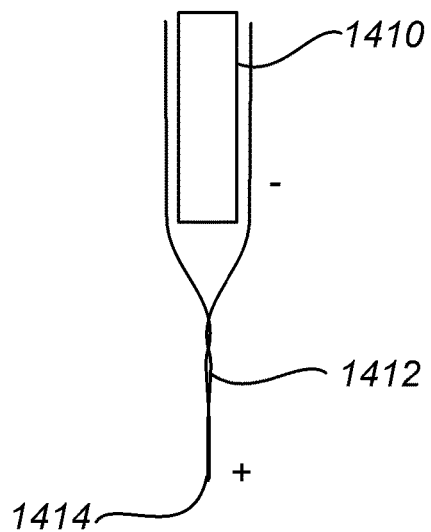

Some of the present processes for forming a sensor wire form a sharp distal tip by adding material to the sensor wire. For example, FIGS. 72 and 73 illustrate another process for making a sensor configured for direct press insertion according to the present embodiments. With reference to FIG. 72, the sensor wire 1410 is dipped in a bath of a polymer material 1412. The polymer material 1412 may comprise, for example and without limitation, conductive polymer, polyelectrolyte, zwitterionic polymers, etc. After removing the sensor from the bath, a voltage is applied across the polymer material 1412, as shown in FIG. 73. The voltage causes the polymer material 1412 to elongate and form a sharp tip 1414.

For example, the process of FIGS. 72 and 73 may comprise electrospinning. In electrospinning, when a sufficiently high voltage is applied to a liquid droplet, the body of the liquid becomes charged, and electrostatic repulsion counteracts the surface tension and the droplet is stretched. At a critical point, a stream of liquid erupts from the surface. This point of eruption is known as the Taylor cone. If the molecular cohesion of the liquid is sufficiently high, stream breakup does not occur (if it does, droplets are electrosprayed) and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from this bending instability leads to the formation of uniform fibers with nanometer-scale diameters.

Figure 74:
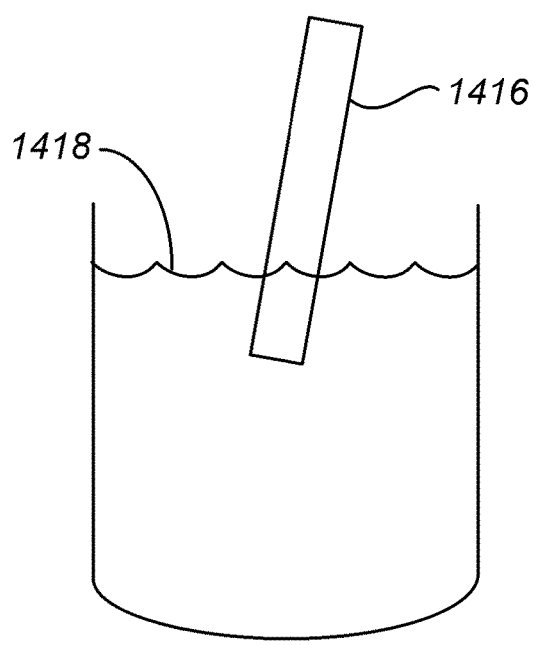
FIGS. 74 and 75 are schematic side elevation views of another process for making a sensor configured for direct press insertion according to the present embodiments.
Figure 75:
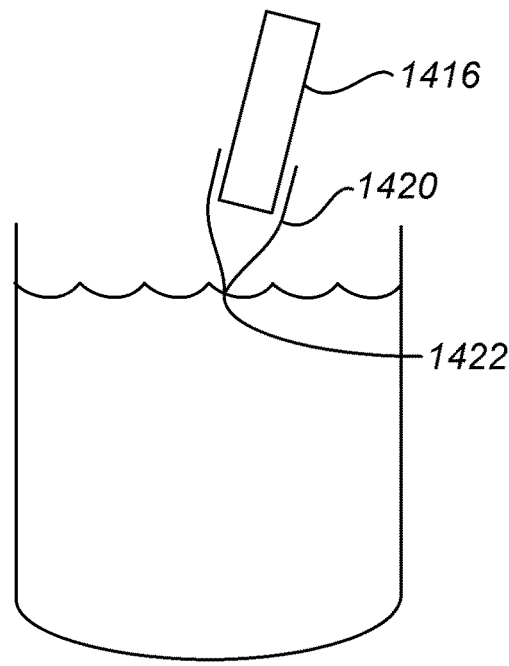

FIGS. 74 and 75 illustrate another process for making a sensor configured for direct press insertion according to the present embodiments. With reference to FIG. 74, a sensor wire 1416 is dipped in a bath 1418 of molten polymers, or a mixture of reactive monomer/oligomer, or dissolved polymers, or a polymer mixture. With reference to FIG. 75, dipping the sensor wire 1416 produces a dip coating 1420 on the portion of the sensor wire 1416 that is submerged in the bath 1418. With reference to FIG. 75, the wire 1416 is withdrawn from the bath 1418, and as the wire 1416 withdraws the dip coating 1420 cures to create a sharp tip 1422 on the sensor wire 1416. The withdrawal speed and angle can be controlled such that the tip conforms to the desired shape and sharpness. The tip can then be cooled to harden, dried to solidify, or cured by exposure to external radiation, moisture, and/or light. In some embodiments, after the wire 1416 is withdrawn from the bath 1418 of molten polymers, the tip 1422 is placed into a mold to produce the sharp tip 1422.

Figure 76:
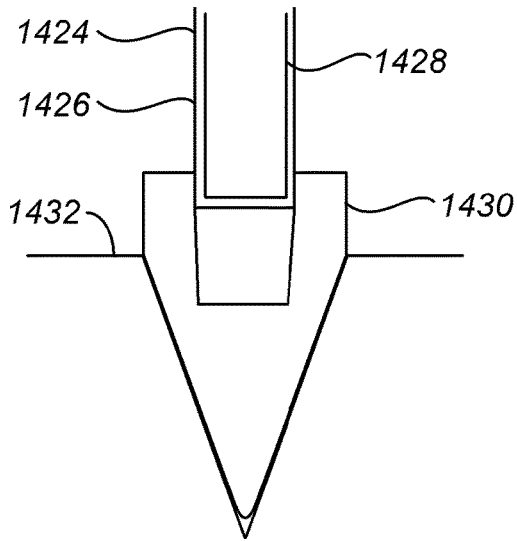
FIG. 76 is a schematic side elevation view of another process for making a sensor configured for direct press insertion according to the present embodiments.

FIG. 76 illustrates another process for making a sensor configured for direct press insertion according to the present embodiments. In the process of FIG. 76, a sensor wire 1424 includes a sensor body 1426 and a membrane 1428 covering at least a portion of the sensor body 1426. A hard and sharp tip 1430 is secured to the membrane-covered sensor wire 1424. For example, the tip 1430 may be cast onto the wire 1424 using a mold 1432. If the tip 1430 is a moldable material, such as a thermoplastic, the tip 1430 may be injection molded or insert molded to secure it to the sensor body 1426. Other curable materials, such as two-part polyurethane, can be used in a low temperature liquid injection molding process (LIM) to avoid exposing the membrane to a high temperature.

Figure 76A:
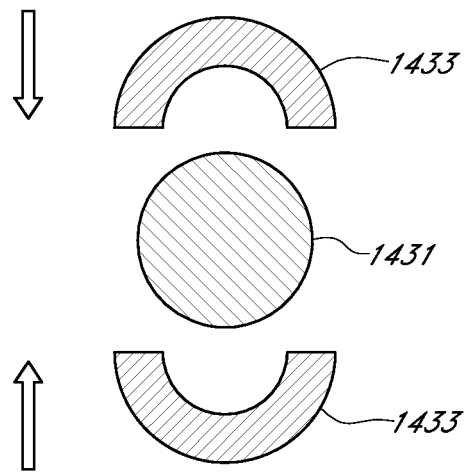
FIG. 76A is a schematic end elevation view of another process for making a sensor configured for direct press insertion according to the present embodiments.
Figure 76B:
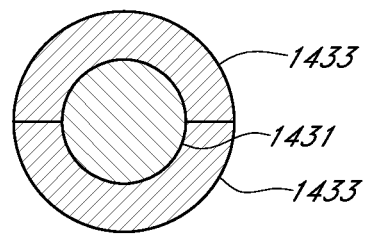
FIG. 76B-76D are cross-sectional schematic end views of the process for making a sensor configured for direct press insertion according to FIG. 76A.
Figure 76C:
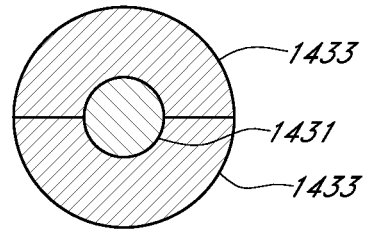
Figure 76D:
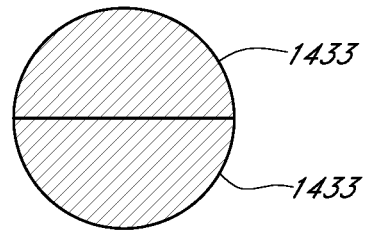

In any of the embodiments described herein, the distal tip of the sensor workpiece may be shaped via press molding. For example, in the embodiment illustrated in FIG. 76A, the sensor workpiece 1431 is first introduced into a station for press molding. Shaping elements 1433 are then moved from an expanded position (FIG. 76A) into a contracted position (FIG. 76B), whereby the distal end of the workpiece 1431 is molded into a desired shape. FIG. 76B illustrates a cross-section of a portion of the sensor workpiece 1431 that is being shaped by the shaping elements 1433 and more proximal than the portion illustrated in FIG. 76C, which in turn is more proximal than the distal tip illustrated in FIG. 76D, which has a cross-section with an area that is almost zero and thus forms a sharp tip. In the embodiment shown in FIGS. 76A-76D, there are two shaping elements 1433, which shape the distal end of the workpiece 1431 into a conical shape with a circular cross-section. However, in other embodiments, there may be any number of shaping elements, such as, for example, three, four, five, nine, ten, or more. In addition, the shaping elements 1433 may be configured to shape the distal end into any variety of shapes, for example, triangular, rectangular, square, pentagon, or hexagon.

Figure 77:
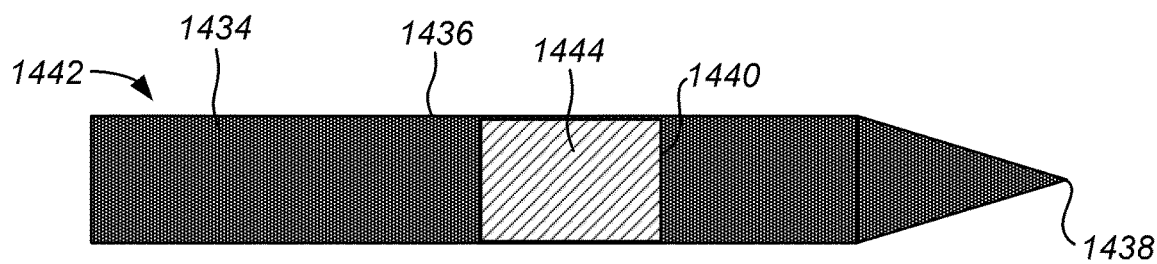
FIG. 77 is a schematic tip plan view of another process for making a sensor configured for direct press insertion according to the present embodiments.
Figure 78:
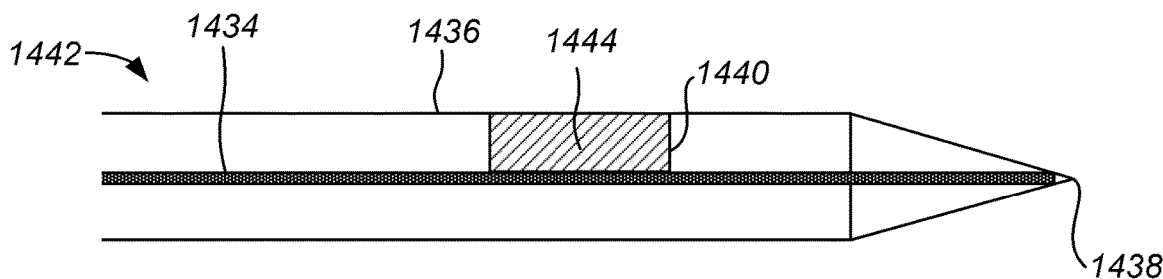
FIG. 78 is schematic side elevation view of the process of FIG. 77.

FIGS. 77 and 78 illustrate another process for making a sensor configured for direct press insertion according to the present embodiments. FIG. 77 is a top plan view, and FIG. 78 is a side elevation view. With reference to FIGS. 77 and 78, the process includes a planar, flexible printed circuit board (PCB) 1434 embedded in an outer core 1436. In the illustrated embodiment, the outer core 1436 is substantially cylindrical and includes a conical distal tip 1438 configured for piercing skin and/or tissue. However, the illustrated shape is just one example and is not limiting. The outer core 1436 may comprise any material, such as a polymer.

In the process of FIGS. 77 and 78, a section of the outer core 1436 proximal of the conical tip 1438 is removed, creating a window 1440. For example, the outer core 1436 section may be removed via laser ablation, or any other process described herein or elsewhere for removing material from a workpiece. In one example, an outer surface of the PCB 534 includes a platinum layer, which resists laser ablation. Thus, when the outer core 1436 section is removed via laser ablation, the portion of the PCB 1434 that lies beneath the window 1440 remains intact. The sensor 1442 is subsequently dipped in a membrane solution. The membrane 1444 covers the exposed platinum surface of the PCB 1434 within the window 1440, and this surface defines a working electrode in the finished sensor 1442.

Figure 79:
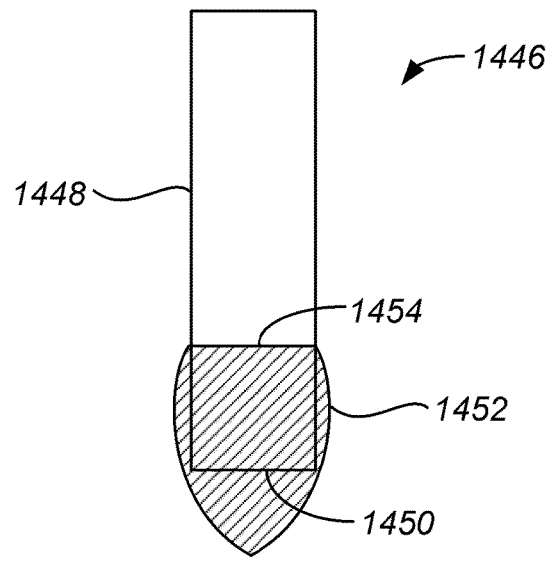
FIG. 79 is a schematic side elevation view of another process for making a sensor configured for direct press insertion according to the present embodiments.

FIG. 79 illustrates another process for making a sensor configured for direct press insertion according to the present embodiments. The sensor 1446 includes a sensor body 1448 having a blunt distal end 1450. A piercing tip 1452 is positioned over the distal end 1450. The tip 1452 includes an open proximal end 1454 that receives the distal end 1450 of the sensor body 1448. The proximal end 1454 of the piercing tip 1452 is then crimped to secure the tip 1452 to the sensor body 1448. In some embodiments, the membrane is applied before the sensor body 1448 is crimped to the tip 1422. In other embodiments, the membrane is applied after the sensor body 1448 is crimped to the tip 1422. In a further embodiment, the sensor 1446 is dipped upside down (i.e., with the tip 1422 on top) such that the solution never contacts the tip. This process avoids the possibility of the membrane getting onto (and dulling) the tip.

In another embodiment, a piercing tip may be overmolded on the distal end of the sensor body. The overmolded tip may comprise, for example and without limitations, a rigid polymer such as a two-part polyurethane. The rigid tip may be overmolded on the distal end of the sensor body after the membrane has been applied to the sensor body.

Another aspect of the present embodiments includes the realization that it can be difficult to form three electrodes on an analyte sensor. For example, adding a third layer to a sensor wire adds significant complexity to the wire manufacturing process and makes it very difficult to achieve concentricity of all layers. If all layers are not concentric, further processing steps, such as skiving, can be difficult to perform with the desired precision. Further, the tip of the sensor can reduce sensor accuracy if conductive material and/or enzyme(s) at the tip are exposed to the environment. Some of the present embodiments provide solutions to these problems.

Figure 80:
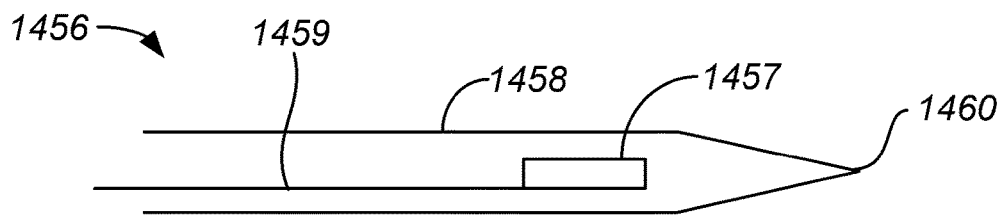
FIGS. 80 and 81 are schematic top plan views of another process for making a sensor configured for direct press insertion according to the present embodiments.
Figure 81:
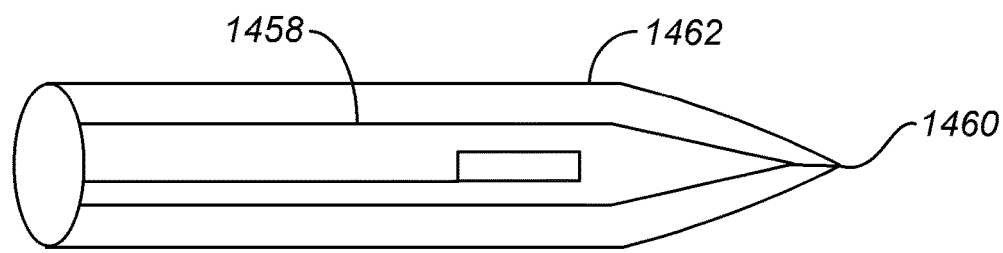

For example, FIGS. 80 and 81 illustrate another process for making a sensor configured for direct press insertion according to the present embodiments. With reference to FIG. 80, the sensor 1456 includes a thin, flat microelectromechanical systems (MEMS) substrate 1458. For example, the MEMS substrate 1458 may be fabricated using photolithography, etching, and/or other MEMS processes.

A distal end of the substrate includes a tapered piercing tip 1460. An electroactive surface, or electrode, 1457 is printed on the MEMS substrate 1458. A conductive trace 1459 provides electrical connection between the electrode 1457 and electrical contacts (not shown) of the sensor 1456. With reference to FIG. 81, the substrate 1458 is coated with a membrane 1462. For example, the membrane coating 1462 may be applied with a dip coat process to obtain a conformal coating. In the illustrated embodiment, the membrane coating 1462 is substantially cylindrical and covers the piercing tip 1460 of the substrate 1458.

The process illustrated in FIGS. 80 and 81 advantageously leverages the benefits of both MEMS processing and dip coating to obtain a cylindrical direct press insertion sensor having three electrodes. Using MEMS technology, all three electrodes can be easily fabricated on the flat, flexible substrate 1458. For example, the working electrode (and possibly other electrodes) may be on top and bottom surfaces of the substrate 1458 for averaging. The substrate 1458 with electrodes is subsequently dipped into a hard membrane solution to obtain the cylindrical membrane coating 1462. The membrane 1462 may be, for example, a shape memory material and/or a heat/hydration softening material. While the membrane coating 1462 need not be cylindrical, a cylindrical membrane coating advantageously enables radial diffusion of the analyte, which is beneficial, because radial diffusion facilitates faster mass transport, leading to shortened response times to achieve steady state. Further, the MEMS substrate 1458 can be inert, thereby eliminating the issue of tip robustness.

One aspect of the present embodiments includes the realization that a piercing tip can be formed on sensors during a step of singulating a sensor wire into individual sensors. For example, singulating processes may include, without limitation, mechanical pressing, hot pressing, laser ablation, extruding, milling, etc. By forming a piercing tip during singulation, a sharp distal tip can be formed prior to applying the membrane to the sensor, thereby avoiding cross-contamination and damaging the delicate membrane with a subsequent tip-forming step.

Figure 82:
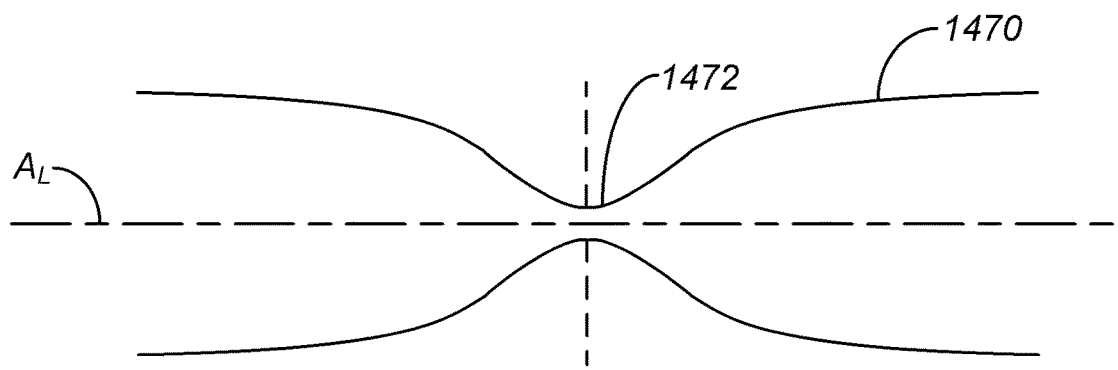
FIG. 82 is a schematic side elevation view of another process for making a sensor configured for direct press insertion according to the present embodiments.

For example, FIG. 82 illustrates another process for making a sensor configured for direct press insertion according to the present embodiments. Forming a sensor tip configured for piercing skin and/or tissue is difficult with certain materials. Typical processes like grinding are not suitable for materials like aluminum, tantalum, etc. FIG. 82 illustrates an alternative process in which the sensor is pulled to form a sharp tip.

In general, when an elongate piece of material is placed in tension along its longitudinal axis and pulled past its elastic limit, it begins to plastically deform. Depending on the material's properties, the material may "neck." Necking is the localized concentration of strain that occurs as the cross sectional area of the material increases and the stress at the reduced cross section simultaneously increases. Necking rapidly increases the rate of deformation at the area of reduced cross section. From the point where necking occurs, future deformation is concentrated in the necking area. In practice, for a sample having a circular cross section, necking produces a localized reduction in diameter. Eventually, the sample fails at or near the center of the necked section. This failure leaves two "half necks," each of which includes a sharp point that can be used to form a piercing tip for a sensor.

According to the above process, and with reference to FIG. 82, a sensor wire 1470 is placed in tension along its longitudinal axis $A_L$. The sensor wire 1470 necks in an intermediate region 1472. After failure occurs, two sensors having sharp piercing tips are formed. Further processing may be performed on the piercing tips, such as burr removal, polishing, further sharpening, etc.

Figure 83:
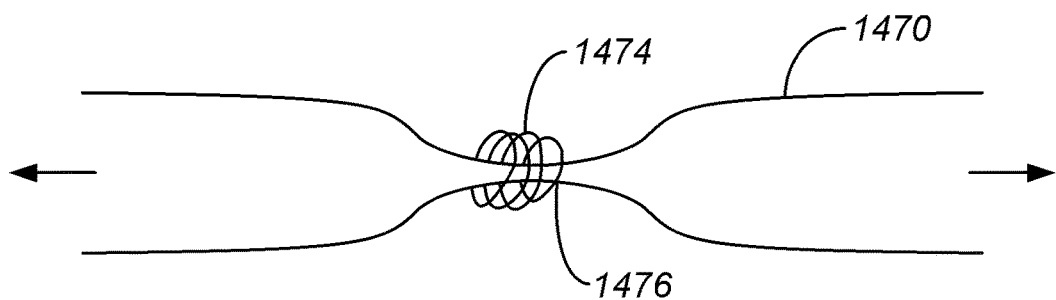
FIG. 83 is a schematic side elevation view of another process for making a sensor configured for direct press insertion according to the present embodiments.

In one alternative, as shown in FIG. 83, a portion of the sensor wire 1470 may be heated before and/or during the process of applying tension. For example, heat may be applied with a resistive heating element 1474, a flame, or any other heat source. The applied heat softens the wire material, making it more likely that necking and failure will occur in the heated region 1476.

Also in one alternative, after tension is applied to the sensor wire and necking begins to occur, but prior to failure, the tension may be released and the two portions of the sensor wire on either side of the necked region may be separated by any process, such as shearing, cutting, laser ablation, etc.

Figure 84:
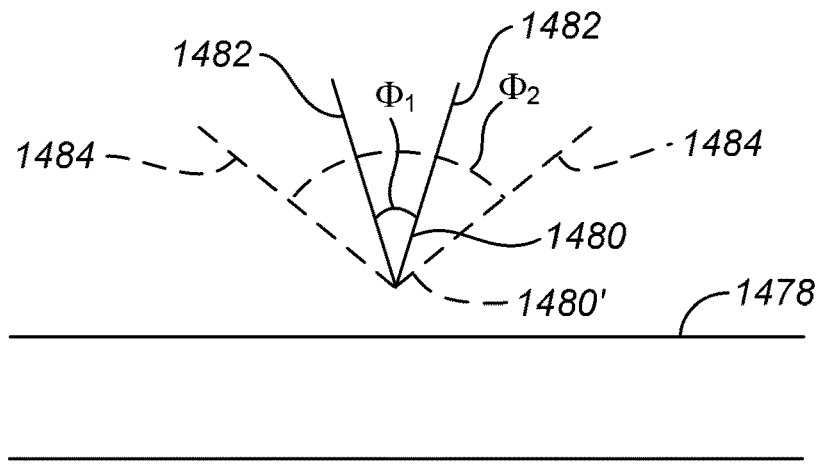
FIGS. 84-86 are schematic side elevation views of another process for making a sensor configured for direct press insertion according to the present embodiments.
Figure 85:
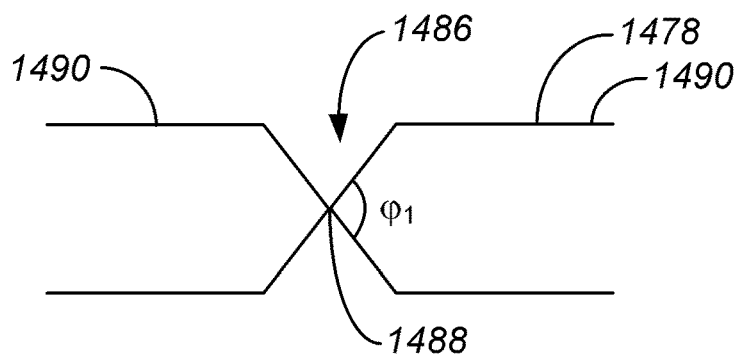
Figure 86:
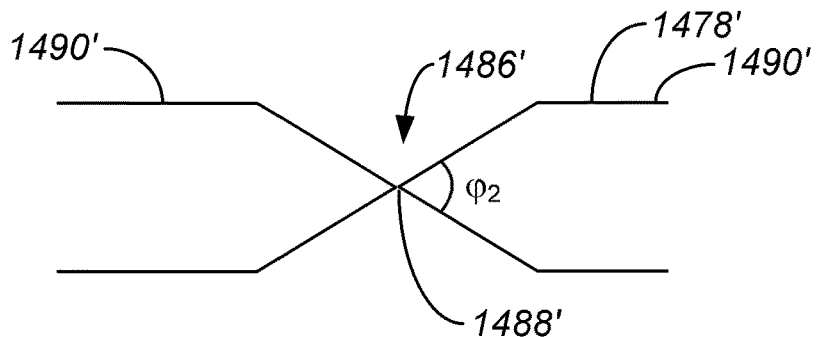

FIGS. 84-86 illustrate another process for making a sensor configured for direct press insertion according to the present embodiments. With reference to FIG. 84, a sensor wire 1478 is positioned between opposing cutting blades 1480. The cutting blades 1480 singulate the sensor wire 1478 into smaller pieces, each of which is subsequently processed to produce a sensor. FIG. 84 illustrates a first embodiment of the cutting blades 1480 in solid lines, and a second embodiment of the cutting blades 1480' in dashed lines. In the solid line embodiment 1480, each blade 1480 includes a cutting edge defined by converging surfaces 1482 that lie at a first angle $\Phi_1$ to one another. In the dashed line embodiment, each blade 1480' includes a cutting edge defined by converging surfaces 1484 that lie at a second angle $\Phi_2$ to one another, where $\Phi_2 > \Phi_1$. FIG. 85 illustrates the shape of the cut 1486 made in the sensor wire 1478 by the blades 1480 of the solid line embodiment, and FIG. 86 illustrates the shape of the cut 1486' made in the sensor wire 1478' by the blades 1480' of the dashed line embodiment. Because $\Phi_2 > \Phi_1$, the cut 1486' made in the sensor wire 1478' by the blades 1480' of the dashed line embodiment results in a smaller angle $\varphi_2$ defined between the converging surfaces at the piercing tips 1488' of the sensors 1490' in FIG. 86 as compared to the angle $\varphi_1$ defined between the converging surfaces at the piercing tips 1488 of the sensor wires 1490 in FIG. 85. The smaller angle $\varphi_2$ advantageously creates a sharper point on the sensor wires 1490' in FIG. 86 as compared to the sensor wires 1490 in FIG. 85. Thus, by using the blades 1480' of the dashed line embodiment in FIG. 84, sharper piercing tips may be produced.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-

0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No.

12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; and U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A sensor device for measuring an analyte concentration in a host, comprising:
   a sensor unit comprising a sensor body, at least one electrode, and a membrane covering at least a portion of the at least one electrode;
   a piercing element at a distal end of the sensor unit, the piercing element being configured for piercing skin and/or tissue of the host;
   a mounting unit spaced from a sensor tip and configured to support the sensor device on an exterior surface of the skin of the host; and
   a retractable introducer sheath configured to cover at least a portion of the membrane during insertion of the sensor device through the skin of the host, and configured to support the sensor body to increase resistance of the sensor body to buckling during insertion of the sensor device through the skin of the host.

2. The sensor device of claim 1, wherein a proximal end of the piercing element has a diameter greater than a diameter of the sensor body.

3. The sensor device of claim 2, wherein a diameter of the retractable introducer sheath is substantially equal to or less than the diameter of the proximal end of the piercing element.

4. The sensor device of claim 1, wherein the retractable introducer sheath is configured to provide the sensor body with additional column strength to increase the resistance of the sensor body to the buckling during the insertion of the sensor device through the skin of the host.

5. The sensor device of claim 1, wherein the retractable introducer sheath is configured to withdraw from the skin of the host after the insertion.

6. The sensor device of claim 1, wherein the sensor device comprises an in vivo portion configured for insertion under the skin of the host.

7. The sensor device of claim 6, wherein the in vivo portion is configured for insertion without a removable needle.

8. The sensor device of claim 1, wherein the sensor unit comprises a hydration-responsive material.

9. The sensor device of claim 8, wherein in response to hydration, the hydration-responsive material changes at least one of hardness, shape, or modulus of elasticity.

10. The sensor device of claim 1, wherein the sensor body comprises a stimulus-responsive material configured to change at least one property including shape in response to a stimulus.

* * * * *